(12) United States Patent
White

(10) Patent No.: US 12,065,504 B2
(45) Date of Patent: Aug. 20, 2024

(54) ANTI-GLYCO-MUC1 ANTIBODIES AND THEIR USES

(71) Applicant: GO Therapeutics, Inc., Cambridge, MA (US)

(72) Inventor: Thayer White, Boxford, MA (US)

(73) Assignee: GO Therapeutics, Inc., Cambridge, MA (US)

( * ) Notice: Subject to any disclaimer, the term of this patent is extended or adjusted under 35 U.S.C. 154(b) by 364 days.

(21) Appl. No.: 17/488,723

(22) Filed: Sep. 29, 2021

(65) Prior Publication Data
US 2022/0089772 A1 Mar. 24, 2022

Related U.S. Application Data

(62) Division of application No. 16/168,259, filed on Oct. 23, 2018, now Pat. No. 11,161,911.

(60) Provisional application No. 62/576,297, filed on Oct. 24, 2017, provisional application No. 62/575,666, filed on Oct. 23, 2017.

(51) Int. Cl.
| | |
|---|---|
| C07K 16/30 | (2006.01) |
| A61K 39/00 | (2006.01) |
| A61K 47/68 | (2017.01) |
| A61P 35/00 | (2006.01) |
| C07K 14/47 | (2006.01) |
| C07K 14/54 | (2006.01) |
| C07K 14/705 | (2006.01) |
| C07K 14/715 | (2006.01) |
| C07K 14/725 | (2006.01) |
| C07K 16/28 | (2006.01) |
| C07K 16/46 | (2006.01) |
| G01N 33/574 | (2006.01) |
| G01N 33/68 | (2006.01) |

(52) U.S. Cl.
CPC .... *C07K 16/3092* (2013.01); *A61K 39/00117* (2018.08); *A61K 47/6849* (2017.08); *A61K 47/6851* (2017.08); *A61K 47/6869* (2017.08); *A61K 47/6897* (2017.08); *A61P 35/00* (2018.01); *C07K 14/4727* (2013.01); *C07K 14/5443* (2013.01); *C07K 14/7051* (2013.01); *C07K 14/70517* (2013.01); *C07K 14/70521* (2013.01); *C07K 14/70578* (2013.01); *C07K 14/7155* (2013.01); *C07K 16/2809* (2013.01); *C07K 16/468* (2013.01); *G01N 33/574* (2013.01); *G01N 33/57469* (2013.01); *G01N 33/6854* (2013.01); *A61K 2039/505* (2013.01); *C07K 2317/31* (2013.01); *C07K 2317/34* (2013.01); *C07K 2317/35* (2013.01); *C07K 2317/522* (2013.01); *C07K 2317/524* (2013.01); *C07K 2317/526* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2319/30* (2013.01); *G01N 2333/4725* (2013.01)

(58) Field of Classification Search
None
See application file for complete search history.

(56) References Cited

U.S. PATENT DOCUMENTS

| | | | |
|---|---|---|---|
| 8,440,798 B2 | 5/2013 | Clausen et al. |
| 8,722,856 B2 | 5/2014 | Nishimura et al. |
| 8,883,977 B2 | 11/2014 | Nishimura et al. |
| 8,912,311 B2 | 12/2014 | Clausen et al. |
| 9,359,436 B2 | 6/2016 | Clausen et al. |
| 9,588,121 B2 | 3/2017 | Wandall et al. |
| 2002/0132771 A1 | 9/2002 | Madiyalakan |
| 2002/0146750 A1 | 10/2002 | Hoogenboom et al. |
| 2003/0186850 A1 | 10/2003 | Clausen et al. |
| 2007/0044171 A1 | 2/2007 | Kovalic et al. |
| 2009/0162359 A1 | 6/2009 | Klein |
| 2010/0034825 A1 | 2/2010 | Clausen et al. |
| 2010/0278818 A1 | 11/2010 | Hubert-Haddad et al. |
| 2010/0322935 A1 | 12/2010 | Croasdale et al. |
| 2011/0172392 A1 | 7/2011 | Kajihara et al. |
| 2012/0040375 A1 | 2/2012 | Nishimura et al. |
| 2012/0128676 A1 | 5/2012 | Goletz et al. |
| 2012/0276104 A1 | 11/2012 | Woisetschlager |
| 2013/0045490 A1 | 2/2013 | Yonezawa |
| 2013/0045543 A1 | 2/2013 | Nishimura et al. |
| 2013/0337505 A1 | 12/2013 | Mekada et al. |
| 2015/0005474 A1 | 1/2015 | Goletz et al. |

(Continued)

FOREIGN PATENT DOCUMENTS

| | | |
|---|---|---|
| CN | 106661110 A | 5/2017 |
| EP | 2351777 B1 | 10/2015 |

(Continued)

OTHER PUBLICATIONS

Almagro & Fransson, Frontiers in Bioscience 2008; 13:1619-33 (Year: 2008).

(Continued)

*Primary Examiner* — Peter J Reddig
(74) *Attorney, Agent, or Firm* — Biospark Intellectual Property Law

(57) ABSTRACT

The present disclosure relates to anti-glyco-MUC1 antibodies and antigen binding fragments thereof that specifically bind to a cancer-specific glycosylation variant of MUC1 and related fusion proteins and antibody-drug conjugates, as well as nucleic acids encoding such biomolecules. The present disclosure further relates to use of the antibodies, antigen-binding fragments, fusion proteins, antibody-drug conjugates and nucleic acids for cancer therapy.

Figure 1:
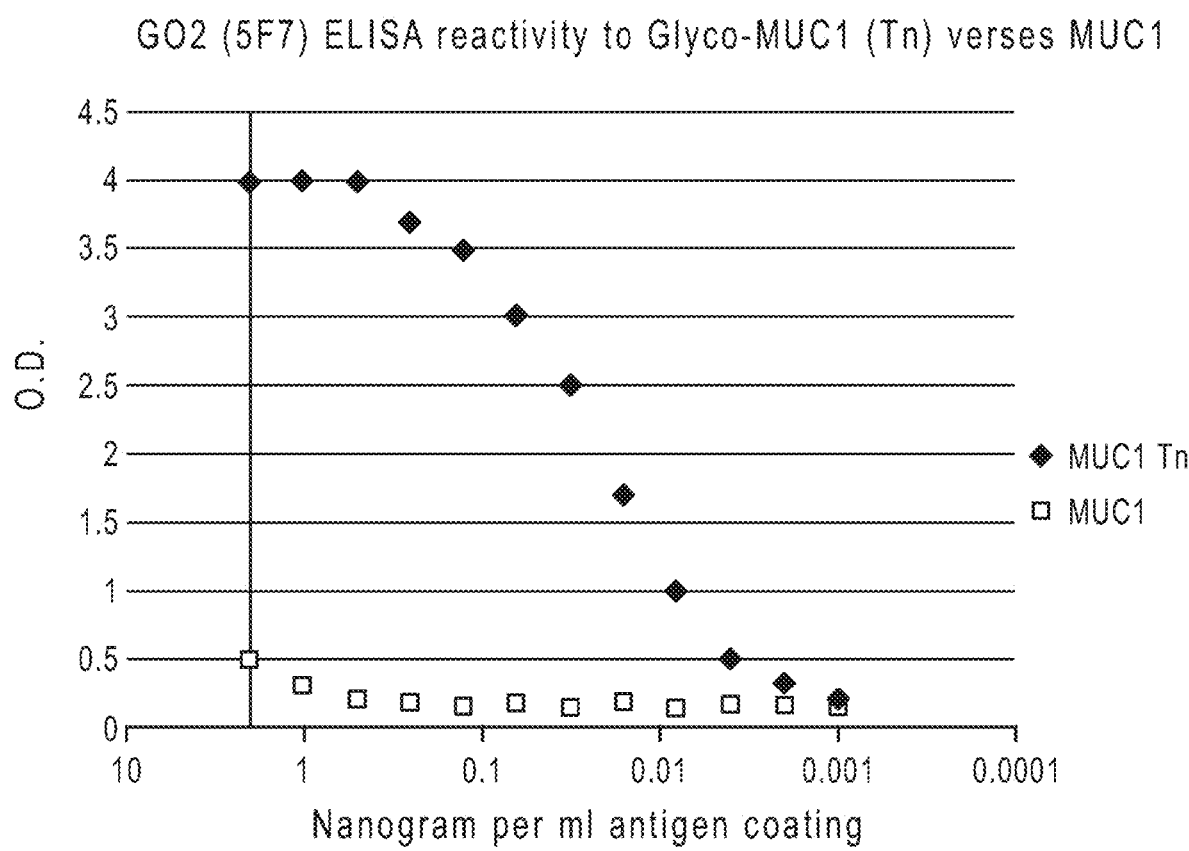

32 Claims, 20 Drawing Sheets
Specification includes a Sequence Listing.

(56) References Cited

U.S. PATENT DOCUMENTS

| | | |
|---|---|---|
| 2015/0166670 A1 | 6/2015 | Castoldi et al. |
| 2016/0145343 A1 | 5/2016 | Schoen et al. |
| 2016/0176980 A1 | 6/2016 | Chang et al. |
| 2017/0129962 A1 | 5/2017 | Regula et al. |
| 2017/0145116 A1 | 5/2017 | Regula et al. |
| 2020/0131275 A1 | 4/2020 | Goletz et al. |

FOREIGN PATENT DOCUMENTS

| | | |
|---|---|---|
| WO | 89/08711 | 9/1989 |
| WO | 2008/040362 A2 | 4/2008 |
| WO | 2008/119353 A1 | 10/2008 |
| WO | WO 2011012309 | 2/2011 |
| WO | 2014/051433 A1 | 4/2014 |
| WO | WO2015120180 A1 | 8/2015 |

OTHER PUBLICATIONS

CROSSMAB (Trademark Electronic Search System, downloaded Mar. 23, 2021) (Year: 2021).

Kimarsky et al., 2002, "Structural analysis of peptide substrates for O-glycosylation," pp. 713-714.

Reiersen et al. (Nucleic Acids Res. 2005 33(1): e10) (Year: 2005).

Beatson et al., 2015, "The Breast Cancer-Associated Glycoforms of MUC1, MUC1-Tn and sialyl-Tn, Are Expressed in COSMC Wild-Type Cells and Bind the C-Type Lectin MGL," PLoS ONE, 10(5): e0125994.

Extended European Search Report issued Feb. 28, 2022 in connection with application No. 19826976.3.

International Search Report and Written Opinion for PCT/US2019/039883, mailed Oct. 22, 2019.

Katayose et al., 1996, "MUC1-specific Targeting Immunotherapy with Bispecific Antibodies: Inhibition of Xenografted Human Bile Duct Carcinoma Growth," Cancer Research, 56:4205-4212.

Posey et al., 2016, "Engineered CAR T Cells Targeting the Cancer-Associated Tn-Glycoform of the Membrane Mucin MUC1 Control Adenocarcinoma," Immunity, 44:1444-1454.

Song et al., 2012, "MUC1 glycopeptide epitopes predicted by computational glycomics," International Journal of Oncology, 41:1977-1984.

Wandall et al., 2007, "The lectin domains of polypeptide GalNAc-transferases exhibit carbohydrate-binding specificity for GalNAc: lectin binding to GalNAc-glycopeptide substrates is required for high density GalNAc-O-glycosylation," Glycobiology 17(4):374-387.

Zhou et., 2018, "Epitopes of MUC1 Tandem Repeats in Cancer as Revealed by Antibody Crystallography: Toward Glycopeptide Signature-Guided Therapy" Molecules, 23, 1326.

International Search Report issued Mar. 29, 2018 in connection with PCT/US2017/058036.

Written Opinion issued Mar. 29, 2018 in connection with PCT/US2017/058036.

Extended European Search Report issued Apr. 19, 2021 in connection with 17929557.1.

Bennett et al., 1998, "Cloning of a Human UDP-N-Acetyl-α-Galactosamine:Polypeptide N-Acetylgalactosaminyltransferase That Complements Other GalNAc-Transferases in Complete O-Glycosylation of the MUC1 Tandem Repeat," The Journal of Biological Chemistry, 273(46):30472-30481.

Brokx et al., 2003, "Nuclear Magnetic Resonance-Based Dissection of Glycosyltransferase Specificity for the Mucin MUC1 Tandem Repeat," Biochemistry, 42(47):13817-13825.

Dalziel et al., 2001, "The Relative Activities of the C2GnT1 and ST3Gal-I Glycosyltransferases Determine O-Glycan Structure and Expression of an Tumor-associated Epitope on MUC1," The Journal of Biological Chemistry, 276(14):11007-11015.

De Bono et al., 2004, "Phase I trial of a murine antibody to MUC1 in patients with metastatic cancer: evidence for the activation of humoral and cellular antitumor immunity," Annals of Oncology, 15:1825-1833.

Dualogics, "The OrthoMab platform—How it works," downloaded from https://www.dualogics.com/technology/ on Oct. 9, 2017.

Fontenot et al. 1993 "Synthesis of large multideterminant peptide immunogens using a poly-proline beta-turn helix motif" Database Biosis, Biosciences Information Service, XP55796187, Database accession No. PREV199497079884.

Fritz et al., 2004, "The beginnings of mucin biosynthesis: The crystal structure of UDP-GalNAc:polypeptide α-N-acetylgalactosaminyltransferase-T1," PNAS, 101(43): 15307-15312.

Irimura et al., 1999, "Diverse Glycosylation of MUC1 and MUC2: Potential Significance in Tumor Immunity," J. Biochem., 126:975985.

Kagan et al., 2004, "Comparison of antigen constructs and carrier molecules for augmenting the immunogenicity of the monosaccharide epithelial cancer antigen Tn," Cancer Immunol Immunother, 54:424-430, DOI 10.1007/s00262-004-0584-y.

Kirnarsky et al., "Structural analysis of peptide substrates for O-glycosylation," pp. 713-714.

Kjeldsen et al., 1988, "Human-Human Hybridomas and Human Monoclonal Antibodies Obtained by Fusion of Lymph Node Lymphocytes from Breast Cancer Patients," Cancer Research, 48:3208-3214.

Kjeldsen et al., 1988, "Preparation and Characterization of Monoclonal Antibodies Directed to the Tumor-associated O-linked Sialosyl-2→6 α-N-Acetylgalactosaminyl (Sialosyl-Tn) Epitope," Cancer Research, 48:2214-2220.

Klein et al., 2016, "The use of CrossMAb technology for the generation of bi- and multispecific antibodies," mAbs, 8(6):1010-1020, DOI: 10.1080/19420862.2016.1197457.

Labrijn et al., 2013, "Efficient generation of stable bispecific IgG1 by controlled Fab-arm exchange," PNAS, 110(13):5145-5150.

Liu et al., 2017, "Fc Engineering for Developing Therapeutic Bispecific Antibodies and Novel Scaffolds," Frontiers in Immunology, 8(38): 1-15, doi: 10.3389/fimmu.2017.00038.

Marcos et al., 2004, "Role of the Human ST6GalNAc-I and ST6GalNAc-II in the Synthesis of the Cancer-Associated Sialyl-Tn Antigen," Cancer Research, 64:7050-7057.

Matsushita et al., 2014, "A straightforward protocol for the preparation of high performance microarray displaying synthetic MUC1 glycopeptides," Biochimica et Biophysica Acta, 1840:1105-1116.

Mensdorff-Pouilly et al., 2000, "Reactivity of Natural and Induced Human Antibodies to MUC1 Mucin With MUC1 Peptides and N-Acetylgalactosamine (GalNAc) Peptides," Int. J. Cancer, 86:702-712.

Nishimori et al., 1994, "Influence of Acceptor Substrate Primary Amino Acid Sequence on the Activity of Human UDP-N-acetylgalactosamine:Polypeptide N-Acetylgalactosaminyltransferase," The Journal of Biological Chemistry, 269(23): 16123-16130.

Škrlec et al., 2015, "Non-immunoglobulin scaffolds: a focus on their targets," Trends in Biotechnology, 33(7):408-418.

Sørensen et al., 2006, "Chemoenzymatically synthesized multimeric Tn/STn MUC1 glycopeptides elicit cancer-specific anti-MUC1 antibody responses and override tolerance," Glycobiology, 16(2):96-107.

Takeuchi et al., 2002, "The epitope recognized by the unique anti-MUC1 monoclonal antibody MY.1E12 involves sialylα2-3galactosylβ1-3N-acetylgalactosaminide linked to a distinct threonine residue in the MUC1 tandem repeat," Journal of Immunological Methods, 270:199-209.

Tarp et al., 2007, "Identification of a novel cancer-specific immunodominant glycopeptide epitope in the MUC1 tandem repeat," Glycobiology 17(2):197-209.

Taylor-Papadimitriou et al., 1999, "Review—MUC1 and cancer," Biochimica et Biophysica Acta, 1455:301-313.

Thie et al., 2011, "Rise and Fall of an Anti-MUC1 Specific Antibody," PLos ONE, 6(1):e15921.

Yang et al., 2017, "Bispecific Antibodies as a Development Platform for New Concepts and Treatment Strategies," Int. J. Mol. Sci., 18(48): 1-21; doi: 10.3390/ijms18010048.

Zhukovsky et al., 2016, "Bispecific antibodies and CARs: generalized immunotherapeutics harnessing T cell redirection," Current Opinion in Immunology, 40:24-35.

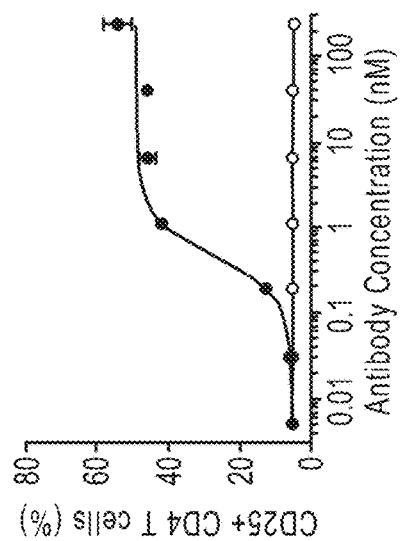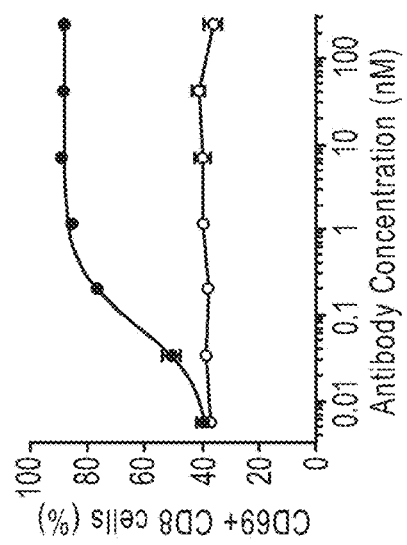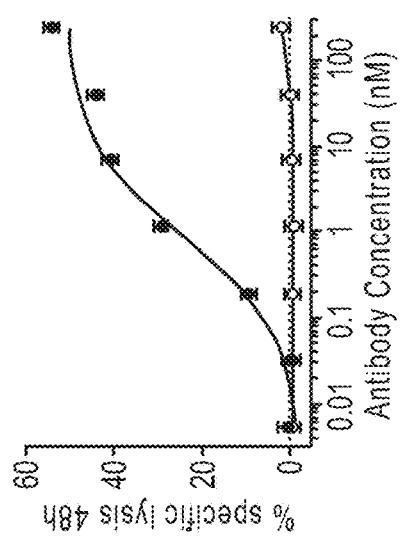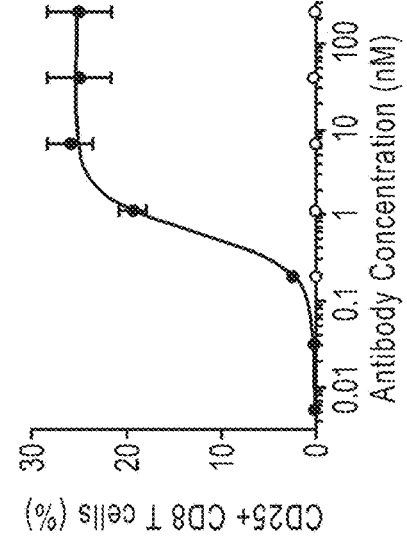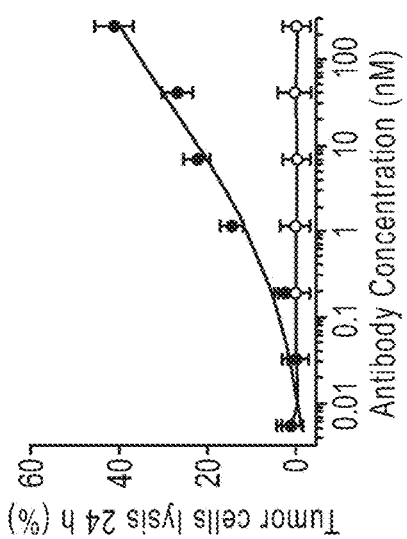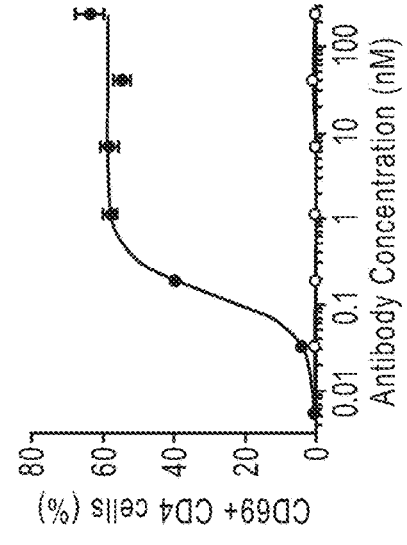

ANTI-GLYCO-MUC1 ANTIBODIES AND THEIR USES

1. CROSS-REFERENCE TO RELATED APPLICATIONS

This application is a division of U.S. application Ser. No. 16/168,259, filed Oct. 23, 2018, now U.S. Pat. No. 11,161, 911, issued Nov. 2, 2021, which claims the benefit of U.S. provisional application Nos. 62/575,666, filed Oct. 23, 2017, and 62/576,297, filed Oct. 24, 2017, the contents of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Nov. 30, 2021 is named GOT-001US_Sequence_Listing.txt GOT-001D1 Sequence Listing.txt and is 34,740 bytes in size.

3. BACKGROUND

The human mucin MUC1 is a polymorphic transmembrane glycoprotein expressed on the apical surfaces of simple and glandular epithelia (Taylor-Papadimitriou et al., 1999). MUC1 is highly overexpressed and aberrantly O-glycosylated in adenocarcinomas. The extracellular domain of the mucin contains variable number of tandem repeats (TRs) (25-125) of 20 amino acid residues with five potential sites for O-glycosylation. O-Glycans are incompletely processed in cancer cells resulting in the expression of the pancarcinoma carbohydrate antigens Tn (GalNAcα1-O-Ser/Thr) (Springer, 1984). Simple mucin-type O-glycans, Tn, are widely expressed in adenocarcinomas (including breast and ovarian cancers) and show limited distribution in normal adult tissues (Springer, 1984). The expression of these O-glycans in cancer correlates with poor prognosis and natural antibodies to these carbohydrate haptens increases in cancer patients (Miles et al., 1995; Soares et al., 1996; Werther et al., 1996). There is a need in the art for therapeutic modalities that utilize glyco-MUC1 epitopes that are overexpressed in cancer cells.

4. SUMMARY

The disclosure captures the tumor specificity of glycopeptide variants by providing therapeutic and diagnostic agents based on antibodies and antigen binding fragments that are selective for cancer-specific epitopes of glyco-MUC1.

The present disclosure provides anti-glyco-MUC1 antibodies and antigen binding fragments thereof that bind to a cancer-specific glycosylation variant of MUC1. The present disclosure further provides fusion proteins and antibody-drug conjugates comprising anti-glyco-MUC1 antibodies and antigen binding fragments, and nucleic acids encoding the anti-glyco-MUC1 antibodies, antigen binding fragments and fusion proteins.

The present disclosure further provides methods of using the anti-glyco-MUC1 antibodies, antigen-binding fragments, fusion proteins, antibody-drug conjugates and nucleic acids for cancer therapy.

In certain aspects, the disclosure provides bispecific and other multispecific anti-glyco-MUC1 antibodies and antigen binding fragments that bind to a cancer-specific glycosylation variant of MUC1 and to a second epitope. The second epitope can either be on MUC1 itself, on another protein co-expressed on cancer cells with MUC1, or on another protein presented on a different cell, such as an activated T cell. Further, also disclosed are nucleic acids encoding such antibodies, including nucleic acids comprising codon-optimized coding regions and nucleic acids comprising coding regions that are not codon-optimized for expression in a particular host cell.

The anti-glyco-MUC1 antibodies and binding fragments can be in the form of fusion proteins containing a fusion partner. The fusion partner can be useful to provide a second function, such as a signaling function of the signaling domain of a T cell signaling protein, a peptide modulator of T cell activation or an enzymatic component of a labeling system. Exemplary T cell signaling proteins include 4-1BB, CO3C, and fusion peptides, e.g., CD28-CD3-zeta and 4-IBB-CD3-zeta. 4-1BB, or CD137, is a co-stimulatory receptor of T cells; CD3-zeta is a signal-transduction component of the T-cell antigen receptor. The moiety providing a second function can be a modulator of T cell activation, such as IL-15, IL-15Ra, or an IL-15/IL-15Ra fusion, or it can encode a label or an enzymatic component of a labeling system useful in monitoring the extent and/or location of binding in vivo or in vitro. Constructs encoding these prophylactically and therapeutically active biomolecules placed in the context of T cells, such as autologous T cells, provide a powerful platform for recruiting adoptively transferred T cells to prevent or treat a variety of cancers in some embodiments of the disclosure.

In certain aspects, an anti-glyco-MUC1 antibody or antigen-binding fragment of the disclosure comprises heavy and/or light chain variable sequences (or encoded by the nucleotide sequences) set forth in Table 1. For clarity, when the term "anti-glyco-MUC1 antibody" is used in this document, it is intended to include monospecific and multispecific (including bispecific) anti-glyco-MUC1 antibodies, antigen-binding fragments of the monospecific and multispecific antibodies, and fusion proteins and conjugates containing the antibodies and their antigen-binding fragments, unless the context dictates otherwise. Likewise, when the term when the term "anti-glyco-MUC1 antibody or antigen-binding fragment" is used, it is also intended to include monospecific and multi-specific (including bispecific) anti-glyco-MUC1 antibodies and their antigen-binding fragments, together with fusion proteins and conjugates containing such antibodies and antigen-binding fragments, unless the context dictates otherwise.

In other aspects, an anti-glyco-MUC1 antibody or antigen-binding fragment of the disclosure comprises heavy and/or light chain CDR sequences (or encoded by the nucleotide sequences) set forth in Tables 1-3. The CDR sequences set forth in Table 1 include CDR sequences defined according to the IMGT (Lefranc et al., 2003, Dev Comparat Immunol 27:55-77, Kabat (Kabat et al., 1991, Sequences of Proteins of Immunological Interest, 5th Ed. Public Health Service, National Institutes of Health, Bethesda, Md.), and Chothia (Al-Lazikani et al., 1997, J. Mol. Biol 273:927-948) schemes for defining CDR boundaries. The CDR sequences set forth in Table 2 are the combined regions of overlap for the CDR sequences shown in Table 1, with the IMGT, Kabat and Chothia sequences shown in underlined bold text. The CDR sequences set forth in Table 3 are the common regions of overlap for the CDR sequences shown in Table 1. The framework sequences for such anti-glyco-MUC1 antibody and antigen-binding fragment can be the native murine framework sequences in Table 1 or can be non-native (e.g., humanized or human) framework sequences.

TABLE 1

| Description | Sequence | SEQ ID NO: |
|---|---|---|
| VH amino acid sequence (incl. signal sequence) | MGWSGIFLFFLSVTTGVHSQVQLQQSDAELVKPGASVK ISCKASGYTFTDHAIHWVKQRPEQGLEWIGYFSPGNDD IHYNEKFEGKATLTADKSSSTAYMQLNSLTSEDSAVYF CKRSYDKDFDCWGQGTTLTVSS | 1 |
| VL amino acid sequence (incl. signal sequence) | MVLILLLLWVSGTCGDIVMSQSPSSLGVSVGEKVTMSC KSSQSLLYSTNQKNYQSLLYSTNQKNYLAWYQQKPGQS PKLLIYWVSNRKSGVPDRFTGSGSGTDFTLTISSVKAE DLAVYYCQQYYRYPLTFGAGTKLELK | 2 |
| VH amino acid sequence (predicted mature) | QVQLQQSDAELVKPGASVKISCKASGYTFTDHAIHWVK QRPEQGLEWIGYFSPGNDDIHYNEKFEGKATLTADKSS STAYMQLNSLTSEDSAVYFCKRSYDKDFDCWGQGTTLT VSS | 3 |
| VL amino acid sequence (predicted mature) | DIVMSQSPSSLGVSVGEKVTMSCKSSQSLLYSTNQKNY QSLLYSTNQKNYLAWYQQKPGQSPKLLIYWVSNRKSGV PDRFTGSGSGTDFTLTISSVKAEDLAVYYCQQYYRYPL TFGAGTKLELK | 4 |
| CDR-H1 amino acid sequence (IMGT definition) | GYTFTDHA | 5 |
| CDR-H2 amino acid sequence (IMGT definition) | FSPGNDDI | 6 |
| CDR-H3 amino acid sequence (IMGT definition) | KRSYDKDFDC | 7 |
| CDR-L1 amino acid sequence (IMGT definition) | QSLLYSTNQKNY | 8 |
| CDR-L2 amino acid sequence (IMGT definition) | WVS | 9 |
| CDR-L3 amino acid sequence (IMGT definition) | QQYYRYPLT | 10 |
| VH nucleotide sequence (incl. signal sequence) | ATGGGATGGAGCGGGATCTTTCTCTTCTTCCTGTCAGT AACTACAGGTGTCCACTCCCAGGTTCAGCTGCAGCAGT CTGACGCGGAGTTGGTGAAACCTGGGGCTTCAGTGAAG ATATCCTGCAAGGCTTCTGGCTACACTTTCACTGACCA TGCTATTCACTGGGTGAAGCAGAGGCCTGAACAGGGCC TGGAATGGATTGGATATTTTTCTCCCGGAAATGATGAC ATTCACTACAATGAGAAGTTCGAGGGCAAGGCCACACT GACTGCAGACAAATCCTCCAGCACTGCCTACATGCAGC TCAACAGCCTGACATCTGAAGATTCTGCAGTGTATTTC TGTAAAAGATCTTACGACAAGGACTTTGACTGCTGGGG CCAAGGCACCACTCTCACAGTCTCCTCA | 11 |
| VL nucleotide sequence (incl. signal sequence) | ATGGTTCTTATCTTACTGCTGCTATGGGTATCTGGTAC CTGTGGGGACATTGTGATGTCACAGTCTCCATCCTCCC TAGGTGTGTCAGTTGGAGAGAAGGTTACTATGAGCTGC AAGTCCAGTCAGAGCCTTTTATACAGTACCAATCAAAA GAACTACCTGGCCTGGTACCAGCAGAAACCAGGGCAGT CTCCTAAGTTGCTGATTTACTGGGTATCTAATAGGAAA TCTGGGGTCCCTGATCGCTTCACAGGCAGTGGATCTGG GACAGATTTCACTCTCACCATCAGTAGTGTGAAGGCTG AAGACCTGGCAGTTTATTACTGTCAGCAATATTATAGG TATCCGCTCACGTTCGGTGCTGGGACCAAGCTGGAGCT GAAA | 12 |
| VH nucleotide sequence (excl. signal | CAGGTTCAGCTGCAGCAGTCTGACGCGGAGTTGGTGAA ACCTGGGGCTTCAGTGAAGATATCCTGCAAGGCTTCTG GCTACACTTTCACTGACCATGCTATTCACTGGGTGAAG | 13 |

TABLE 1-continued

| Description | Sequence | SEQ ID NO: |
|---|---|---|
| sequence) | CAGAGGCCTGAACAGGGCCTGGAATGGATTGGATATTT TTCTCCCGGAAATGATGACATTCACTACAATGAGAAGT TCGAGGGCAAGGCCACACTGACTGCAGACAAATCCTCC AGCACTGCCTACATGCAGCTCAACAGCCTGACATCTGA AGATTCTGCAGTGTATTTCTGTAAAAGATCTTACGACA AGGACTTTGACTGCTGGGGCCAAGGCACCACTCTCACA GTCTCCTCA | |
| VL nucleotide sequence (excl. signal sequence) | GACATTGTGATGTCACAGTCTCCATCCTCCCTAGGTGT GTCAGTTGGAGAGAAGGTTACTATGAGCTGCAAGTCCA GTCAGAGCCTTTTATACAGTACCAATCAAAAGAACTAC CTGGCCTGGTACCAGCAGAAACCAGGGCAGTCTCCTAA GTTGCTGATTTACTGGGTATCTAATAGGAAATCTGGGG TCCCTGATCGCTTCACAGGCAGTGGATCTGGGACAGAT TTCACTCTCACCATCAGTAGTGTGAAGGCTGAAGACCT GGCAGTTTATTACTGTCAGCAATATTATAGGTATCCGC TCACGTTCGGTGCTGGGACCAAGCTGGAGCTGAAA | 14 |
| FR-H1 | QVQLQQSDAELVKPGASVKISCKAS | 15 |
| FR-H2 | IHWVKQRPEQGLEWIGY | 16 |
| FR-H3 | HYNEKFEGKATLTADKSSSTAYMQLNSLTSEDSAVYFC | 17 |
| FR-H4 | WGQGTTLTVSS | 18 |
| FR-L1 | DIVMSQSPSSLGVSVGEKVTMSCKSS | 19 |
| FR-L2 | LAWYQQKPGQSPKLLIY | 20 |
| FR-L3 | NRKSGVPDRFTGSGSGTDFTLTISSVKAEDLAVYYC | 21 |
| FR-L4 | FGAGTKLELK | 22 |
| CDR-H1 amino acid sequence (Kabat definition) | DHAIH | 23 |
| CDR-H2 amino acid sequence (Kabat definition) | YFSPGNDDIHYNEKFEG | 24 |
| CDR-H3 amino acid sequence (Kabat definition) | SYDKDFDC | 25 |
| CDR-L1 amino acid sequence (Kabat definition) | KSSQSLLYSTNQKNYLA | 26 |
| CDR-L2 amino acid sequence (Kabat definition) | WVSNRKS | 27 |
| CDR-L3 amino acid sequence (Kabat definition) | QQYYRYPLT | 10 |
| CDR-H1 amino acid sequence (Chothia definition) | GYTFTDH | 28 |
| CDR-H2 amino acid sequence (Chothia definition) | SPGNDD | 29 |

TABLE 1-continued

| Description | Sequence | SEQ ID NO: |
|---|---|---|
| CDR-H3 amino acid sequence (Chothia definition) | SYDKDFDC | 25 |
| CDR-L1 amino acid sequence (Chothia definition) | SQSLLYSTNQKNY | 30 |
| CDR-L2 amino acid sequence (Chothia definition) | WVS | 9 |
| CDR-L3 amino acid sequence (Chothia definition) | YYRYPLT | 31 |

TABLE 2

| Description | Sequence | SEQ ID NO: |
|---|---|---|
| CDR-H1 amino acid sequence (combined overlap) | GYTFTDHAIH (IMGT)<br>GYTFTDHAIH (Kabat)<br>GYTFTDHAIH (Chothia) | 32 |
| CDR-H2 amino acid sequence (combined overlap) | YFSPGNDDIHYNEKFEG (IMGT)<br>YFSPGNDDIHYNEKFEG (Kabat)<br>YFSPGNDDIHYNEKFEG (Chothia) | 24 |
| CDR-H3 amino acid sequence (combined overlap) | KRSYDKDFDC (IMGT)<br>KRSYDKDFDC (Kabat)<br>KRSYDKDFDC (Chothia) | 7 |
| CDR-L1 amino acid sequence (combined overlap) | KSSQSLLYSTNQKNYLA (IMGT)<br>KSSQSLLYSTNQKNYLA (Kabat)<br>KSSQSLLYSTNQKNYLA (Chothia) | 26 |
| CDR-L2 amino acid sequence (combined overlap) | WVSNRKS (IMGT)<br>WVSNRKS (Kabat)<br>WVSNRKS (Chothia) | 27 |
| CDR-L3 amino acid sequence (combined overlap) | QQYYRYPLT (IMGT)<br>QQYYRYPLT (Kabat)<br>QQYYRYPLT (Chothia) | 10 |

TABLE 3

| Description | Sequence | SEQ ID NO: |
|---|---|---|
| CDR-H1 amino acid sequence (common sequence) | DH | 33 |
| CDR-H2 amino acid sequence (common sequence) | SPGNDD | 29 |
| CDR-H3 amino acid sequence (common sequence) | SYDKDFDC | 25 |
| CDR-L1 amino acid sequence (common sequence) | QSLLYSTNQKNY | 8 |
| CDR-L2 amino acid sequence (common sequence) | WVS | 9 |
| CDR-L3 amino acid sequence (common sequence) | YYRYPLT | 31 |

In certain aspects, the disclosure provides an anti-glyco-MUC1 antibody or antigen-binding fragment of the disclosure comprises CDRs comprising the amino acid sequences of any of the CDR combinations set forth in numbered embodiments 3 to 17. Thus, in certain embodiments, an anti-glyco-MUC1 antibody or antigen-binding fragment of the disclosure comprises a CDR-H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31. In some embodiments, CDR-H1 comprises the amino acid sequence of SEQ ID NO: 5, 23, 28, or 32. In some embodiments, CDR-H2 comprises the amino acid sequence of SEQ ID NO: 6 or 24. In some embodiments, CDR-H3 comprises the amino acid sequence of SEQ ID NO: 7. In some embodiments, CDR-L1 comprises the amino acid sequence of SEQ ID NO:30 or 26. In some embodiments, CDR-L2 comprises the amino acid sequence of SEQ ID NO:27. In some embodiments, CDR- L3 comprises the amino acid sequence of SEQ ID NO:10. In other aspects, an anti-glyco-MUC1 antibody or antigen-binding fragment of the disclosure comprises heavy chain CDRs of SEQ ID NOS: 5-7 and light chain CDRs of SEQ ID NOS: 8-10. In other aspects, an anti-glyco-MUC1 antibody or antigen-binding fragment of the disclosure comprises heavy chain CDRs of SEQ ID NOS: 23-25 and light chain CDRs of SEQ ID NOS: 26, 27, and 10. In other aspects, an anti-glyco-MUC1 antibody or antigen-binding fragment of the disclosure comprises heavy chain CDRs of SEQ ID NOS: 28, 29, and 25 and light chain CDRs of SEQ ID NOS: 30, 9, and 31. In other aspects, an anti-glyco-MUC1 antibody or antigen-binding fragment of the disclosure comprises heavy chain CDRs of SEQ ID NOS: 32, 24, and 7 and light chain CDRs of SEQ ID NOS: 26, 27, and 10. In other aspects, an anti-glyco-MUC1 antibody or antigen-binding fragment of the disclosure comprises heavy chain CDRs of SEQ ID NOS: 33, 29, and 25 and light chain CDRs of SEQ ID NOS: 8, 9, and 31. The antibody or antigen-binding fragment can be murine, chimeric, humanized or human.

In further aspects, an anti-glyco-MUC1 antibody or antigen binding fragment of the disclosure competes with an antibody or antigen binding fragment comprising heavy and light chain variable regions of SEQ ID NOS: 3 and 4, respectively. In yet other aspects, the disclosure provides an anti-MUC1 antibody or antigen binding fragment having heavy and light chain variable regions having at least 95%, 98%, 99%, or 99.5% sequence identity of SEQ ID NOS: 3 and 4, respectively.

In yet other aspects, an anti-glyco-MUC1 antibody or antigen-binding fragment of the disclosure is a single-chain variable fragment (scFv). An exemplary scFv comprises the heavy chain variable fragment N-terminal to the light chain variable fragment. In some embodiments, the scFv heavy chain variable fragment and light chain variable fragment are covalently bound to a linker sequence of 4-15 amino acids. The scFv can be in the form of a bi-specific T-cell engager or within a chimeric antigen receptor (CAR).

The anti-glyco-MUC1 antibodies and antigen-binding fragments can be in the form of a multimer of a single-chain variable fragment, a bispecific single-chain variable fragment and a multimer of a bispecific single-chain variable fragment. In some embodiments, the multimer of a single chain variable fragment is selected a divalent single-chain variable fragment, a tribody or a tetrabody. In some of these embodiments, the multimer of a bispecific single-chain variable fragment is a bispecific T-cell engager.

Other aspects of the disclosure are drawn to nucleic acids encoding the anti-glyco-MUC1 antibodies and antibody-binding fragments of the disclosure. In some embodiments, the portion of the nucleic acid nucleic acid encoding an anti-glyco-MUC1 antibody or antigen-binding fragment is codon-optimized for expression in a human cell. In certain aspects, the disclosure provides an anti-glyco-MUC1 antibody or antigen binding fragment having heavy and light chain variable regions encoded by a heavy chain nucleotide sequence having at least 95%, 98%, 99%, or 99.5% sequence identity to SEQ ID NO:11 or SEQ ID NO:13 and a light chain nucleotide sequence having at least 95%, 98%, 99%, or 99.5% sequence identity to SEQ ID NO:12 or SEQ ID NO:14. Vectors (e.g., a viral vector such as a lentiviral vector) and host cells comprising the nucleic acids are also within the scope of the disclosure. The heavy and light chains coding sequences can be present on a single vector or on separate vectors.

Yet another aspect of the disclosure is a pharmaceutical composition comprising an anti-glyco-MUC1 antibody, antigen-binding fragment, nucleic acid (or pair of nucleic acids), vector (or pair or vectors) or host cell according to the disclosure, and a physiologically suitable buffer, adjuvant or diluent.

Still another aspect of the disclosure is a method of making a chimeric antigen receptor comprising incubating a cell comprising a nucleic acid or a vector according to the disclosure, under conditions suitable for expression of the coding region and collecting the chimeric antigen receptor.

Another aspect of the disclosure is a method of detecting cancer comprising contacting a cell or tissue sample with an anti-glyco-MUC1 antibody or antigen-binding fragment of the disclosure and detecting whether the antibody is bound to the cell or tissue sample.

Yet another aspect of the disclosure is a method of treating cancer comprising administering a prophylactically or therapeutically effective amount of an anti-glyco-MUC1 antibody, antigen-binding fragment, nucleic acid, vector, host cell or pharmaceutical composition according to the disclosure to a subject in need thereof.

5. BRIEF DESCRIPTION OF THE FIGURES

FIG. 1: Results of ELISA assay showing specificity of binding of GO2 to glyco-MUC1 relative to MUC1.

Figure 2:
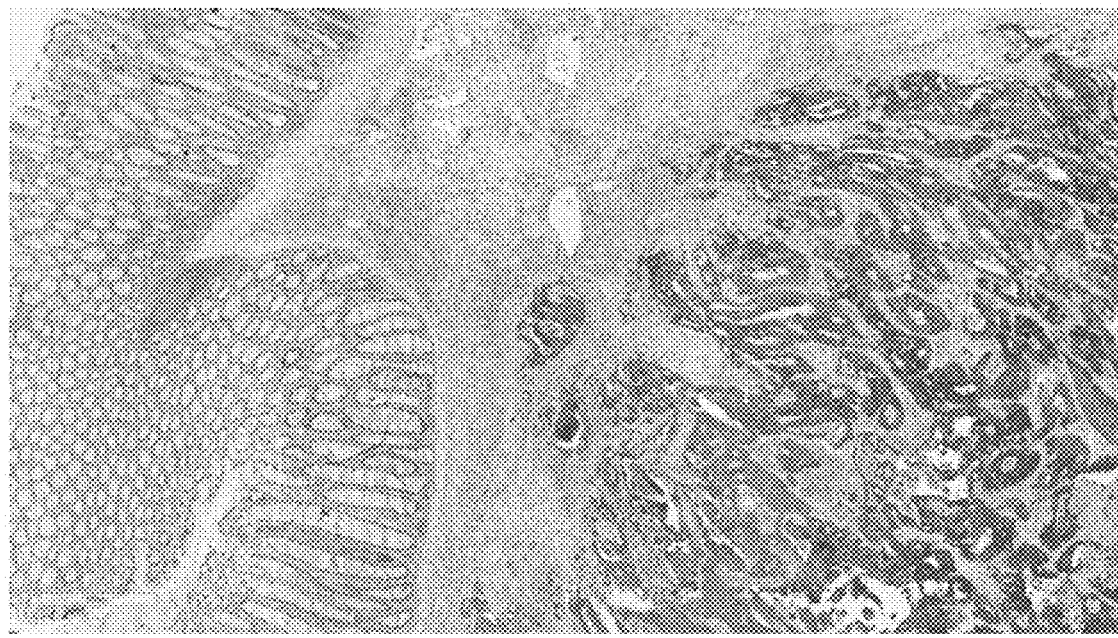

FIG. 2: Binding of GO2 to colon cancer tissue. Immunohistochemistry labeling of invasive colon carcinoma tissue and adjacent healthy tissue using mAbs GO2. mAb GO2 shows distinct binding to colon cancer tissue with high reactivity with both intracellular and surface structures on cancer cells. In contrast no reactivity is seen to surface structures on healthy colon cells.

Figure 3:

FIG. 3: Binding of GO2 to pancreatic cancer tissue. Immunohistochemistry labeling of pancreatic cancer tissue using mAbs GO2. mAb GO2 show distinct binding to pancreatic cancer cells. In contrast no or limited reactivity is seen to surrounding healthy tissue.

Figure 4:
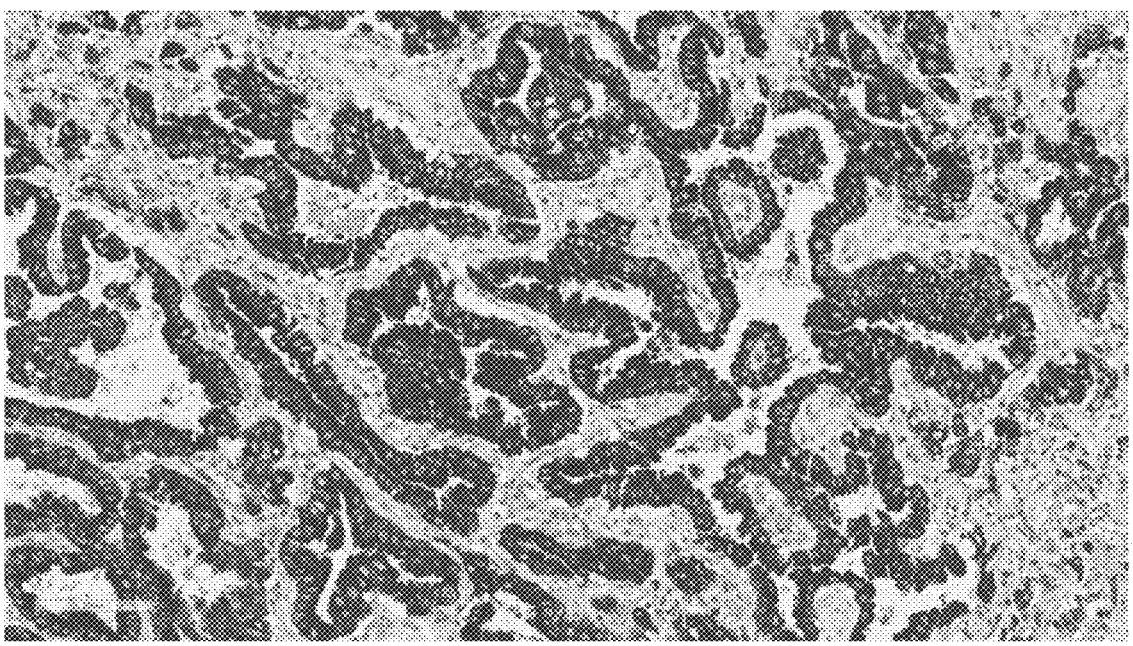

FIG. 4: Binding of GO2 to breast cancer tissue. Immunohistochemistry labeling of breast cancer tissue using mAbs GO2. mAb GO2 showed distinct binding to invasive breast cancer cells.

Figure 5:

FIG. 5: Results of an antibody dependent cellular cytotoxicity assay with antibody GO2 and a secondary antibody conjugated to the antitubulin agent monomethyl auristatin F (MMAF).

Figure 6:
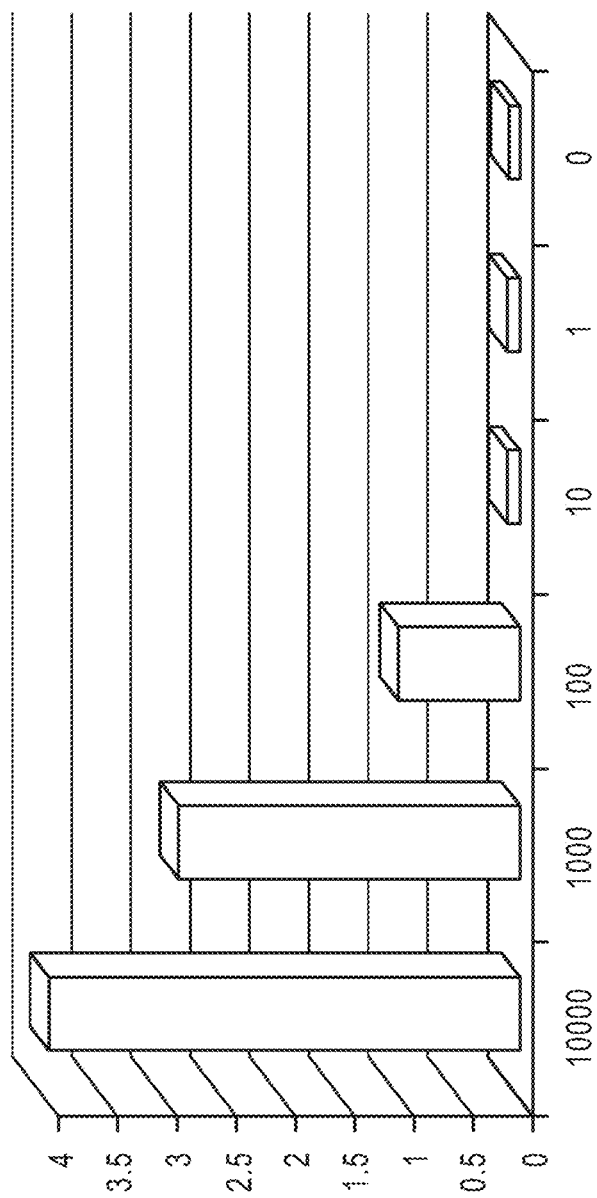

FIG. 6: Results of an ELISA assay quantifying circulating tumor cells using GO2. X-axis shows number of cells and Y-axis shows OD450 values.

Figure 7A:
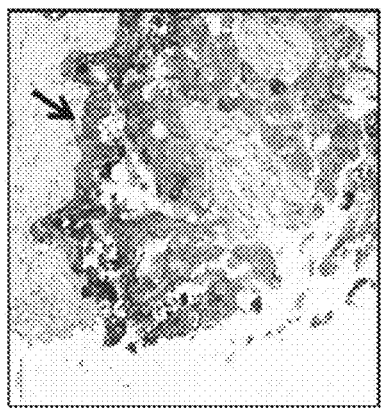
Figure 7B:
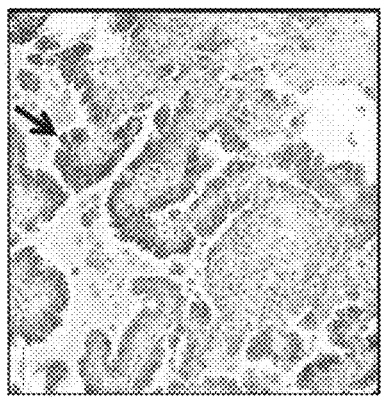
Figure 7C:
Figure 7D:
Figure 7E:
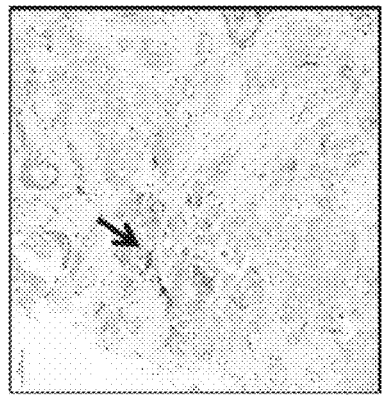

FIGS. 7A-E: Representative images of MUC1 positive TMA tumor cores. FIG. 7A: breast cancer; FIG. 7B: non-small cell lung cancer; FIG. 7C: ovarian cancer; FIG. 7D: colorectal cancer; FIG. 7E: prostate cancer.

Figure 8:
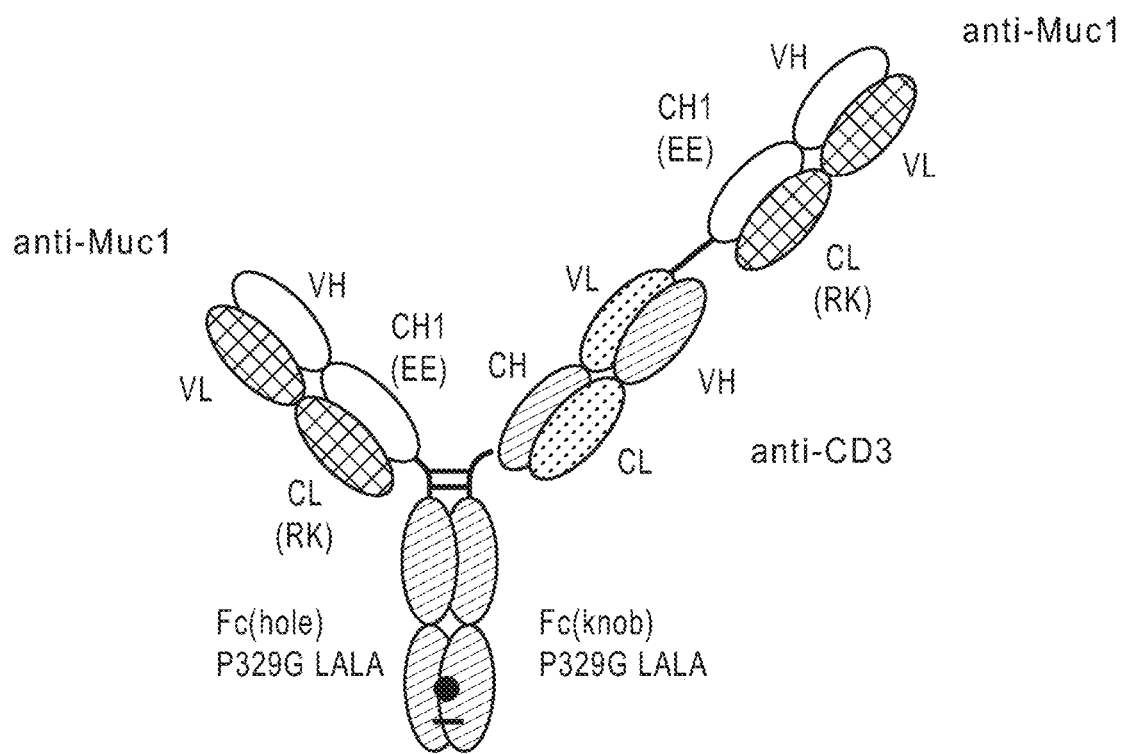

FIG. 8: Schematic of an exemplary anti-glyco-MUC1 and anti-CD3 T-cell bispecific antibody (TCB).

Figure 9A:
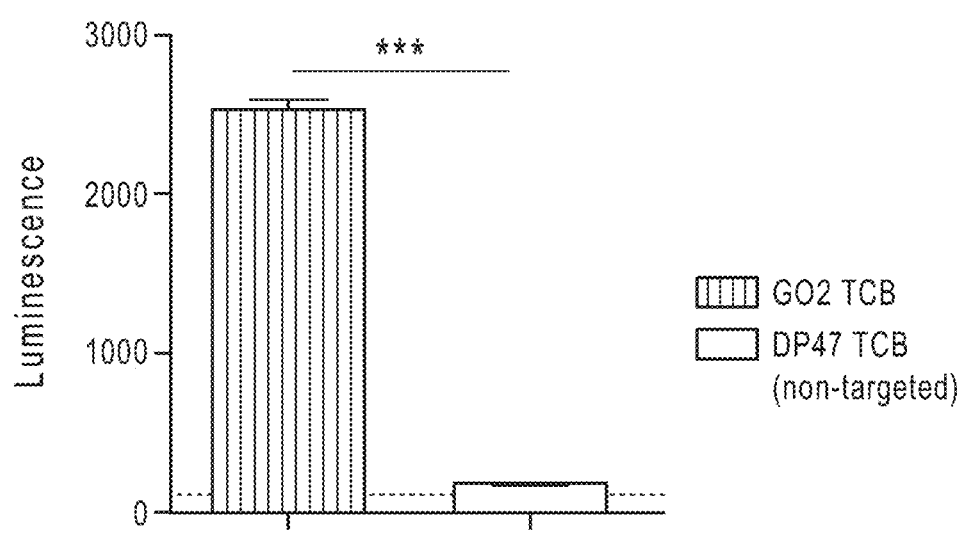
Figure 9B:
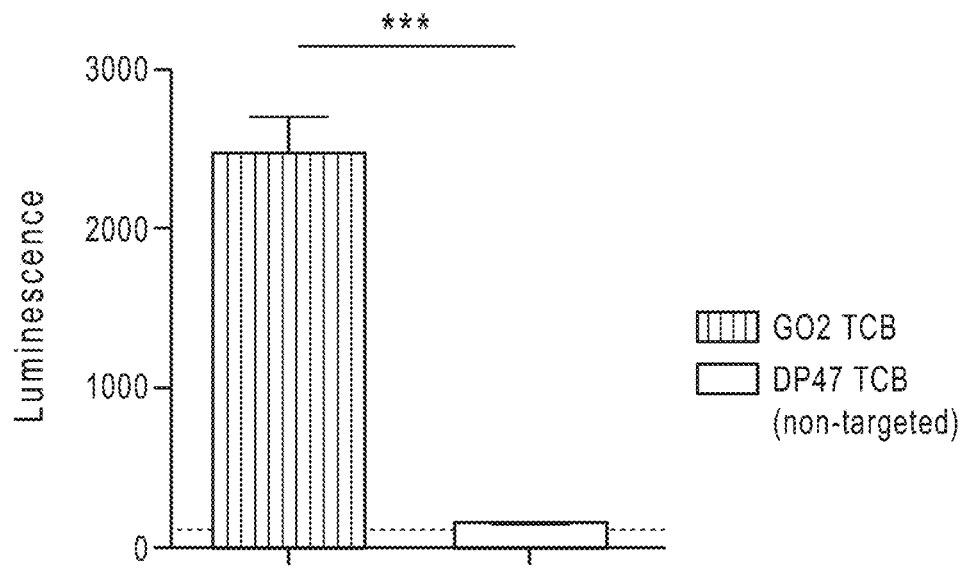

FIGS. 9A-B: Jurkat-NFAT activation assay with undigested patient-derived tumor samples (malignant neoplasm of bronchus and lung: middle lobe, bronchus or lung, squamous cell carcinoma) and different TCBs at 50 nM (FIG. 9A) or 5 nM (FIG. 9B).

Figure 10:
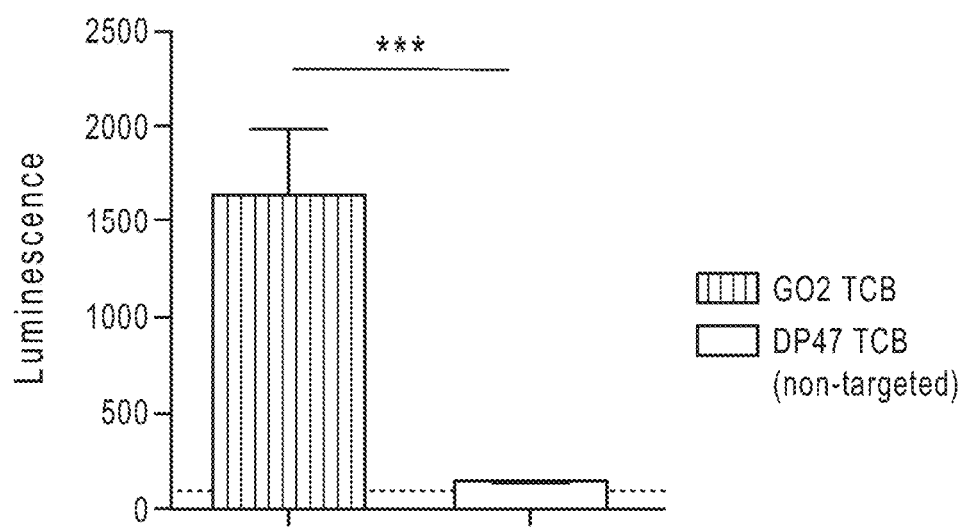

FIG. 10: Jurkat-NFAT activation assay with undigested patient-derived tumor samples (malignant neoplasm of bronchus and lung: lower lobe, bronchus or lung, non-keratinizing squamous cell carcinoma) and different TCBs at 50 nM.

Figure 11:
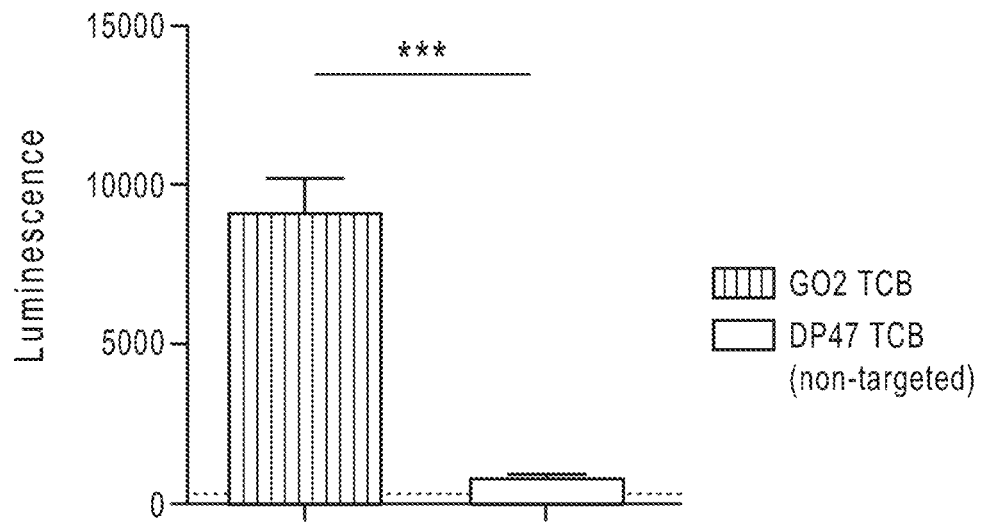

FIG. 11: Jurkat-NFAT activation assay with undigested patient-derived tumor samples (malignant neoplasm of bronchus and lung: upper lobe, bronchus or lung, adenocarcinoma with acinar type) and different TCBs at 50 nM.

Figure 12A:
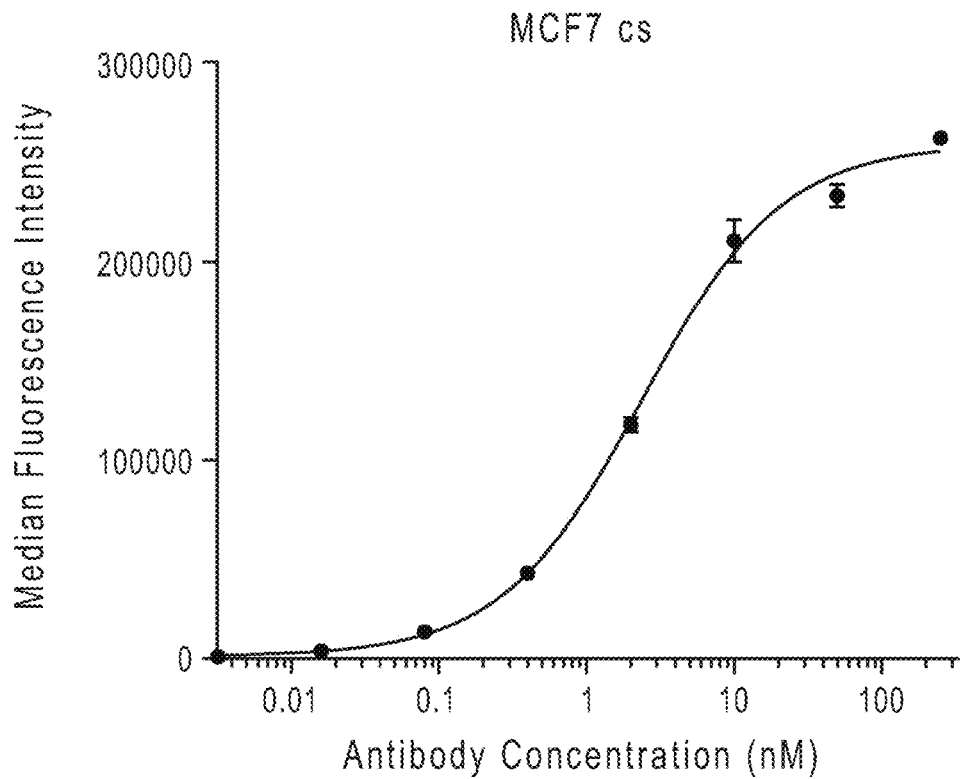
Figure 12B:
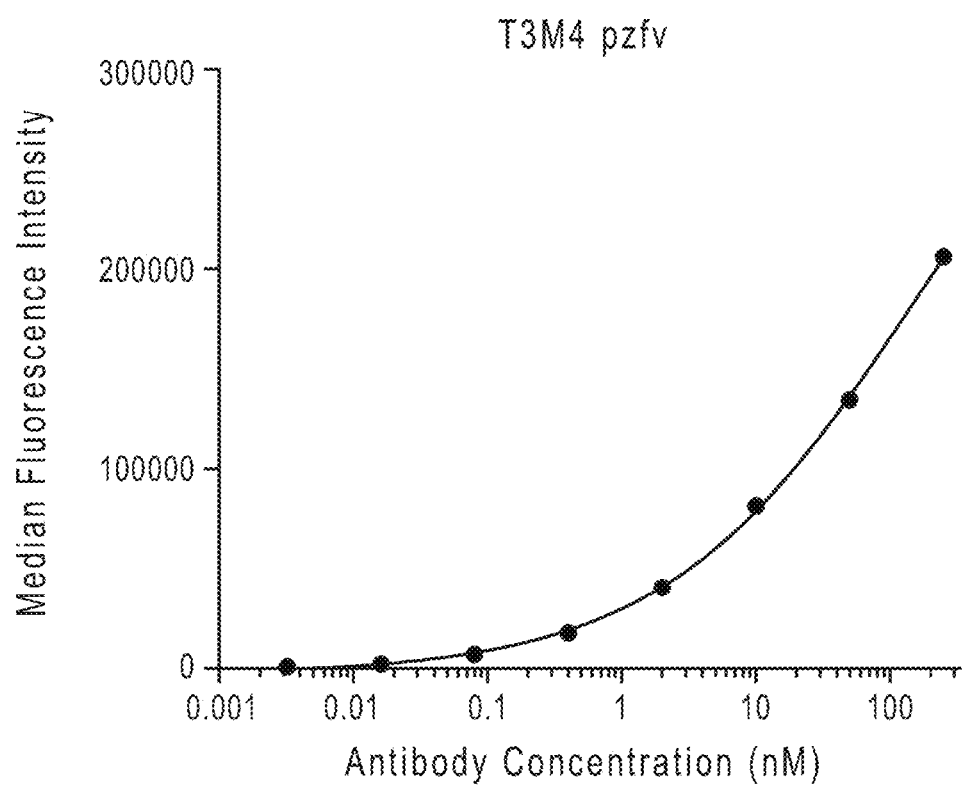

FIGS. 12A-12B: Binding of GO2 TCB to MUC1 expressed on MCF7 cs (FIG. 12A) and T3M4 pzfv (FIG. 12B) cells measured by flow cytometry.

Figure 13C:
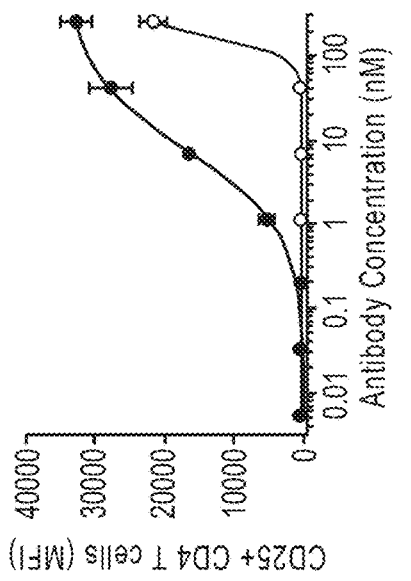
Figure 13B:
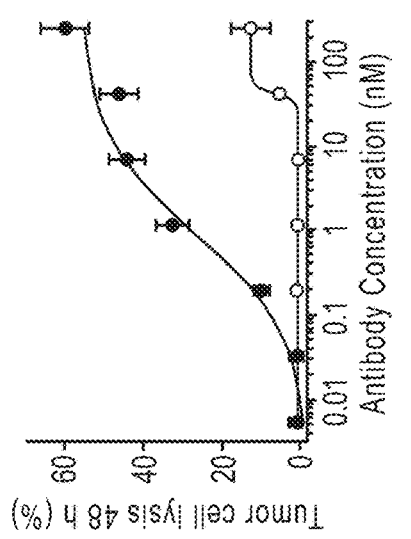
Figure 13A:
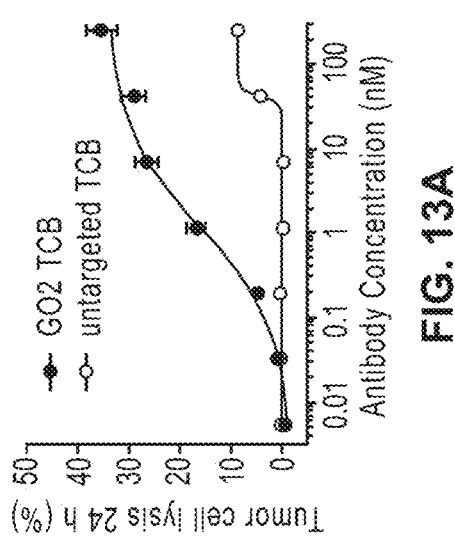
Figure 13F:
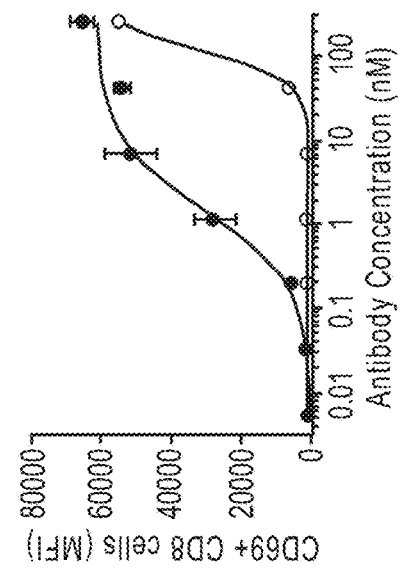
Figure 13E:
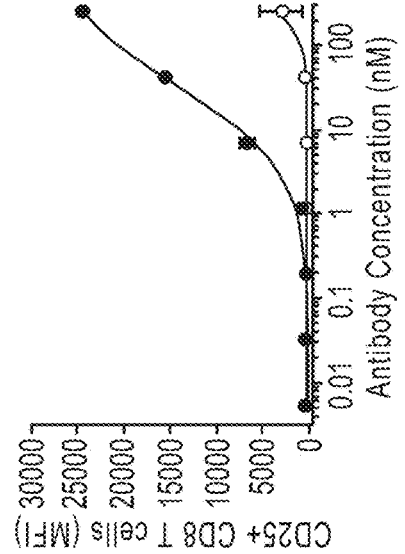
Figure 13D:
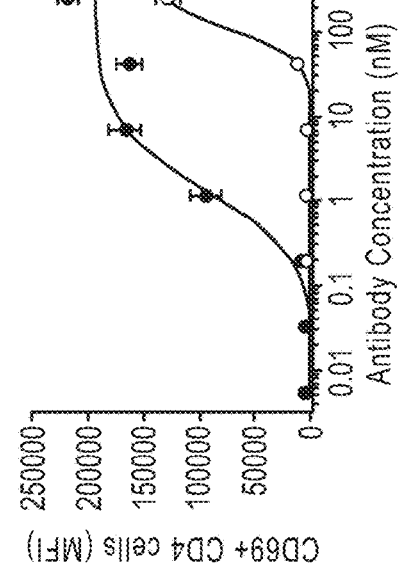
Figure 13G:
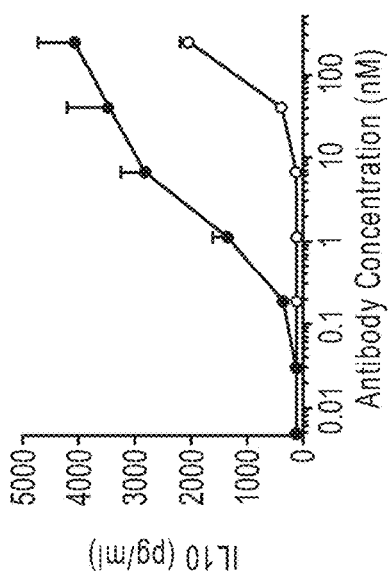
Figure 13H:
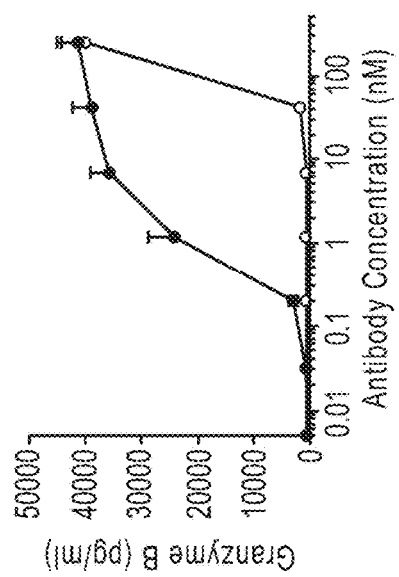
Figure 13I:
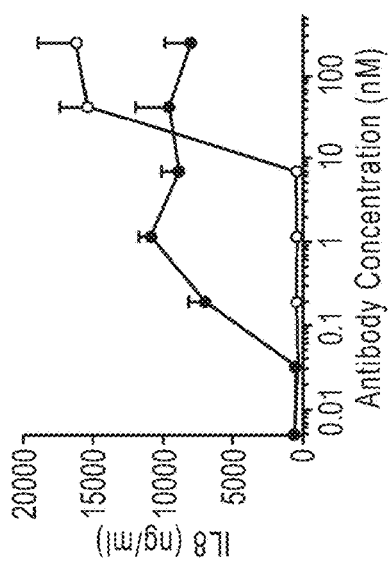
Figure 13J:
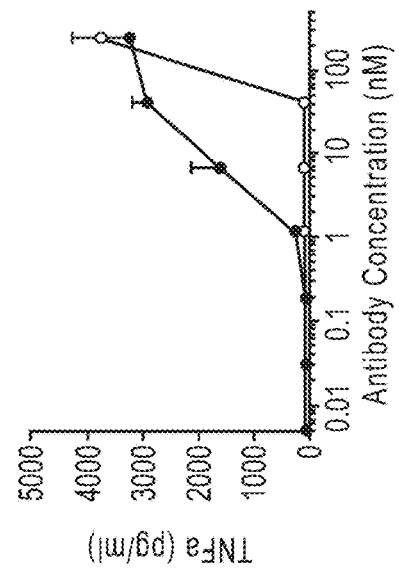
Figure 13K:
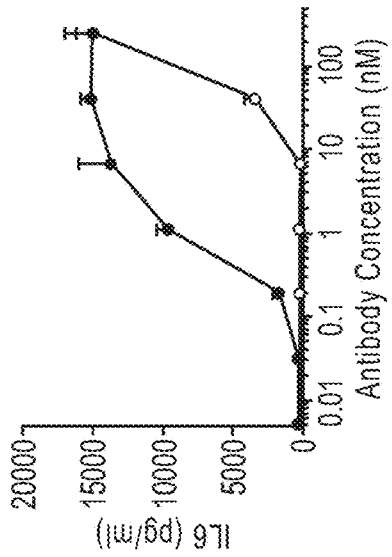
Figure 13L:
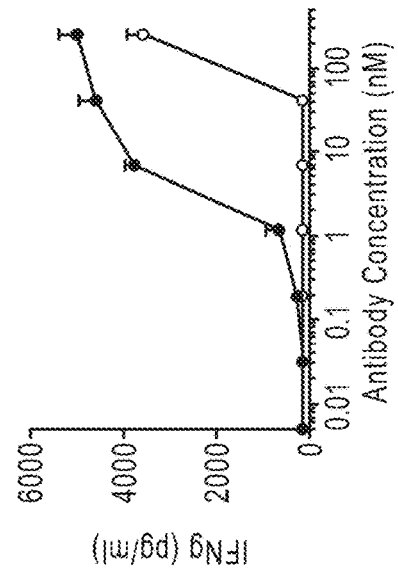
Figure 13S:
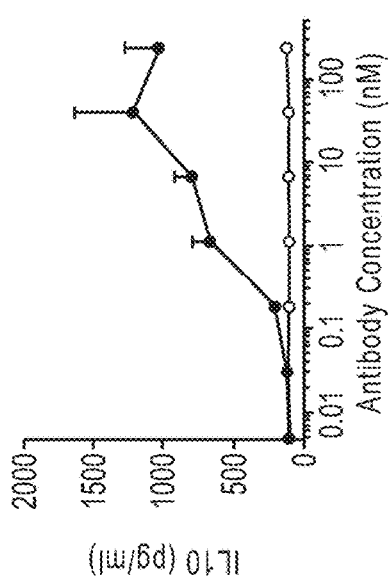
Figure 13T:
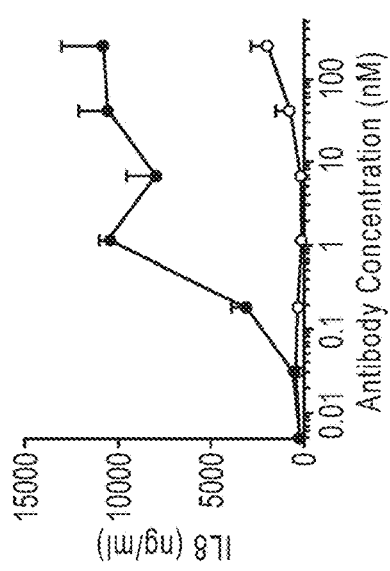
Figure 13U:
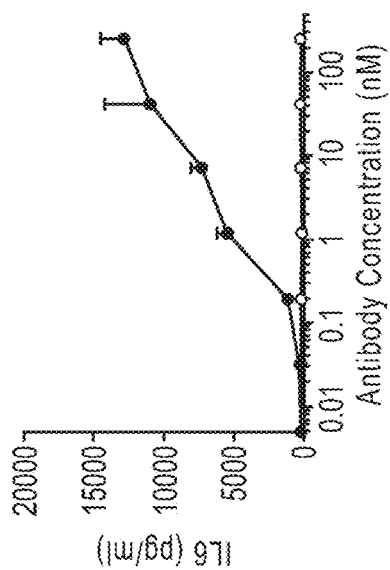
Figure 13V:
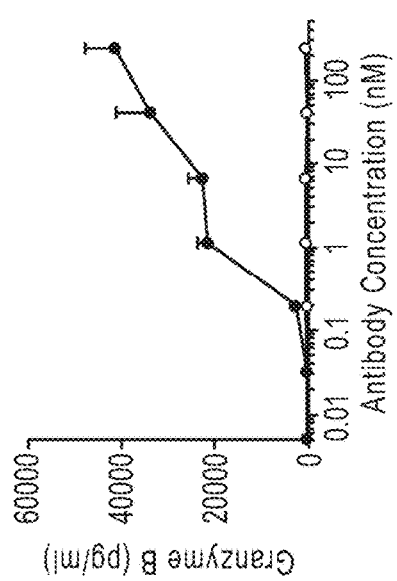
Figure 13W:
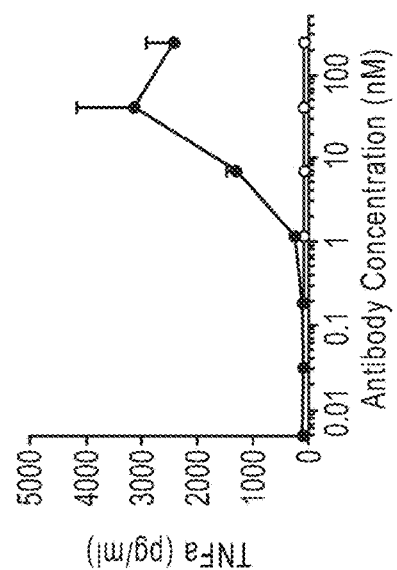
Figure 13X:
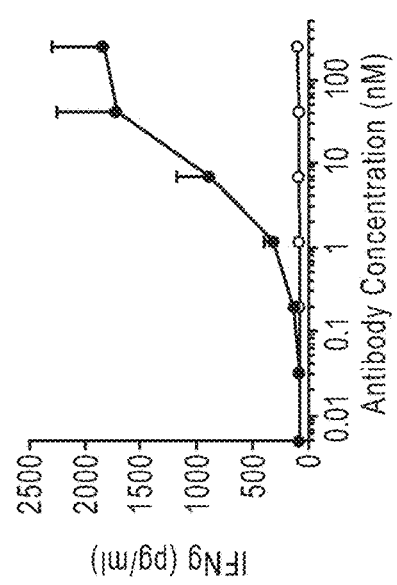
Figure 14A:
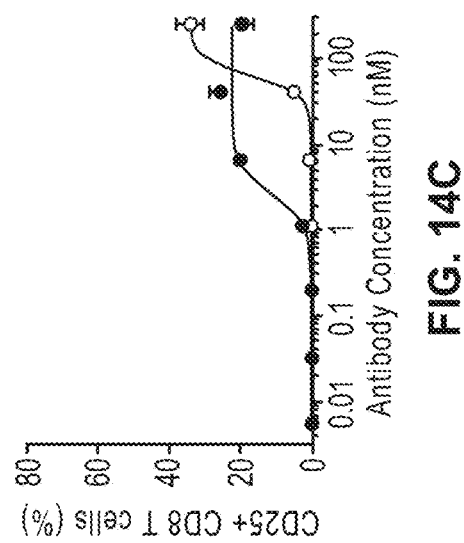
Figure 14B:
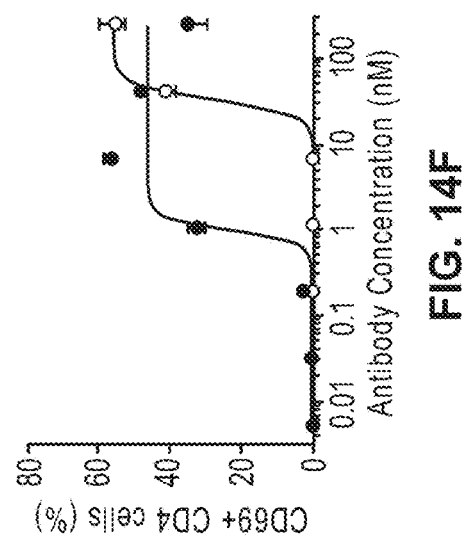
Figure 14C:
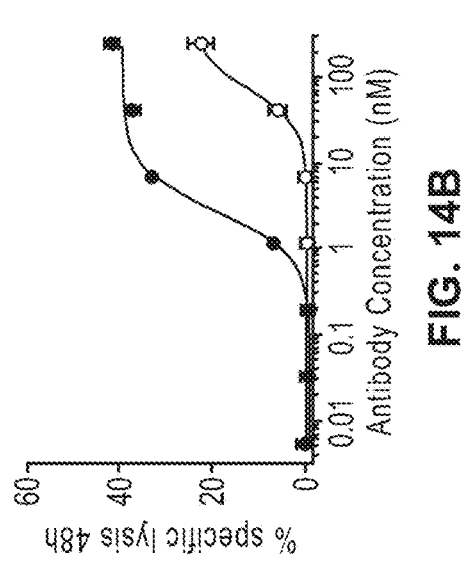
Figure 14D:
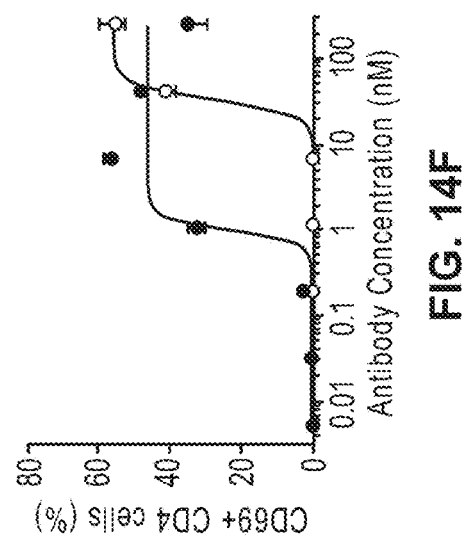
Figure 14E:
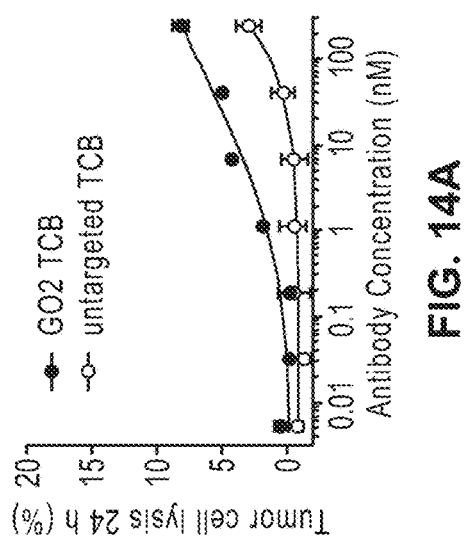
Figure 14F:
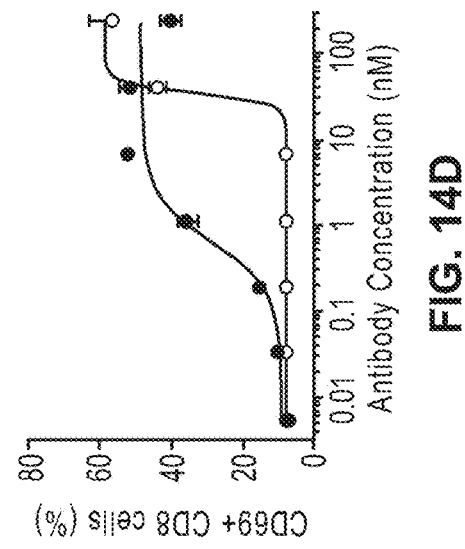

FIGS. 13A-X: Induction of tumor cell killing and T cell activation measured by upregulation of CD25 and CD69 on CD4 T cells and CD8 T cells as well as release of IL6, IL8, IL10, IFNγ, TNFα and Granzyme B with GO2 TCB on T3M4 pzfv in the presence of PBMCs from two healthy donors (donor 1 FIG. 13A-13L; donor 2 FIG. 13M-13X). Same legend for each of FIGS. 13A-13X.

FIGS. 14A-14F: Induction of tumor cell killing (FIGS. 14A-14B) and T cell activation measured by upregulation of CD25 and CD69 on CD8 T cells and CD4 T cells (FIGS. 14C-14F, respectively) with GO2 TCB on MCF7 cs in the presence of PBMCs. Same legend for each of FIGS. 14A-14F.

Figure 15A:
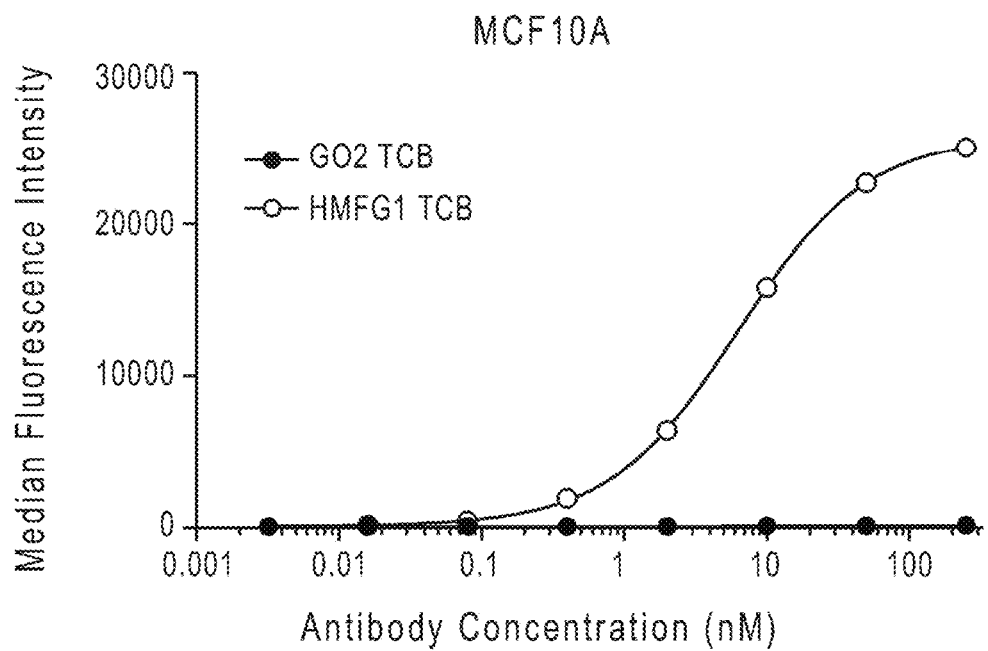
Figure 15B:
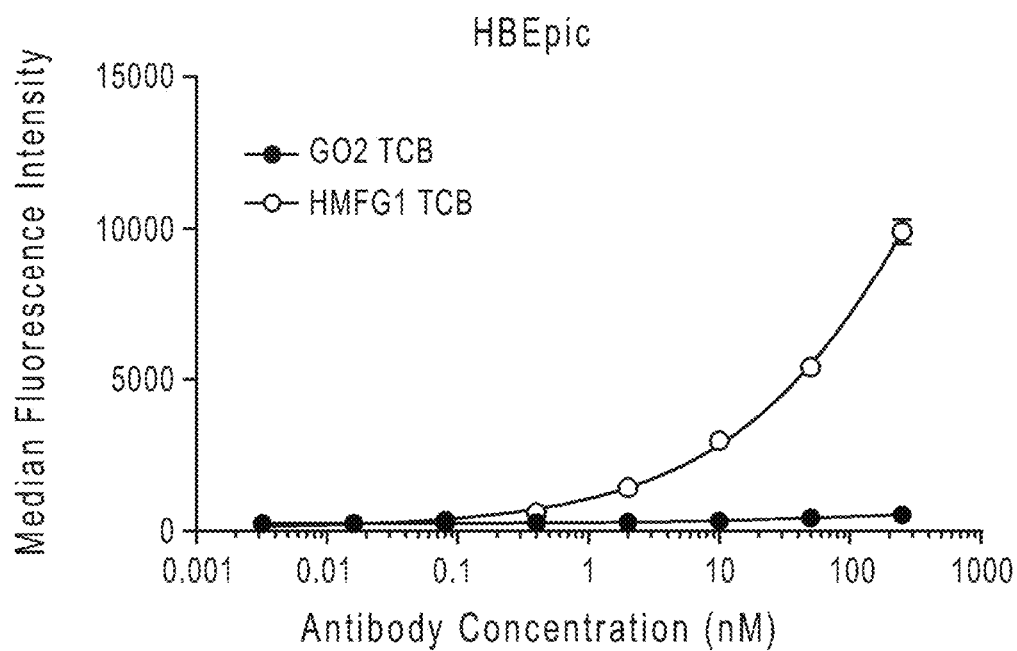

FIG. 15A-B: Binding of GO2 TCB and HMFG1 TCB to MCF10A (human non-tumorigenic mammary epithelial cell line) (FIG. 15A) and HBEpiC (human bronchial epithelial cells) (FIG. 15B).

Figure 16B:
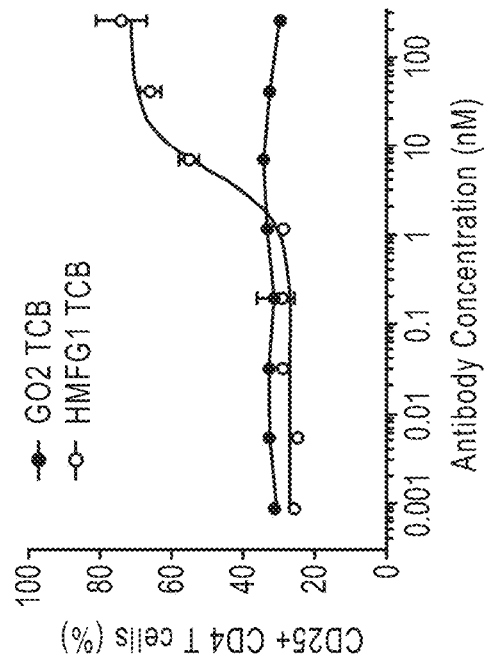
Figure 16C:
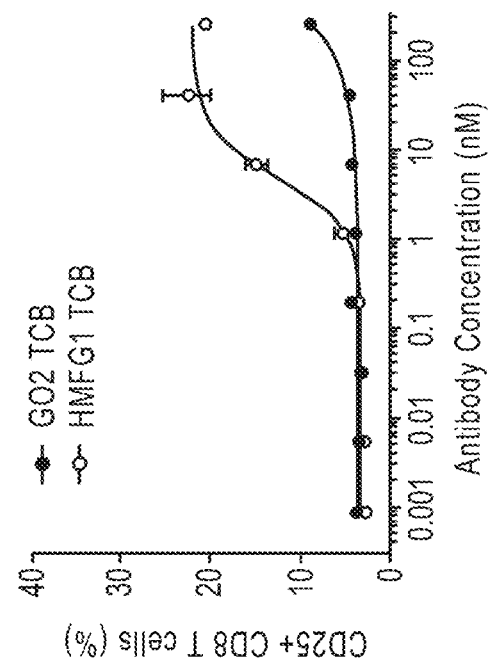
Figure 16A:
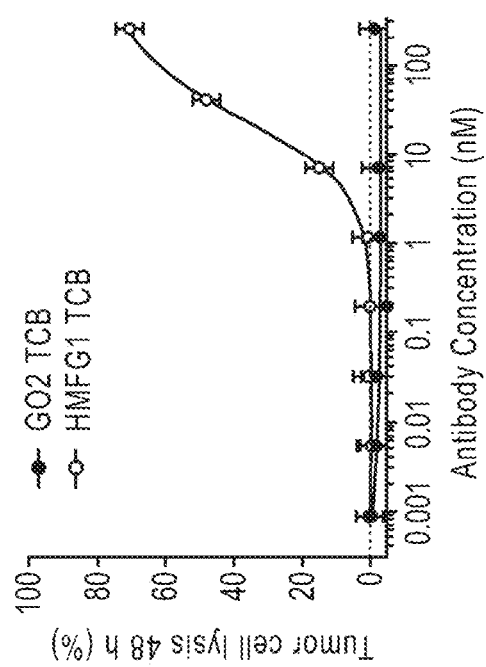

FIG. 16A-C: Induction of tumor cell killing (FIG. 16A) and T cell activation measured by upregulation of CD25 on CD4 T cells (FIG. 16B) and CD8 T cells (FIG. 16C) with GO2 TCB and HMFG1 TCB on MCF10A cells in the presence of PBMCs.

Figure 17:
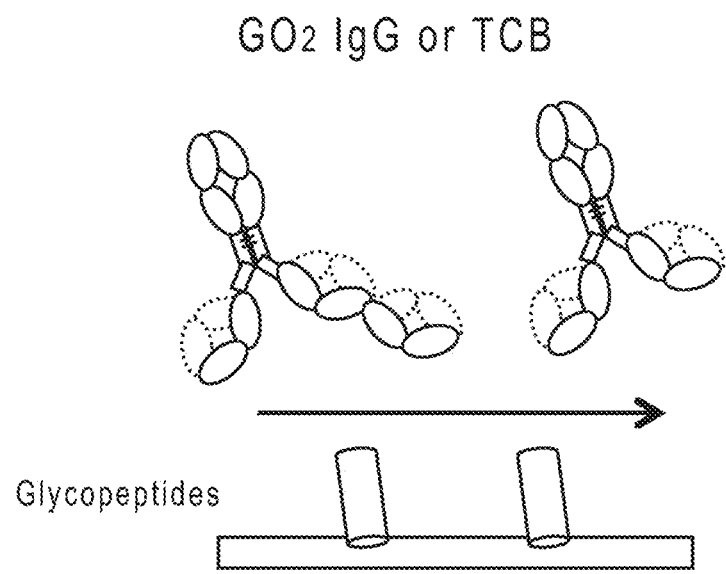

FIG. 17: Illustration of GO2 and GO2 TCB flowing through a flow cell having coupled glycopeptides.

Figure 18A:
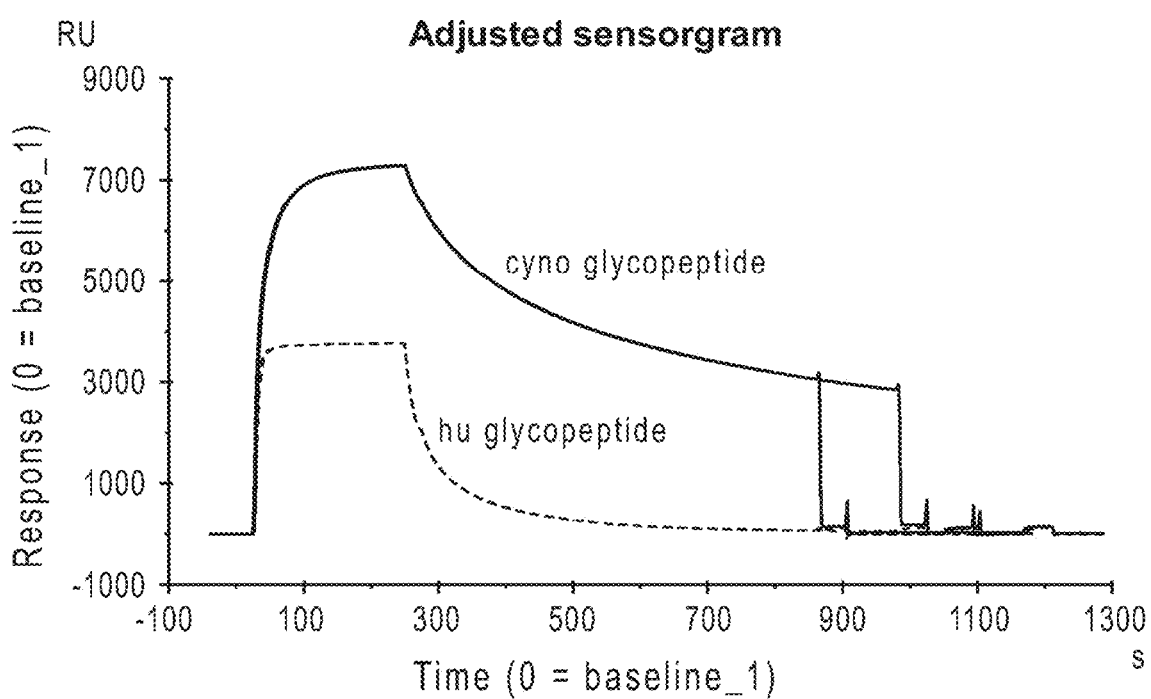
Figure 18B:
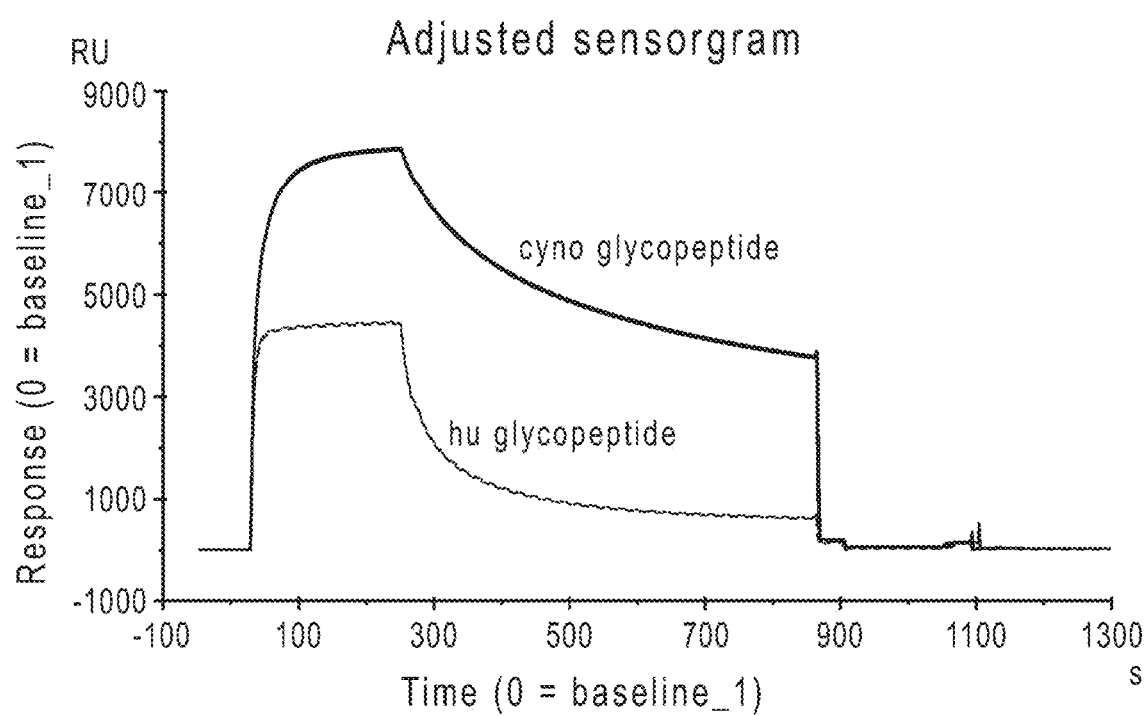

FIG. 18A-B: Sensorgrams showing binding of GO2 (FIG. 18A) and GO2 TCB (FIG. 18B) to human and cynomolgous glycopeptides.

FIG. 19A-D: Binding (avidity) of GO2 antibody (FIG. 19A-19B) and GO2 TCB (FIG. 19C-19D) to human and cynomolgus glycopeptides, and estimate of the "apparent" KD.

6. DETAILED DESCRIPTION

6.1 Antibodies

The inventor has developed novel antibodies that are directed to a glycoform of MUC1 present on tumor cells. These are exemplified by the antibody 5F7, referred to herein as "GO2". GO2 was identified in a screen for antibodies that bind to a glycosylated 60-mer representing 3 copies of one of the tandem repeats present in MUC1, VTSAPDTRPAPGSTAPPAHG (SEQ ID NO:50), glycosylated with purified recombinant human glycosyltransferases polypeptides GalNAc-T2, GalNAc-T4, and GalNAc-T1 so as to mimic the glycosylation pattern of MUC1 present on tumor cells.

The anti-glyco-MUC1 antibodies of the disclosure, exemplified by antibody GO2, are useful as tools in cancer diagnosis and therapy.

Thus, in certain aspects, the disclosure provides antibodies and antigen binding fragments that bind to a glycoform of MUC1 present on tumor cells (referred to herein as "glyco-MUC1"), and preferably to the 60-mer peptide (VT-SAPDTRPAPGSTAPPAHG)$_3$ (SEQ ID NO:47) glycosylated with GalNAc-T2, GalNAc-T4, and GalNAc-T1 as described in U.S. Pat. No. 6,465,220.

The anti-glyco-MUC1 antibodies of the disclosure may be polyclonal, monoclonal, genetically engineered, and/or otherwise modified in nature, including but not limited to chimeric antibodies, humanized antibodies, human antibodies, primatized antibodies, single chain antibodies, bispecific antibodies, dual-variable domain antibodies, etc. In various embodiments, the antibodies comprise all or a portion of a constant region of an antibody. In some embodiments, the constant region is an isotype selected from: IgA (e.g., IgA$_1$ or IgA$_2$), IgD, IgE, IgG (e.g., IgG$_1$, IgG$_2$, IgG$_3$ or IgG$_4$), and IgM. In specific embodiments, the anti-glyco-MUC1 antibodies of the disclosure comprise an IgG$_1$ constant region isotyope.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-glyco-MUC1 antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397, which are incorporated herein by reference in their entireties.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

"Human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

Anti-glyco-MUC1 antibodies of the disclosure include both full-length (intact) antibody molecules, as well as antigen-binding fragments that are capable of binding glyco-MUC1. Examples of antigen-binding fragments include by way of example and not limitation, Fab, Fab', F (ab')$_2$, Fv fragments, single chain Fv fragments and single domain fragments.

A Fab fragment contains the constant domain of the light chain (CL) and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_1$ fragments lack the Fc fragment of intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antigen-binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

"Single domain antibodies" are composed of single $V_H$ or $V_L$ domains which exhibit sufficient affinity to glyco-MUC1. In a specific embodiment, the single domain antibody is a camelized antibody (See, e.g., Riechmann, 1999, Journal of Immunological Methods 231:25-38).

The anti-glyco-MUC1 antibodies of the disclosure may also be bispecific and other multiple specific antibodies. Bispecific antibodies are monoclonal, often human or humanized, antibodies that have binding specificities for two different epitopes on the same or different antigen. In the present disclosure, one of the binding specificities can be directed towards glyco-MUC1, the other can be for any other antigen, e.g., for a cell-surface protein, receptor, receptor subunit, tissue-specific antigen, virally derived protein, virally encoded envelope protein, bacterially derived protein, or bacterial surface protein, etc. In certain preferred embodiments, the bispecific and other multispecific anti-glyco-MUC1 antibodies and antigen binding fragments that specifically bind to a second MUC1 epitope, an epitope on another protein co-expressed on cancer cells with MUC1, or an epitope on another protein presented on a different cell, such as an activated T cell. Bispecific antibodies of the disclosure include IgG format bispecific antibodies and single chain-based bispecific antibodies.

IgG format bispecific antibodies of the disclosure can be any of the various types of IgG format bispecific antibodies known in the art, such as quadroma bispecific antibodies, "knobs-in-holes" bispecific antibodies, CrossMab bispecific antibodies, charge paired bispecific antibodies, common light chain bispecific antibodies, one-arm single-chain Fab-immunoglobulin gamma bispecific antibodies, disulfide stabilized Fv bispecific antibodies, DuetMabs, controlled Fab-arm exchange bispecific antibodies, strand-exchange engineered domain body bispecific antibodies, two-arm leucine zipper heterodimeric monoclonal bispecific antibodies, KA-body bispecific antibodies, dual variable domain bispecific antibodies, and cross-over dual variable domain bispecific antibodies. See, e.g., Köhler and Milstein, 1975, Nature 256:495-497; Milstein and Cuello, 1983, Nature 305:537-40; Ridgway et al., 1996, Protein Eng. 9:617-621; Schaefer et al., 2011, Proc Natl Acad Sci USA 108:11187-92; Gunasekaran et al., 2010, J Biol Chem 285:19637-46; Fischer et al., 2015 Nature Commun 6:6113; Schanzer et al., 2014, J Biol Chem 289:18693-706; Metz et al., 2012 Protein Eng Des Sel 25:571-80; Mazor et al., 2015 MAbs 7:377-89; Labrijn et al., 2013 Proc Natl Acad Sci USA 110:5145-50; Davis et al., 2010 Protein Eng Des Sel 23:195-202; Wranik et al., 2012, J Biol Chem 287:43331-9; Gu et al., 2015, PLoS One 10(5):e0124135; Steinmetz et al., 2016, MAbs 8(5): 867-78; Klein et al., 2016, mAbs, 8(6):1010-1020; Liu et al., 2017, Front. Immunol. 8:38; and Yang et al., 2017, Int. J. Mol. Sci. 18:48, which are incorporated herein by reference in their entireties.

In some embodiments, the bispecific antibodies of the disclosure are CrossMabs. The CrossMab technology is described in detail in WO 2009/080251, WO 2009/080252, WO 2009/080253, WO 2009/080254, WO 2013/026833, WO 2016/020309, and Schaefer et al., 2011, Proc Natl Acad Sci USA 108:11187-92, which are incorporated herein by reference in their entireties. Briefly, the CrossMab technology is based on a domain crossover between heavy and light chains within one Fab-arm of a bispecific IgG, which promotes correct chain association. A CrossMab bispecific antibody of the disclosure can be a "CrossMab$^{FAB}$" antibody, in which the heavy and light chains of the Fab portion of one arm of a bispecific IgG antibody are exchanged. In other embodiments, a CrossMab bispecific antibody of the disclosure can be a "CrossMab$^{VH-VL}$" antibody, in which the only the variable domains of the heavy and light chains of the Fab portion of one arm of a bispecific IgG antibody are exchanged. In yet other embodiments, a CrossMab bispecific antibody of the disclosure can be a "CrossMab$^{CH1-CL}$" antibody, in which only the constant domains of the heavy and light chains of the Fab portion of one arm of a bispecific IgG antibody are exchanged. CrossMab$^{CH1-CL}$ antibodies, in contrast to CrossMab$^{FAB}$ and CrossMab$^{VH-VL}$, do not have predicted side products and, therefore, in some embodiments CrossMab$^{CH1-CL}$ bispecific antibodies are preferred. See, Klein et al., 2016, mAbs, 8(6):1010-1020. Further embodiments of CrossMabs of the disclosure are described below in Section 6.2.

In some embodiments, the bispecific antibodies of the disclosure are controlled Fab-arm exchange bispecific antibodies. Methods for making Fab-arm exchange bispecific antibodies are described in PCT Publication No. WO2011/131746 and Labrijn et al., 2014 Nat Protoc. 9(10):2450-63, incorporated herein by reference in their entireties. Briefly, controlled Fab-arm exchange bispecific antibodies can be made by separately expressing two parental IgG1s containing single matching point mutations in the CH3 domain, mixing the parental IgG1s under redox conditions in vitro to enable recombination of half-molecules, and removing the reductant to allow reoxidation of interchain disulfide bonds, thereby forming the bispecific antibodies.

Bispecific antibodies of the disclosure can comprise an Fc domain composed of a first and a second subunit. In one embodiment, the Fc domain is an IgG Fc domain. In a particular embodiment, the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat EU index numbering), particularly the amino acid substitution S228P. This amino acid substitution reduces in vivo Fab arm exchange of IgG$_4$ antibodies (see Stubenrauch et al., 2010, Drug Metabolism and Disposition 38:84-91). In a further particular embodiment, the Fc domain is a human Fc domain. In an even more particular embodiment, the Fc domain is a human IgG$_1$ Fc domain. An exemplary sequence of a human IgG$_1$ Fc region is given in SEQ ID NO:42.

In particular embodiments, the Fc domain comprises a modification promoting the association of the first and the second subunit of the Fc domain. The site of most extensive protein-protein interaction between the two subunits of a human IgG Fc domain is in the CH3 domain. Thus, in one embodiment said modification is in the CH3 domain of the Fc domain.

In a specific embodiment said modification promoting the association of the first and the second subunit of the Fc domain is a so-called "knob-into-hole" modification, comprising a "knob" modification in one of the two subunits of the Fc domain and a "whole" modification in the other one of the two subunits of the Fc domain. The knob-into-hole technology is described e.g. in U.S. Pat. Nos. 5,731,168; 7,695,936; Ridgway et al., 1996, Prot Eng 9:617-621, and Carter, J, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis. An exemplary substitution is Y470T.

In a specific such embodiment, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numbering according to Kabat EU index). In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second subunit of the Fc domain.

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

Typically, the same one or more amino acid substitution is present in each of the two subunits of the Fc domain. In one embodiment, the one or more amino acid substitution reduces the binding affinity of the Fc domain to an Fc receptor. In one embodiment, the one or more amino acid substitution reduces the binding affinity of the Fc domain to an Fc receptor by at least 2-fold, at least 5-fold, or at least 10-fold.

In one embodiment, the Fc domain comprises an amino acid substitution at a position selected from the group of E233, L234, L235, N297, P331 and P329 (numberings according to Kabat EU index). In a more specific embodiment, the Fc domain comprises an amino acid substitution at a position selected from the group of L234, L235 and P329 (numberings according to Kabat EU index). In some embodiments, the Fc domain comprises the amino acid substitutions L234A and L235A (numberings according to Kabat EU index). In one such embodiment, the Fc domain is an IgG1 Fc domain, particularly a human IgG1 Fc domain. In one embodiment, the Fc domain comprises an amino acid substitution at position P329. In a more specific embodiment, the amino acid substitution is P329A or P329G, particularly P329G (numberings according to Kabat EU index). In one embodiment, the Fc domain comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain comprises amino acid substitutions at positions P329, L234 and L235 (numberings according to Kabat EU index). In more particular embodiments, the Fc domain comprises the amino acid mutations L234A, L235A and P329G (said L234A, L235A and P329G substitutions collectively referred to as "P329G LALA", "PGLALA" or "LALAPG"). Specifically, in particular embodiments, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In one such embodiment, the Fc domain is an IgG1 Fc domain, particularly a human IgG1 Fc domain.

Single chain-based bispecific antibodies of the disclosure can be any of the various types of single chain-based bispecific antibodies known in the art, such as bispecific T-cell engagers (BiTEs), diabodies, tandam diabodies (tandabs), dual-affinity retargeting molecules (DARTs), and bispecific killer cell engagers. See, e.g., Löffler et al., 2000, Blood 95:2098-103; Holliger et al., 1993, Proc Natl Acad Sci USA, 90:6444-8; Kipriyanov et al., 1999, Mol Biol 293:41-56; Johnson et al., 2010, Mol Biol 399:436-49; Wiernik et al., 2013, Clin Cancer Res 19:3844-55; Liu et al., 2017, Front. Immunol. 8:38; and Yang et al., 2017, Int. J. Mol. Sci. 18:48, which are incorporated herein by reference in their entireties.

In some embodiments, the bispecific antibodies of the disclosure are bispecific T-cell engagers (BiTEs). BiTEs are single polypeptide chain molecules that having two antigen-binding domains, one of which binds to a T-cell antigen and the second of which binds to an antigen present on the surface of a target (See, PCT Publication WO 05/061547; Baeuerle et al., 2008, Drugs of the Future 33: 137-147; Bargou, et al., 2008, Science 321:974-977, incorporated herein by reference in their entireties). Thus, the BiTEs of the disclosure have an antigen binding domain that binds to a T-cell antigen, and a second antigen binding domain that is directed towards glyco-MUC1.

In some embodiments, the bispecific antibodies of the disclosure are dual-affinity retargeting molecules (DARTs). DARTs comprise at least two polypeptide chains that associate (especially through a covalent interaction) to form at least two epitope binding sites, which may recognize the same or different epitopes. Each of the polypeptide chains of a DART comprise an immunoglobulin light chain variable region and an immunoglobulin heavy chain variable region, but these regions do not interact to form an epitope binding site. Rather, the immunoglobulin heavy chain variable region of one (e.g., the first) of the DART polypeptide chains interacts with the immunoglobulin light chain variable region of a different (e.g., the second) DART™ polypeptide chain to form an epitope binding site. Similarly, the immunoglobulin light chain variable region of one (e.g., the first) of the DART polypeptide chains interacts with the immunoglobulin heavy chain variable region of a different (e.g., the second) DART polypeptide chain to form an epitope binding site. DARTs may be monospecific, bispecific, trispecific, etc., thus being able to simultaneously bind one, two, three or more different epitopes (which may be of the same or of different antigens). DARTs may additionally be monovalent, bivalent, trivalent, tetravalent, pentavalent, hexavalent, etc., thus being able to simultaneously bind one, two, three, four, five, six or more molecules. These two attributes of DARTs (i.e., degree of specificity and valency may be combined, for example to produce bispecific antibodies (i.e., capable of binding two epitopes) that are tetravalent (i.e., capable of binding four sets of epitopes), etc. DART molecules are disclosed in PCT Publications WO 2006/113665, WO 2008/157379, and WO 2010/080538, which are incorporated herein by reference in their entireties.

In some embodiments of the bispecific antibodies of the disclosure, one of the binding specificities is directed towards glyco-MUC1, and the other is directed to an antigen expressed on immune effector cells. The term "immune effector cell" or "effector cell" as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte. Recruitment of effector cells to aberrant cells means that immune effector cells are brought in close vicinity to the aberrant target cells such that the effector cells can directly kill, or indirectly initiate the killing of the aberrant cells that they are recruited to. In order to avoid non specific interactions it is preferred that the bispecific antibodies of the disclosure specifically recognize antigens on immune effector cells that are at least over-expressed by these immune effector cells compared to other cells in the body. Target antigens present on immune effector cells may include CD3, CD8, CD16, CD25, CD28, CD64, CD89, NKG2D and NKp46. Preferably, the antigen on immune effector cells is CD3 expressed on T cells.

As used herein, "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. The most preferred antigen on an immune effector cell is the CD3 epsilon chain. This antigen has been shown to be very effective in recruiting T cells to aberrant cells. Hence, a bispecific antibody of the disclosure preferably specifically recognizes CD3 epsilon. The amino acid sequence of human CD3 epsilon is shown in UniProt (www.uniprot.org) accession no. P07766 (version 144), or NCBI (www.ncbi.nlm.nih.gov/) RefSeq NP_000724.1. The amino acid sequence of cynomolgus [*Macaca fascicularis*] CD3 epsilon is shown in NCBI GenBank no. BAB71849.1. For human therapeutic use, bispecific antibodies in which the CD3-binding domain specifically binds to human CD3 (e.g., the human CD3 epsilon chain) are used. For preclinical testing in non-human animals and cell lines, bispecific antibodies in which the CD3-binding domain specifically binds to the CD3 in the species utilized for the preclinical testing (e.g., cynomolgus CD3 for primate testing) can be used.

As used herein, a binding domain that "specifically binds to" or "specifically recognizes" a target antigen from a particular species does not preclude the binding to or recognition of the antigen from other species, and thus encompasses antibodies in which one or more of the binding domains have inter-species cross-reactivity. For example, a CD3-binding domain that "specifically binds to" or "specifically recognizes" human CD3 may also bind to or recognize cyomolgus CD3, and vice versa.

In some embodiments, a bispecific antibody of the disclosure can compete with monoclonal antibody H2C (described in PCT publication no. WO2008/119567) for binding an epitope of CD3. In other embodiments, a bispecific antibody of the disclosure can compete with monoclonal antibody V9 (described in Rodrigues et al., 1992, Int J Cancer Suppl 7:45-50 and U.S. Pat. No. 6,054,297) for binding an epitope of CD3. In yet other embodiments, a bispecific antibody of the disclosure can compete with monoclonal antibody FN18 (described in Nooij et al., 1986, Eur J Immunol 19:981-984) for binding an epitope of CD3. In yet other embodiments, a bispecific antibody of the disclosure can compete with monoclonal antibody SP34 (described in Pessano et al., 1985, EMBO J 4:337-340) for binding an epitope of CD3.

The anti-glyco-MUC1 antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

The anti-glyco-MUC1 antibodies or binding fragments may be antibodies or fragments whose sequences have been modified to alter at least one constant region-mediated biological effector function. For example, in some embodiments, an anti-glyco-MUC1 antibody may be modified to reduce at least one constant region-mediated biological effector function relative to the unmodified antibody, e.g., reduced binding to the Fc receptor (FcγR). FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

The anti-glyco-MUC1 antibody or binding fragments described herein include antibodies and/or binding fragments that have been modified to acquire or improve at least one constant region-mediated biological effector function relative to an unmodified antibody, e.g., to enhance FcγR interactions (See, e.g., US 2006/0134709). For example, an anti-glyco-MUC1 antibody of the disclosure can have a constant region that binds FcγRIIA, FcγRIIB and/or FcγRIIIA with greater affinity than the corresponding wild type constant region.

Thus, antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (shown in FIG. 4 of U.S. Pat. No. 5,834,597) in which residue 236 is deleted and residues 234, 235 and 237 (using EU numbering) are substituted with alanines.

In some embodiments, the anti-glyco-MUC1 antibodies of the disclosure have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-glyco-MUC1 antibodies or binding fragments include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-glyco-MUC1 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which is incorporated herein by reference. Such mutations increase binding to FcRn, which protects the antibody from degradation and increases its half-life.

In yet other aspects, an anti-glyco-MUC1 antibody of antigen-binding fragment of the disclosure has one or more amino acids inserted into one or more of its hypervariable regions, for example as described in Jung and Pluckthun, 1997, Protein Engineering 10:9, 959-966; Yazaki et al., 2004, Protein Eng. Des Sel. 17(5):481-9. Epub 2004 Aug. 17; and U.S. Pat. App. No. 2007/0280931.

In yet other aspects, particularly useful for diagnostic applications, an anti-glyco-MUC1 antibody of antigen-binding fragment of the disclosure is attached to a detectable moiety. Detectably moieties include a radioactive moiety, a colorimetric molecule, a fluorescent moiety, a chemiluminescent moiety, an antigen, an enzyme, a detectable bead (such as a magnetic or electrodense (e.g., gold) bead), or a molecule that binds to another molecule (e.g., biotin or streptavidin)).

Radioisotopes or radionuclides may include $^{3}H$, $^{14}C$, $^{15}N$, $^{35}S$, $^{90}Y$, $^{99}Tc$, $^{111}In$, $^{125}I$, $^{131}I$.

Fluorescent labels may include rhodamine, lanthanide phosphors, fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine.

Enzymatic labels may include horseradish peroxidase, β galactosidase, luciferase, alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase.

Chemiluminescent labels or chemiluminescers, such as isoluminol, luminol and the dioxetanes Other detectable moieties include molecules such as biotin, digoxygenin or 5-bromodeoxyuridine.

In certain aspects, an anti-glyco-MUC1 antibody or antigen binding fragment of the disclosure competes with GO2 or an antibody or antigen binding fragment comprising heavy and light chain variable regions of GO2 (SEQ ID NOS:3 and 4, respectively).

The competition can be assayed on cells that express the glyco-MUC1 epitope bound by GO2 or on a glycosylated MUC1 peptide containing the epitope bound by GO2, e.g., the 60-mer peptide (VTSAPDTRPAPGSTAPPAHG)$_3$ (SEQ ID NO:47) glycosylated with GalNAc-T2, GalNAc-T4, and GalNAc-T1 as described in U.S. Pat. No. 6,465,220. Cells that do not express the epitope or unglycosylated peptides can be used as controls.

Cells on which a competition assay can be carried out include but are not limited to the breast cancer cell lines MCF7 or T47D and recombinant cells that are engineered to express the glyco-MUC1 epitope. In one non-limiting example, CHO IdID cells, which lack the UDP-Gal/GalNAc epimerase and are deficient in GalNAc O-glycosylation and galactosylation in the absence of exogenous addition of GalNAc and Gal, respectively, are engineered to express MUC1 and grown in the absence or presence of GalNAc, the latter yielding cells expressing the Tn glycoform of MUC1 to which GO2 binds. Cells expressing the unglycosylated form of MUC1 can be used as a negative control.

Assays for competition include, but are not limited to, a radioactive material labeled immunoassay (RIA), an enzyme-linked immunosorbent assay (ELISA), a sandwich ELISA fluorescence activated cell sorting (FACS) assays and Biacore assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing glyco-MUC1 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("$conc_{80\%}$") under the assay conditions (e.g., a specified density of cells) is first determined, and a competition assay carried out with $10 \times conc_{80\%}$ of unlabeled test antibody and $conc_{80\%}$ of labeled reference antibody.

The inhibition can be expressed as an inhibition constant, or $K_i$, which is calculated according to the following formula:

$$K_i = IC_{50}/(1+[\text{reference Ab concentration}]/K_d),$$

where $IC_{50}$ is the concentration of test antibody that yields a 50% reduction in binding of the reference antibody and $K_d$ is the dissociation constant of the reference antibody, a measure of its affinity for glyco-MUC1. Antibodies that compete with anti-glyco-MUC1 antibodies disclosed herein can have a $K_i$ from 10 pM to 10 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

In one example of a competition assay, the glycosylated MUC1 60-mer peptide is adhered onto a solid surface, e.g., a microwell plate, by contacting the plate with a solution of the peptide (e.g., at a concentration of 1 µg/mL in PBS over night at 4° C.). The plate is washed (e.g., 0.1% Tween 20 in PBS) and blocked (e.g., in Superblock, Thermo Scientific, Rockford, IL). A mixture of sub-saturating amount of biotinylated GO2 (e.g., at a concentration of 80 ng/mL) and unlabeled GO2 (the "reference" antibody) or competing anti-glyco-MUC1 antibody (the "test" antibody) antibody in serial dilution (e.g., at a concentration of 2.8 µg/mL, 8.3 µg/mL, or 25 µg/mL) in ELISA buffer (e.g., 1% BSA and 0.1% Tween 20 in PBS) is added to wells and plates are incubated for 1 hour with gentle shaking. The plate is washed, 1 µg/mL HRP-conjugated Streptavidin diluted in ELISA buffer is added to each well and the plates incubated for 1 hour. Plates are washed and bound antibodies were detected by addition of substrate (e.g., TMB, Biofx Laboratories Inc., Owings Mills, MD). The reaction is terminated by addition of stop buffer (e.g., Bio FX Stop Reagents, Biofx Laboratories Inc., Owings Mills, MD) and the absorbance is measured at 650 nm using microplate reader (e.g., VERSAmax, Molecular Devices, Sunnyvale, CA).

Variations on this competition assay can also be used to test competition between GO2 and another anti-glyco-MUC1 antibody. For example, in certain aspects, the anti-glyco-MUC1 antibody is used as a reference antibody and GO2 is used as a test antibody. Additionally, instead of glycosylated MUC1 60-mer peptide, membrane-bound glyco-MUC1 expressed on cell surface (for example on the surface of one of the cell types mentioned above) in culture can be used. Generally, about $10^4$ to $10^6$ transfectants, e.g., about $10^5$ transfectants, are used. Other formats for competition assays are known in the art and can be employed.

In various embodiments, an anti-glyco-MUC1 antibody of the disclosure reduces the binding of labeled GO2 by at least 40%, by at least 50%, by at least 60%, by at least 70%, by at least 80%, by at least 90%, or by a percentage ranging between any of the foregoing values (e.g., an anti-glyco-MUC1 antibody of the disclosure reduces the binding of labeled GO2 by 50% to 70%) when the anti-glyco-MUC1 antibody is used at a concentration of 0.08 μg/mL, 0.4 μg/mL, 2 μg/mL, 10 μg/mL, 50 μg/mL, 100 μg/mL or at a concentration ranging between any of the foregoing values (e.g., at a concentration ranging from 2 μg/mL to 10 μg/mL).

In other embodiments, GO2 reduces the binding of a labeled anti-glyco-MUC1 antibody of the disclosure by at least 40%, by at least 50%, by at least 60%, by at least 70%, by at least 80%, by at least 90%, or by a percentage ranging between any of the foregoing values (e.g., GO2 reduces the binding of a labeled an anti-glyco-MUC1 antibody of the disclosure by 50% to 70%) when GO2 is used at a concentration of 0.4 μg/mL, 2 μg/mL, 10 μg/mL, 50 μg/mL, 250 μg/mL or at a concentration ranging between any of the foregoing values (e.g., at a concentration ranging from 2 μg/mL to 10 μg/mL).

In the foregoing assays, the GO2 antibody can be replaced by any antibody or antigen-binding fragment comprising the CDRs or the heavy and light chain variable regions of GO2, such as a humanized or chimeric counterpart of GO2.

In certain aspects, an anti-glyco-MUC1 antibody or antigen-binding fragment of the disclosure comprises heavy and/or light chain variable sequences (or encoded by the nucleotide sequences) set forth in Table 1. In other aspects, an anti-glyco-MUC1 antibody or antigen-binding fragment of the disclosure comprises heavy and/or light chain CDR sequences (or encoded by the nucleotide sequences) set forth in Table 1. The framework sequences for such anti-glyco-MUC1 antibody and antigen-binding fragment can be the native murine framework sequences in Table 1 or can be non-native (e.g., humanized or human) framework sequences.

In yet other aspects, the disclosure provides an anti-MUC1 antibody or antigen binding fragment having heavy and light chain variable regions having at least 95%, 98%, 99%, or 99.5% sequence identity of SEQ ID NOS: 3 and 4, respectively.

In yet other aspects, an anti-glyco-MUC1 antibody or antigen-binding fragment of the disclosure is a single-chain variable fragment (scFv). An exemplary scFv comprises the heavy chain variable fragment N-terminal to the light chain variable fragment. In some embodiments, the scFv heavy chain variable fragment and light chain variable fragment are covalently bound to a linker sequence of 4-15 amino acids. The scFv can be in the form of a bi-specific T-cell engager or within a chimeric antigen receptor (CAR).

6.2 Anti-Glyco-MUC1 and Anti-CD3 Bispecific Antibodies

In some aspects, bispecific antibodies of the disclosure can comprise a first antigen binding domain that specifically binds to CD3 (e.g., which comprises the CDRs or $V_H$ and $V_L$ set forth in Table 4), and a second antigen binding domain that specifically binds to glyco-MUC1. The second antigen binding domain may comprise, singly or in combination, the features described for the glyco-MUC1 antibodies hereinabove (e.g., comprise a combination of CDRs identified in Tables 1-3, for example CDRs comprising the amino acid sequences of any of the CDR combinations set forth in numbered embodiments 3 to 17, infra, or the $V_H$ and $V_L$ sequences identified in Table 1).

TABLE 4

| Description | Sequence | SEQ ID NO: |
|---|---|---|
| CD3 CDR-H1 (Kabat) | TYAMN | 34 |
| CD3 CDR-H2 (Kabat) | RIRSKYNNYATYYADSVKG | 35 |
| CD3 CDR-H3 (Kabat) | HGNFGNSYVSWFAY | 36 |
| CD3 CDR-L1 (Kabat) | GSSTGAVTTSNYAN | 37 |
| CD3 CDR-L2 (Kabat) | GTNKRAP | 38 |
| CD3 CDR-L3 (Kabat) | ALWYSNLWV | 39 |
| CD3 VH | EVQLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVSS | 40 |
| CD3 VL | QAVVTQEPSLTVSPGGTVTLTCGSSTGAVTTSNYANWVQEKP GQAFRGLIGGTNKRAPGTPARFSGSLLGGKAALTLSGAQPED EAEYYCALWYSNLWVFGGGTKLTVL | 41 |
| hIgG1 Fc region | DKTHTCPPCPAPELLGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREP QVYTLPPSRDELTKNQVSLTCLVKGFYPSDIAVEWESNGQPE | 42 |

TABLE 4-continued

| Description | Sequence | SEQ ID NO: |
|---|---|---|
| | NNYKTTPPVLDSDGSFFLYSKLTVDKSRWQQGNVFSCSVMHE ALHNHYTQKSLSLSP | |
| MUC1 VL-CL (RK) | DIVMSQSPSSLGVSVGEKVTMSCKSSQSLLYSTNQKNYQSLL YSTNQKNYLAWYQQKPGQSPKLLIYWVSNRKSGVPDRFTGSG SGTDFTLTISSVKAEDLAVYYCQQYYRYPLTFGAGTKLELKR TVAAPSVFIFPPSDRKLKSGTASVVCLLNNFYPREAKVQWKV DNALQSGNSQESVTEQDSKDSTYSLSSTLTLSKADYEKHKVY ACEVTHQGLSSPVTKSFNRGEC | 43 |
| CD3 VH-CL | EVQLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVSSA SVAAPSVFIFPPSDEQLKSGTASVVCLLNNFYPREAKVQWKV DNALQSGNSQESVTEQDSKDSTYSLSSTLTLSKADYEKHKVY ACEVTHQGLSSPVTKSFNRGEC | 44 |
| MUC1 VH-CH1(EE)-Fc (hole, P329G LALA) | QVQLQQSDAELVKPGASVKISCKASGYTFTDHAIHWVKQRPE QGLEWIGYFSPGNDDIHYNEKFEGKATLTADKSSSTAYMQLN SLTSEDSAVYFCKRSYDKDFDCWGQGTTLTVSSASTKGPSVF PLAPSSKSTSGGTAALGCLVEDYFPEPVTVSWNSGALTSGVH TFPAVLQSSGLYSLSSVVTVPSSSLGTQTYICNVNHKPSNTK VDKEVEPKSCDKTHTCPPCPAPEAAGGPSVFLFPPKPKDTLM ISRTPEVTCVVVDVSHEDPEVKFNWYVDGVEVHNAKTKPREE QYNSTYRVVSVLTVLHQDWLNGKEYKCKVSNKALGAPIEKTI SKAKGQPREPQVCTLPPSRDELTKNQVSLSCAVKGFYPSDIA VEWESNGQPENNYKTTPPVLDSDGSFFLVSKLTVDKSRWQQG NVFSCSVMHEALHNHYTQKSLSLSPGK | 45 |
| MUC1 VH-CH1(EE)-CD3 VL-CH1-Fc (knob, P329G LALA) | QVQLQQSDAELVKPGASVKISCKASGYTFTDHAIHWVKQRPE QGLEWIGYFSPGNDDIHYNEKFEGKATLTADKSSSTAYMQLN SLTSEDSAVYFCKRSYDKDFDCWGQGTTLTVSSASTKGPSVF PLAPSSKSTSGGTAALGCLVEDYFPEPVTVSWNSGALTSGVH TFPAVLQSSGLYSLSSVVTVPSSSLGTQTYICNVNHKPSNTK VDKEVEPKSCDGGGGSGGGGSQAVVTQEPSLTVSPGGTVTLT CGSSTGAVTTSNYANWVQEKPGQAFRGLIGGTNKRAPGTPAR FSGSLLGGKAALTLSGAQPEDEAEYYCALWYSNLWVFGGGTK LTVLSSASTKGPSVFPLAPSSKSTSGGTAALGCLVKDYFPEP VTVSWNSGALTSGVHTFPAVLQSSGLYSLSSVVTVPSSSLGT QTYICNVNHKPSNTKVDKKVEPKSCDKTHTCPPCPAPEAAGG PSVFLFPPKPKDTLMISRTPEVTCVVVDVSHEDPEVKFNWYV DGVEVHNAKTKPREEQYNSTYRVVSVLTVLHQDWLNGKEYKC KVSNKALGAPIEKTISKAKGQPREPQVYTLPPCRDELTKNQV SLWCLVKGFYPSDIAVEWESNGQPENNYKTTPPVLDSDGSFF LYSKLTVDKSRWQQGNVFSCSVMHEALHNHYTQKSLSLSPGK | 46 |

In some embodiments, the first antigen binding domain comprises a heavy chain variable region comprising the heavy chain CDR-H1 of SEQ ID NO:34, the CDR-H2 of SEQ ID NO:35, and the CDR-H3 of SEQ ID NO:36; and a light chain variable region comprising the light chain CDR-L1 of SEQ ID NO:37, the CDR-L2 of SEQ ID NO:38 and the CDR-L3 of SEQ ID NO:39.

In some embodiments, the second antigen binding domain comprises for example CDRs comprising the amino acid sequences of any of the CDR combinations set forth in numbered embodiments 3 to 17, for example (i) a heavy chain variable region comprising the heavy chain CDR-H1 of SEQ ID NO: 5, the CDR-H2 of SEQ ID NO: 6, and the CDR-H3 of SEQ ID NO: 7; and a light chain variable region comprising the light chain CDR (CDR-L) 1 of SEQ ID NO: 8, the CDR-L2 of SEQ ID NO: 9 and the CDR-L3 of SEQ ID NO:10.

In a particular embodiment, the bispecific antibody comprises
(i) a first antigen binding domain that specifically binds to CD3 and comprises a heavy chain variable region comprising a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; and a light chain variable region comprising a CDR-L1 comprising the amino acid sequence of SEQ ID NO:37, a CDR-L2 comprising the amino acid sequence of SEQ ID NO:38, and a CDR-L3 comprising the amino acid sequence of SEQ ID NO:39; and
(ii) a second antigen binding domain that specifically binds to glyco-MUC1 and comprises (i) a heavy chain variable region comprising a CDR-H1 comprising the amino acid sequence of SEQ ID NO:33, more preferably a CDR-H1 comprising the amino acid sequence of SEQ ID NO:5, a CDR-H2 comprising the amino acid sequence of SEQ ID NO:29, more preferably a CDR-H1 comprising the amino acid sequence of SEQ ID NO:6, and a CDR-H3 comprising the amino acid sequence of SEQ ID NO:25, more preferably a CDR-H3 comprising the amino acid sequence of SEQ ID NO:7; and a light chain variable region comprising a CDR-L1 comprising the amino acid sequence of of SEQ ID NO:8, a CDR-L2 comprising the amino acid sequence of SEQ ID NO:9 and a CDR-L3 comprising the amino acid sequence of SEQ ID NO:31, more preferably a CDR-L3 comprising the amino acid sequence of SEQ ID NO:10.

In some embodiments, the first antigen binding domain comprises a heavy chain variable region sequence that is at least about 95%, 96%, 97%, 98%, 99% or 100% identical to the amino acid sequence of SEQ ID NO:40 and a light chain variable region sequence that is at least about 95%, 96%, 97%, 98%, 99% or 100% identical to the amino acid sequence of SEQ ID NO:41.

In some embodiments, the first antigen binding domain comprises the heavy chain variable region sequence of SEQ ID NO:40 and the light chain variable region sequence of SEQ ID NO:41.

In some embodiments, the second antigen binding domain comprises a heavy chain variable region sequence that is at least about 95%, 96%, 97%, 98%, 99% or 100% identical to the amino acid sequence of SEQ ID NO:3 and a light chain variable region sequence that is at least about 95%, 96%, 97%, 98%, 99% or 100% identical to the amino acid sequence of SEQ ID NO:4.

In some embodiments, the second antigen binding domain comprises the heavy chain variable region sequence of SEQ ID NO:3 and the light chain variable region sequence of SEQ ID NO:4.

In some embodiments, the first and/or the second antigen binding domain is a Fab molecule. In some embodiments, the first antigen binding domain is a crossover Fab molecule wherein either the variable or the constant regions of the Fab light chain and the Fab heavy chain are exchanged. In such embodiments, the second antigen binding domain preferably is a conventional Fab molecule.

In some embodiments wherein the first and the second antigen binding domain of the bispecific antibody are both Fab molecules, and in one of the antigen binding domains (particularly the first antigen binding domain) the variable domains VL and VH of the Fab light chain and the Fab heavy chain are replaced by each other,
   i) in the constant domain CL of the first antigen binding domain the amino acid at position 124 is substituted by a positively charged amino acid (numbering according to Kabat), and wherein in the constant domain CH1 of the first antigen binding domain the amino acid at position 147 or the amino acid at position 213 is substituted by a negatively charged amino acid (numbering according to Kabat EU index); or
   ii) in the constant domain CL of the second antigen binding domain the amino acid at position 124 is substituted by a positively charged amino acid (numbering according to Kabat), and wherein in the constant domain CH1 of the second antigen binding domain the amino acid at position 147 or the amino acid at position 213 is substituted by a negatively charged amino acid (numbering according to Kabat EU index).

The bispecific antibody does not comprise both modifications mentioned under i) and ii). The constant domains CL and CH1 of the antigen binding domain having the VH/VL exchange are not replaced by each other (i.e., they remain unexchanged).

In a more specific embodiment,
   i) in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index); or
   ii) in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index).

In one such embodiment, in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index).

In a further embodiment, in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index).

In a particular embodiment, in the constant domain CL of the second antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the second antigen binding domain the amino acid at position 124 is substituted by lysine (K) (numbering according to Kabat) and the amino acid at position 123 is substituted by lysine (K) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the second antigen binding domain the amino acid at position 124 is substituted by lysine (K) (numbering according to Kabat) and the amino acid at position 123 is substituted by arginine (R) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).

In particular embodiments, if amino acid substitutions according to the above embodiments are made in the constant domain CL and the constant domain CH1 of the second antigen binding domain, the constant domain CL of the second antigen binding domain is of kappa isotype.

In some embodiments, the first and the second antigen binding domain are fused to each other, optionally via a peptide linker.

In some embodiments, the first and the second antigen binding domain are each a Fab molecule and either (i) the second antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the Fab heavy chain of the second antigen binding domain.

In some embodiments, the bispecific antibody provides monovalent binding to CD3.

In particular embodiments, the bispecific antibody comprises a single antigen binding domain that specifically binds to CD3, and two antigen binding domains that specifically bind to glyco-MUC1. Thus, in some embodiments, the bispecific antibody comprises a third antigen binding domain that specifically binds to glyco-MUC1. In some embodiments, the third antigen moiety is identical to the first antigen binding domain (e.g. is also a Fab molecule and comprises the same amino acid sequences).

In particular embodiments, the bispecific antibody further comprises an Fc domain composed of a first and a second subunit. In one embodiment, the Fc domain is an IgG Fc domain. In a particular embodiment, the Fc domain is an $IgG_1$ Fc domain. In another embodiment the Fc domain is an IgG4 Fc domain. In a more specific embodiment, the Fc domain is an $IgG_4$ Fc domain comprising an amino acid substitution at position S228 (Kabat EU index numbering), particularly the amino acid substitution S228P. In a further particular embodiment, the Fc domain is a human Fc domain. In an even more particular embodiment, the Fc domain is a human $IgG_1$ Fc domain. An exemplary sequence of a human $IgG_1$ Fc region is given in SEQ ID NO: 42.

In some embodiments wherein the first, the second and, where present, the third antigen binding domain are each a Fab molecule, (a) either (i) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (ii) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and (b) the third antigen binding domain, where present, is fused at the C-terminus of the Fab heavy chain to the N-terminus of the second subunit of the Fc domain.

In particular embodiments, the Fc domain comprises a modification promoting the association of the first and the second subunit of the Fc domain, for example, as described in Section 6.1.

In some embodiments, the Fc domain comprises one or more amino acid substitutions that reduces binding to an Fc receptor and/or effector function, for example as described in Section 6.1.

In a particular embodiment the bispecific antibody comprises
 (i) a first antigen binding domain that specifically binds to CD3, wherein the first antigen binding domain is a crossover Fab molecule wherein either the variable or the constant regions, particularly the variable regions, of the Fab light chain and the Fab heavy chain are exchanged;
 (ii) a second and a third antigen binding domain that specifically bind to glyco-MUC1, comprising a heavy chain variable region comprising the heavy chain CDR-H1 of SEQ ID NO: 5, the CDR-H2 of SEQ ID NO: 6, and the CDR-H3 of SEQ ID NO: 7; and a light chain variable region comprising the light chain CDR-L1 of SEQ ID NO: 8, the CDR-L2 of SEQ ID NO: 9 and the CDR-L3 of SEQ ID NO:10, wherein the second and third antigen binding domain are each a Fab molecule, particularly a conventional Fab molecule;
 (iii) an Fc domain composed of a first and a second subunit capable of stable association,
wherein the second antigen binding domain is fused at the C-terminus of the Fab heavy chain to the N-terminus of the Fab heavy chain of the first antigen binding domain, and the first antigen binding domain is fused at the C-terminus of the Fab heavy chain to the N-terminus of the first subunit of the Fc domain, and wherein the third antigen binding domain is fused at the C-terminus of the Fab heavy chain to the N-terminus of the second subunit of the Fc domain.

In one embodiment the first antigen binding domain comprises a heavy chain variable region comprising the heavy chain CDR-H1 of SEQ ID NO:34, the CDR-H2 of SEQ ID NO:35, and the CDR-H3 of SEQ ID NO:36; and a light chain variable region comprising the light chain CDR-L1 of SEQ ID NO:37, the CDR-L2 of SEQ ID NO:38 and the CDR-L3 of SEQ ID NO:39.

In one embodiment, the first antigen binding domain comprises a heavy chain variable region sequence that is at least about 95%, 96%, 97%, 98%, 99% or 100% identical to the amino acid sequence of SEQ ID NO:40 and a light chain variable region sequence that is at least about 95%, 96%, 97%, 98%, 99% or 100% identical to the amino acid sequence of SEQ ID NO:41.

In one embodiment, the first antigen binding domain comprises the heavy chain variable region sequence of SEQ ID NO:40 and the light chain variable region sequence of SEQ ID NO:41.

In one embodiment, the second and third antigen binding domain comprise a heavy chain variable region sequence that is at least about 95%, 96%, 97%, 98%, 99% or 100% identical to the amino acid sequence of SEQ ID NO:3 and a light chain variable region sequence that is at least about 95%, 96%, 97%, 98%, 99% or 100% identical to the amino acid sequence of SEQ ID NO:4. Preferably, the antigen binding domain comprises CDRs comprising the amino acid sequences of any of the CDR combinations set forth in numbered embodiments 3 to 17. In one embodiment, the second and third antigen binding domains comprise the heavy chain variable region of SEQ ID NO:3 and the light chain variable region of SEQ ID NO:4.

The Fc domain according to the above embodiments may incorporate, singly or in combination, all of the features described hereinabove in relation to Fc domains.

In some embodiments, the antigen binding domains and the Fc region are fused to each other by peptide linkers, for example by peptide linkers as in SEQ ID NO:45 and SEQ ID NO:46.

In one embodiment, in the constant domain CL of the second and the third Fab molecule under (ii) the amino acid at position 124 is substituted by lysine (K) (numbering according to Kabat) and the amino acid at position 123 is substituted by lysine (K) or arginine (R), particularly by arginine (R) (numbering according to Kabat), and in the constant domain CH1 of the second and the third Fab molecule under (ii) the amino acid at position 147 is substituted by glutamic acid (E) (numbering according to Kabat EU index) and the amino acid at position 213 is substituted by glutamic acid (E) (numbering according to Kabat EU index).

In one embodiment, the bispecific antibody comprises a polypeptide comprising a sequence that is at least 80%, 85%, 90%, 95%, 96%, 97%, 98%, or 99% identical to the sequence of SEQ ID NO:43 (and preferably comprises a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31), a polypeptide comprising a sequence that is at least 80%, 85%, 90%, 95%, 96%, 97%, 98%, or 99% identical to the sequence of SEQ ID NO:44 (and preferably comprises the CD3 heavy and light chain CDR sequences set forth in Table 4), a polypeptide comprising a sequence that is at least 80%, 85%, 90%, 95%, 96%, 97%, 98%, or 99% identical to the sequence of SEQ ID NO:45 (and preferably comprises a CDR-H1 comprising the amino acid sequence of SEQ ID NO:33, a CDR-H2 comprising the amino acid sequence of SEQ ID NO:29, a CDR-H3 comprising the amino acid sequence of SEQ ID NO:25), and a polypeptide comprising a sequence that is at least 80%, 85%, 90%, 95%, 96%, 97%, 98%, or 99% identical to the sequence of SEQ ID NO:46 (and preferably comprises a CDR-H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO:37, a CDR-L2 comprising the amino acid sequence of SEQ ID NO:38, and a CDR-L3 comprising the amino acid sequence of SEQ ID NO:39).

In one embodiment, the bispecific antibody comprises a polypeptide (particularly two polypeptides) comprising the sequence of SEQ ID NO:43, a polypeptide comprising the sequence of SEQ ID NO:44, a polypeptide comprising the sequence of SEQ ID NO:45, and a polypeptide comprising the sequence of SEQ ID NO:46.

6.3 Antibody-Drug Conjugates

Another aspect of the disclosure concerns antibody drug conjugates (ADCs) including the anti-glyco-MUC1 antibodies and antigen-binding fragments of the disclosure. The ADCs generally comprise an anti-glyco-MUC1 antibody and/or binding fragment as described herein having one or more cytotoxic and/or cytostatic agents linked thereto by way of one or more linkers. In specific embodiments, the ADCs are compounds according to structural formula (I):

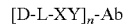

or salts thereof, where each "D" represents, independently of the others, a cytotoxic and/or cytostatic agent ("drug"); each "L" represents, independently of the others, a linker; "Ab" represents an anti-glyco-MUC1 antigen binding domain, such as an anti-glyco-MUC1 antibody or binding fragment described herein; each "XY" represents a linkage formed between a functional group $R^x$ on the linker and a "complementary" functional group $R^y$ on the antibody, and n represents the number of drugs linked to, or drug-to-antibody ratio (DAR), of the ADC.

Specific embodiments of the various antibodies (Ab) that can comprise the ADCs include the various embodiments of anti-glyco-MUC1 antibodies and/or binding fragments described above.

In some specific embodiments of the ADCs and/or salts of structural formula (I), each D is the same and/or each L is the same.

Specific embodiments of cytotoxic and/or cytostatic agents (D) and linkers (L) that can comprise the anti-glyco-MUC1 ADCs of the disclosure, as well as the number of cytotoxic and/or cytostatic agents linked to the ADCs, are described in more detail below.

6.3.1. Cytotoxic and/or Cytostatic Agents

The cytotoxic and/or cytostatic agents may be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, radionuclides, alkylating agents, topoisomerase I inhibitors, topoisomerase II inhibitors, DNA intercalating agents (e.g., groove binding agents such as minor groove binders), RNA/DNA antimetabolites, cell cycle modulators, kinase inhibitors, protein synthesis inhibitors, histone deacetylase inhibitors, mitochondria inhibitors, and antimitotic agents.

Specific non-limiting examples of agents within certain of these various classes are provided below.

Alkylatinq Agents: asaley ((L-Leucine, N—[N-acetyl-4-[bis-(2-chloroethyl)amino]-DL-phenylalanyl]-, ethylester; NSC 167780; CAS Registry No. 3577897)); AZQ ((1,4-cyclohexadiene-1,4-dicarbamic acid, 2,5-bis(1-aziridinyl)-3,6-dioxo-, diethyl ester; NSC 182986; CAS Registry No. 57998682)); BCNU ((N,N'-Bis(2-chloroethyl)-N-nitrosourea; NSC 409962; CAS Registry No. 154938)); busulfan (1,4-butanediol dimethanesulfonate; NSC 750; CAS Registry No. 55981); (carboxyphthalato)platinum (NSC 27164; CAS Registry No. 65296813); CBDCA ((cis-(1,1-cyclobutanedicarboxylato)diammineplatinum(II)); NSC 241240; CAS Registry No. 41575944)); CCNU ((N-(2-chloroethyl)-N'-cyclohexyl-N-nitrosourea; NSC 79037; CAS Registry No. 13010474)); CHIP (iproplatin; NSC 256927); chlorambucil (NSC 3088; CAS Registry No. 305033); chlorozotocin ((2-[[[(2-chloroethyl) nitrosoamino] carbonyl]amino]-2-deoxy-D-glucopyranose; NSC 178248; CAS Registry No. 54749905)); cis-platinum (cisplatin; NSC 119875; CAS Registry No. 15663271); clomesone (NSC 338947; CAS Registry No. 88343720); cyanomorpholinodoxorubicin (NCS 357704; CAS Registry No. 88254073); cyclodisone (NSC 348948; CAS Registry No. 99591738); dianhydrogalactitol (5,6-diepoxydulcitol; NSC 132313; CAS Registry No. 23261203); fluorodopan ((5-[(2-chloroethyl)-(2-fluoroethyl)amino]-6-methyl-uracil; NSC 73754; CAS Registry No. 834913); hepsulfam (NSC 329680; CAS Registry No. 96892578); hycanthone (NSC 142982; CAS Registry No. 23255938); melphalan (NSC 8806; CAS Registry No. 3223072); methyl CCNU ((1-(2-chloroethyl)-3-(trans-4-methylcyclohexane)-1-nitrosourea; NSC 95441; 13909096); mitomycin C (NSC 26980; CAS Registry No. 50077); mitozolamide (NSC 353451; CAS Registry No. 85622953); nitrogen mustard ((bis(2-chloroethyl)methylamine hydrochloride; NSC 762; CAS Registry No. 55867); PCNU ((1-(2-chloroethyl)-3-(2,6-dioxo-3-piperidyl)-1-nitrosourea; NSC 95466; CAS Registry No. 13909029)); piperazine alkylator ((1-(2-chloroethyl)-4-(3-chloropropyl)-piperazine dihydrochloride; NSC 344007)); piperazinedione (NSC 135758; CAS Registry No. 41109802); pipobroman ((N,N-bis(3-bromopropionyl) piperazine; NSC 25154; CAS Registry No. 54911)); porfiromycin (N-methylmitomycin C; NSC 56410; CAS Registry No. 801525); spirohydantoin mustard (NSC 172112; CAS Registry No. 56605164); teroxirone (triglycidylisocyanurate; NSC 296934; CAS Registry No. 2451629); tetraplatin (NSC 363812; CAS Registry No. 62816982); thio-tepa (N,N',N"-tri-1,2-ethanediylthio phosphoramide; NSC 6396; CAS Registry No. 52244); triethylenemelamine (NSC 9706; CAS Registry No. 51183); uracil nitrogen mustard (desmethyldopan; NSC 34462; CAS Registry No. 66751); Yoshi-864 ((bis(3-mesyloxy propyl)amine hydrochloride; NSC 102627; CAS Registry No. 3458228).

Topoisomerase I Inhibitors: camptothecin (NSC 94600; CAS Registry No. 7689-03-4); various camptothecin derivatives and analogs (for example, NSC 100880, NSC 603071, NSC 107124, NSC 643833, NSC 629971, NSC 295500, NSC 249910, NSC 606985, NSC 74028, NSC 176323, NSC 295501, NSC 606172, NSC 606173, NSC 610458, NSC 618939, NSC 610457, NSC 610459, NSC 606499, NSC 610456, NSC 364830, and NSC 606497); morpholinisoxorubicin (NSC 354646; CAS Registry No. 89196043); SN-38 (NSC 673596; CAS Registry No. 86639-52-3).

Topoisomerase II Inhibitors: doxorubicin (NSC 123127; CAS Registry No. 25316409); amonafide (benzisoquinolinedione; NSC 308847; CAS Registry No. 69408817); m-AMSA ((4'-(9-acridinylamino)-3'-methoxymethanesulfonanilide; NSC 249992; CAS Registry No. 51264143)); anthrapyrazole derivative ((NSC 355644); etoposide (VP-16; NSC 141540; CAS Registry No. 33419420); pyrazoloacridine ((pyrazolo[3,4,5-kl]acridine-2(6H)-propanamine, 9-methoxy-N,N-dimethyl-5-nitro-, monomethanesulfonate; NSC 366140; CAS Registry No. 99009219); bisantrene hydrochloride (NSC 337766; CAS Registry No. 71439684); daunorubicin (NSC 821151; CAS Registry No. 23541506); deoxydoxorubicin (NSC 267469; CAS Registry No. 63950061); mitoxantrone (NSC 301739; CAS Registry No. 70476823); menogaril (NSC 269148; CAS Registry No. 71628961); N,N-dibenzyl daunomycin (NSC 268242; CAS Registry No. 70878512); oxanthrazole (NSC 349174; CAS Registry No. 105118125); rubidazone (NSC 164011; CAS Registry No. 36508711); teniposide (VM-26; NSC 122819; CAS Registry No. 29767202).

DNA Intercalating Agents: anthramycin (CAS Registry No. 4803274); chicamycin A (CAS Registry No. 89675376); tomaymycin (CAS Registry No. 35050556); DC-81 (CAS Registry No. 81307246); sibiromycin (CAS Registry No. 12684332); pyrrolobenzodiazepine derivative (CAS Registry No. 945490095); SGD-1882 ((S)-2-(4-aminophenyl)-7-methoxy-8-(3-4(S)-7-methoxy-2-(4-methoxyphenyl)-5-oxo-5,11a-dihydro-1H-benzo[e]pyrrolo[1,2-a][1,4]diazepin-8-yl)oxy)propox-y)-1H-benzo[e]pyrrolo[1,2-a][1,4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5 (11aH)-one); NSC 694501; CAS Registry No. 232931576).

RNA/DNA Antimetabolites: L-alanosine (NSC 153353; CAS Registry No. 59163416); 5-azacytidine (NSC 102816; CAS Registry No. 320672); 5-fluorouracil (NSC 19893; CAS Registry No. 51218); acivicin (NSC 163501; CAS Registry No. 42228922); aminopterin derivative N-[2-chloro-5-[[(2,4-diamino-5-methyl-6-quinazolinyl)methyl] amino]benzoyl-]L-aspartic acid (NSC 132483); aminopterin derivative N-4-[[(2,4-diamino-5-ethyl-6-quinazolinyhmethyl]amino]benzoyl]L-asparti-c acid (NSC 184692); aminopterin derivative N-[2-chloro-4-[[(2,4-diamino-6-pteridinyl)methyl]amino]benzoyl]L-aspartic acid monohydrate (NSC 134033); an antifo ((N$^\alpha$-(4-amino-4-deoxypteroyl)-N$^7$-hemiphthaloyl-L-ornithin-e; NSC 623017)); Bakers soluble antifol (NSC 139105; CAS Registry No. 41191042); dichlorallyl lawsone ((2-(3,3-dichloroallyl)-3-hydroxy-1,4-naphthoquinone; NSC 126771; CAS Registry No. 36417160); brequinar (NSC 368390; CAS Registry No. 96201886); ftorafur ((pro-drug; 5-fluoro-1-(tetrahydro-2-furyl)-uracil; NSC 148958; CAS Registry No. 37076689); 5,6-dihydro-5-azacytidine (NSC 264880; CAS Registry No. 62402317); methotrexate (NSC 740; CAS Registry No. 59052); methotrexate derivative (N-[[4-[[(2,4-diamino-6-pteridinyl)methyl]methylamino]-1-naphthalenyl]car-bonyl] L-glutamic acid; NSC 174121); PALA ((N-(phosphonoacetyl)-L-aspartate; NSC 224131; CAS Registry No. 603425565); pyrazofurin (NSC 143095; CAS Registry No. 30868305); trimetrexate (NSC 352122; CAS Registry No. 82952645).

DNA Antimetabolites: 3-HP (NSC 95678; CAS Registry No. 3814797); 2'-deoxy-5-fluorouridine (NSC 27640; CAS Registry No. 50919); 5-HP (NSC 107392; CAS Registry No. 19494894); α-TGDR (α-2'-deoxy-6-thioguanosine; NSC 71851 CAS Registry No. 2133815); aphidicolin glycinate (NSC 303812; CAS Registry No. 92802822); ara C (cytosine arabinoside; NSC 63878; CAS Registry No. 69749); 5-aza-2'-deoxycytidine (NSC 127716; CAS Registry No. 2353335); β-TGDR (β-2'-deoxy-6-thioguanosine; NSC 71261; CAS Registry No. 789617); cyclocytidine (NSC 145668; CAS Registry No. 10212256); guanazole (NSC 1895; CAS Registry No. 1455772); hydroxyurea (NSC 32065; CAS Registry No. 127071); inosine glycodialdehyde (NSC 118994; CAS Registry No. 23590990); macbecin II (NSC 330500; CAS Registry No. 73341738); pyrazoloimidazole (NSC 51143; CAS Registry No. 6714290); thioguanine (NSC 752; CAS Registry No. 154427); thiopurine (NSC 755; CAS Registry No. 50442).

Cell Cycle Modulators: silibinin (CAS Registry No. 22888-70-6); epigallocatechin gallate (EGCG; CAS Registry No. 989515); procyanidin derivatives (e.g., procyanidin A2 [CAS Registry No. 103883030], procyanidin B1 [CAS Registry No. 20315257], procyanidin B4 [CAS Registry No. 29106512], are catannin B1 [CAS Registry No. 79763283]); isoflavones (e.g., genistein [4%5,7-trihydroxyisoflavone; CAS Registry No. 446720], daidzein [4',7-dihydroxyisoflavone, CAS Registry No. 486668]; indole-3-carbinol (CAS Registry No. 700061); quercetin (NSC 9219; CAS Registry No. 117395); estramustine (NSC 89201; CAS Registry No. 2998574); nocodazole (CAS Registry No. 31430189); podophyllotoxin (CAS Registry No. 518285); vinorelbine tartrate (NSC 608210; CAS Registry No. 125317397); cryptophycin (NSC 667642; CAS Registry No. 124689652).

Kinase Inhibitors: afatinib (CAS Registry No. 850140726); axitinib (CAS Registry No. 319460850); ARRY-438162 (binimetinib) (CAS Registry No. 606143899); bosutinib (CAS Registry No. 380843754); cabozantinib (CAS Registry No. 1140909483); ceritinib (CAS Registry No. 1032900256); crizotinib (CAS Registry No. 877399525); dabrafenib (CAS Registry No. 1195765457); dasatinib (NSC 732517; CAS Registry No. 302962498); erlotinib (NSC 718781; CAS Registry No. 183319699); everolimus (NSC 733504; CAS Registry No. 159351696); fostamatinib (NSC 745942; CAS Registry No. 901119355); gefitinib (NSC 715055; CAS Registry No. 184475352); ibrutinib (CAS Registry No. 936563961); imatinib (NSC 716051; CAS Registry No. 220127571); lapatinib (CAS Registry No. 388082788); lenvatinib (CAS Registry No. 857890392); mubritinib (CAS 366017096); nilotinib (CAS Registry No. 923288953); nintedanib (CAS Registry No. 656247175); palbociclib (CAS Registry No. 571190302); pazopanib (NSC 737754; CAS Registry No. 635702646); pegaptanib (CAS Registry No. 222716861); ponatinib (CAS Registry No. 1114544318); rapamycin (NSC 226080; CAS Registry No. 53123889); regorafenib (CAS Registry No. 755037037); AP 23573 (ridaforolimus) (CAS Registry No. 572924540); INCB018424 (ruxolitinib) (CAS Registry No. 1092939177); ARRY-142886 (selumetinib) (NSC 741078; CAS Registry No. 606143-52-6); sirolimus (NSC 226080; CAS Registry No. 53123889);

sorafenib (NSC 724772; CAS Registry No. 475207591); sunitinib (NSC 736511; CAS Registry No. 341031547); tofacitinib (CAS Registry No. 477600752); temsirolimus (NSC 683864; CAS Registry No. 163635043); trametinib (CAS Registry No. 871700173); vandetanib (CAS Registry No. 443913733); vemurafenib (CAS Registry No. 918504651); SU6656 (CAS Registry No. 330161870); CEP-701 (lesaurtinib) (CAS Registry No. 111358884); XL019 (CAS Registry No. 945755566); PD-325901 (CAS Registry No. 391210109); PD-98059 (CAS Registry No. 167869218); ATP-competitive TORC1/TORC2 inhibitors including PI-103 (CAS Registry No. 371935749), PP242 (CAS Registry No. 1092351671), PP30 (CAS Registry No. 1092788094), Torin 1 (CAS Registry No. 1222998368), LY294002 (CAS Registry No. 154447366), XL-147 (CAS Registry No. 934526893), CAL-120 (CAS Registry No. 870281348), ETP-45658 (CAS Registry No. 1198357797), PX 866 (CAS Registry No. 502632668), GDC-0941 (CAS Registry No. 957054307), BGT226 (CAS Registry No. 1245537681), BEZ235 (CAS Registry No. 915019657), XL-765 (CAS Registry No. 934493762).

Protein Synthesis Inhibitors: acriflavine (CAS Registry No. 65589700); amikacin (NSC 177001; CAS Registry No. 39831555); arbekacin (CAS Registry No. 51025855); astromicin (CAS Registry No. 55779061); azithromycin (NSC 643732; CAS Registry No. 83905015); bekanamycin (CAS Registry No. 4696768); chlortetracycline (NSC 13252; CAS Registry No. 64722); clarithromycin (NSC 643733; CAS Registry No. 81103119); clindamycin (CAS Registry No. 18323449); clomocycline (CAS Registry No. 1181540); cycloheximide (CAS Registry No. 66819); dactinomycin (NSC 3053; CAS Registry No. 50760); dalfopristin (CAS Registry No. 112362502); demeclocycline (CAS Registry No. 127333); dibekacin (CAS Registry No. 34493986); dihydrostreptomycin (CAS Registry No. 128461); dirithromycin (CAS Registry No. 62013041); doxycycline (CAS Registry No. 17086281); emetine (NSC 33669; CAS Registry No. 483181); erythromycin (NSC 55929; CAS Registry No. 114078); flurithromycin (CAS Registry No. 83664208); framycetin (neomycin B; CAS Registry No. 119040); gentamycin (NSC 82261; CAS Registry No. 1403663); glycylcyclines, such as tigecycline (CAS Registry No. 220620097); hygromycin B (CAS Registry No. 31282049); isepamicin (CAS Registry No. 67814760); josamycin (NSC 122223; CAS Registry No. 16846245); kanamycin (CAS Registry No. 8063078); ketolides such as telithromycin (CAS Registry No. 191114484), cethromycin (CAS Registry No. 205110481), and solithromycin (CAS Registry No. 760981837); lincomycin (CAS Registry No. 154212); lymecycline (CAS Registry No. 992212); meclocycline (NSC 78502; CAS Registry No. 2013583); metacycline (rondomycin; NSC 356463; CAS Registry No. 914001); midecamycin (CAS Registry No. 35457808); minocycline (NSC 141993; CAS Registry No. 10118908); miocamycin (CAS Registry No. 55881077); neomycin (CAS Registry No. 119040); netilmicin (CAS Registry No. 56391561); oleandomycin (CAS Registry No. 3922905); oxazolidinones, such as eperezolid (CAS Registry No. 165800044), linezolid (CAS Registry No. 165800033), posizolid (CAS Registry No. 252260029), radezolid (CAS Registry No. 869884786), ranbezolid (CAS Registry No. 392659380), sutezolid (CAS Registry No. 168828588), tedizolid (CAS Registry No. 856867555); oxytetracycline (NSC 9169; CAS Registry No. 2058460); paromomycin (CAS Registry No. 7542372); penimepicycline (CAS Registry No. 4599604); peptidyl transferase inhibitors, e.g., chloramphenicol (NSC 3069; CAS Registry No. 56757) and derivatives such as azidamfenicol (CAS Registry No. 13838089), florfenicol (CAS Registry No. 73231342), and thiamphenicol (CAS Registry No. 15318453), and pleuromutilins such as retapamulin (CAS Registry No. 224452668), tiamulin (CAS Registry No. 55297955), valnemulin (CAS Registry No. 101312929); pirlimycin (CAS Registry No. 79548735); puromycin (NSC 3055; CAS Registry No. 53792); quinupristin (CAS Registry No. 120138503); ribostamycin (CAS Registry No. 53797356); rokitamycin (CAS Registry No. 74014510); rolitetracycline (CAS Registry No. 751973); roxithromycin (CAS Registry No. 80214831); sisomicin (CAS Registry No. 32385118); spectinomycin (CAS Registry No. 1695778); spiramycin (CAS Registry No. 8025818); streptogramins such as pristinamycin (CAS Registry No. 270076603), quinupristin/dalfopristin (CAS Registry No. 126602899), and virginiamycin (CAS Registry No. 11006761); streptomycin (CAS Registry No. 57921); tetracycline (NSC 108579; CAS Registry No. 60548); tobramycin (CAS Registry No. 32986564); troleandomycin (CAS Registry No. 2751099); tylosin (CAS Registry No. 1401690); verdamicin (CAS Registry No. 49863481).

Histone Deacetylase Inhibitors: abexinostat (CAS Registry No. 783355602); belinostat (NSC 726630; CAS Registry No. 414864009); chidamide (CAS Registry No. 743420022); entinostat (CAS Registry No. 209783802); givinostat (CAS Registry No. 732302997); mocetinostat (CAS Registry No. 726169739); panobinostat (CAS Registry No. 404950807); quisinostat (CAS Registry No. 875320299); resminostat (CAS Registry No. 864814880); romidepsin (CAS Registry No. 128517077); sulforaphane (CAS Registry No. 4478937); thioureidobutyronitrile (Kevetrin™; CAS Registry No. 6659890); valproic acid (NSC 93819; CAS Registry No. 99661); vorinostat (NSC 701852; CAS Registry No. 149647789); ACY-1215 (rocilinostat; CAS Registry No. 1316214524); CUDC-101 (CAS Registry No. 1012054599); CHR-2845 (tefinostat; CAS Registry No. 914382608); CHR-3996 (CAS Registry No. 1235859138); 4SC-202 (CAS Registry No. 910462430); CG200745 (CAS Registry No. 936221339); SB939 (pracinostat; CAS Registry No. 929016966).

Mitochondria Inhibitors: pancratistatin (NSC 349156; CAS Registry No. 96281311); rhodamine-123 (CAS Registry No. 63669709); edelfosine (NSC 324368; CAS Registry No. 70641519); d-alpha-tocopherol succinate (NSC 173849; CAS Registry No. 4345033); compound 11β (CAS Registry No. 865070377); aspirin (NSC 406186; CAS Registry No. 50782); ellipticine (CAS Registry No. 519233); berberine (CAS Registry No. 633658); cerulenin (CAS Registry No. 17397896); GX015-070 (Obatoclax®; 1H-Indole, 2-(2-((3,5-dimethyl-1H-pyrrol-2-yl)methylene)-3-methoxy-2H-pyrrol-5-yl)-; NSC 729280; CAS Registry No. 803712676); celastrol (tripterine; CAS Registry No. 34157830); metformin (NSC 91485; CAS Registry No. 1115704); Brilliant green (NSC 5011; CAS Registry No. 633034); ME-344 (CAS Registry No. 1374524556).

Antimitotic Agents: allocolchicine (NSC 406042); auristatins, such as MMAE (monomethyl auristatin E; CAS Registry No. 474645-27-7) and MMAF (monomethyl auristatin F; CAS Registry No. 745017-94-1; halichondrin B (NSC 609395); colchicine (NSC 757; CAS Registry No. 64868); cholchicine derivative (N-benzoyl-deacetyl benzamide; NSC 33410; CAS Registry No. 63989753); dolastatin 10 (NSC 376128; CAS Registry No 110417-88-4); maytansine (NSC 153858; CAS Registry No. 35846-53-8); rhozoxin (NSC 332598; CAS Registry No. 90996546); taxol (NSC 125973; CAS Registry No. 33069624); taxol derivative ((2'-N-[3-(dimethylamino)propyl]glutaramate taxol; NSC 608832); thiocolchicine (3-demethylthiocolchicine; NSC 361792); trityl cysteine (NSC 49842; CAS Registry No. 2799077); vinblastine sulfate (NSC 49842; CAS Registry No. 143679); vincristine sulfate (NSC 67574; CAS Registry No. 2068782).

Any of these agents that include or that may be modified to include a site of attachment to an antibody may be included in the ADCs disclosed herein.

In a specific embodiment, the cytotoxic and/or cytostatic agent is an antimitotic agent.

In another specific embodiment, the cytotoxic and/or cytostatic agent is an auristatin, for example, monomethyl auristatin E ("MMAE") or monomethyl auristatin F ("MMAF").

6.3.2. Linkers

In the anti-glyco-MUC1 ADCs of the disclosure, the cytotoxic and/or cytostatic agents are linked to the antibody by way of linkers. The linker linking a cytotoxic and/or cytostatic agent to the antibody of an ADC may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the antibody, or monovalent such that covalently they link a single agent to a single site on the antibody.

As will be appreciated by skilled artisans, the linkers link cytotoxic and/or cytostatic agents to the antibody by forming a covalent linkage to the cytotoxic and/or cytostatic agent at one location and a covalent linkage to antibody at another. The covalent linkages are formed by reaction between functional groups on the linker and functional groups on the agents and antibody. As used herein, the expression "linker" is intended to include (i) unconjugated forms of the linker that include a functional group capable of covalently linking the linker to a cytotoxic and/or cytostatic agent and a functional group capable of covalently linking the linker to an antibody; (ii) partially conjugated forms of the linker that includes a functional group capable of covalently linking the linker to an antibody and that is covalently linked to a cytotoxic and/or cytostatic agent, or vice versa; and (iii) fully conjugated forms of the linker that is covalently linked to both a cytotoxic and/or cytostatic agent and an antibody. In some specific embodiments of linkers and anti-glyco-MUC1 ADCs of the disclosure, as well as synthons used to conjugate linker-agents to antibodies, moieties comprising the functional groups on the linker and covalent linkages formed between the linker and antibody are specifically illustrated as $R_x$ and XY, respectively.

The linkers are preferably, but need not be, chemically stable to conditions outside the cell, and may be designed to cleave, immolate and/or otherwise specifically degrade inside the cell. Alternatively, linkers that are not designed to specifically cleave or degrade inside the cell may be used. Choice of stable versus unstable linker may depend upon the toxicity of the cytotoxic and/or cytostatic agent. For agents that are toxic to normal cells, stable linkers are preferred. Agents that are selective or targeted and have lower toxicity to normal cells may utilize, chemical stability of the linker to the extracellular milieu is less important. A wide variety of linkers useful for linking drugs to antibodies in the context of ADCs are known in the art. Any of these linkers, as well as other linkers, may be used to link the cytotoxic and/or cytostatic agents to the antibody of the anti-glyco-MUC1 ADCs of the disclosure.

Exemplary polyvalent linkers that may be used to link many cytotoxic and/or cytostatic agents to a single antibody molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the content of which are incorporated herein by reference in their entireties. For example, the Fleximer linker technology developed by Mersana et al. has the potential to enable high-DAR ADCs with good physicochemical properties. As shown below, the Mersana technology is based on incorporating drug molecules into a solubilizing poly-acetal backbone via a sequence of ester bonds. The methodology renders highly-loaded ADCs (DAR up to 20) while maintaining good physicochemical properties.

Additional examples of dendritic type linkers can be found in US 2006/116422; US 2005/271615; de Groot et al. (2003) Angew. Chem. Int. Ed. 42:4490-4494; Amir et al. (2003) Angew. Chem. Int. Ed. 42:4494-4499; Shamis et al. (2004) J. Am. Chem. Soc. 126:1726-1731; Sun et al. (2002) Bioorganic & Medicinal Chemistry Letters 12:2213-2215; Sun et al. (2003) Bioorganic & Medicinal Chemistry 11:1761-1768; King et al. (2002) Tetrahedron Letters 43:1987-1990, each of which is incorporated herein by reference.

Exemplary monovalent linkers that may be used are described, for example, in Nolting, 2013, Antibody-Drug Conjugates, Methods in Molecular Biology 1045:71-100; Kitson et al., 2013, CROs/CMOs—Chemica Oggi—Chemistry Today 31(4):30-38; Ducry et al., 2010, Bioconjugate Chem. 21:5-13; Zhao et al., 2011, J. Med. Chem. 54:3606-3623; U.S. Pat. Nos. 7,223,837; 8,568,728; 8,535,678; and WO2004010957, each of which is incorporated herein by reference.

By way of example and not limitation, some cleavable and noncleavable linkers that may be included in the anti-glyco-MUC1 ADCs of the disclosure are described below.

6.3.3. Cleavable Linkers

In certain embodiments, the linker selected is cleavable in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable. In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures:

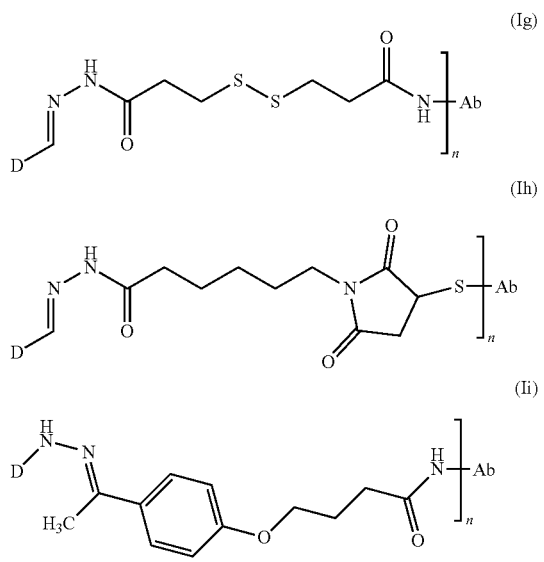

wherein D and Ab represent the cytotoxic and/or cytostatic agent (drug) and Ab, respectively, and n represents the number of drug-linkers linked to the antibody. In certain linkers such as linker (Ig), the linker comprises two cleavable groups—a disulfide and a hydrazone moiety. For such linkers, effective release of the unmodified free drug requires acidic pH or disulfide reduction and acidic pH. Linkers such as (Ih) and (Ii) have been shown to be effective with a single hydrazone cleavage site.

Additional linkers which remain intact during systemic circulation and undergo hydrolysis and release the drug when the ADC is internalized into acidic cellular compartments include carbonates. Such linkers can be useful in cases where the cytotoxic and/or cytostatic agent can be covalently attached through an oxygen.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonably stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hindrance adjacent to the disulfide bond.

ADCs including exemplary disulfide-containing linkers include the following structures:

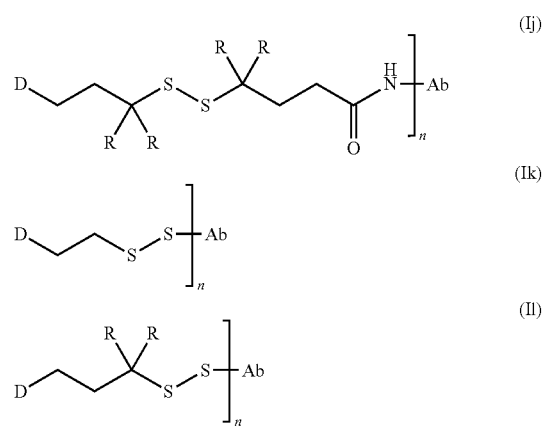

wherein D and Ab represent the drug and antibody, respectively, n represents the number of drug-linkers linked to the antibody and R is independently selected at each occurrence from hydrogen or alkyl, for example. In certain embodiments, increasing steric hindrance adjacent to the disulfide bond increases the stability of the linker. Structures such as (IcD and (II) show increased in vivo stability when one or more R groups is selected from a lower alkyl such as methyl.

Another type of cleavable linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor cells.

In exemplary embodiments, the cleavable peptide is selected from tetrapeptides such as Gly-Phe-Leu-Gly (SEQ ID NO: 56), Ala-Leu-Ala-Leu (SEQ ID NO:57) or dipeptides such as Val-Cit, Val-Ala, Met-(D)Lys, Asn-(D)Lys, Val-(D)Asp, Phe-Lys, Ile-Val, Asp-Val, His-Val, NorVal-(D) Asp, Ala-(D)Asp 5, Met-Lys, Asn-Lys, Ile-Pro, Me3Lys-Pro, PhenylGly-(D)Lys, Met-(D)Lys, Asn-(D)Lys, Pro-(D) Lys, Met-(D)Lys, Asn-(D)Lys, AM Met-(D)Lys, Asn-(D) Lys, AW Met-(D)Lys, and Asn-(D)Lys. In certain embodiments, dipeptides are preferred over longer polypeptides due to hydrophobicity of the longer peptides.

A variety of dipeptide-based cleavable linkers useful for linking drugs such as doxorubicin, mitomycin, camptothecin, pyrrolobenzodiazepine, tallysomycin and auristatin/auristatin family members to antibodies have been described (see, Dubowchik et al., 1998, J. Org. Chem. 67:1866-1872; Dubowchik et al., 1998, Bioorg. Med. Chem. Lett. 8(21): 3341-3346; Walker et al., 2002, Bioorg. Med. Chem. Lett. 12:217-219; Walker et al., 2004, Bioorg. Med. Chem. Lett. 14:4323-4327; Sutherland et al., 2013, Blood 122: 1455-1463; and Francisco et al., 2003, Blood 102:1458-1465, of each of which is incorporated herein by reference). All of these dipeptide linkers, or modified versions of these dipeptide linkers, may be used in the anti-glyco-MUC1 ADCs of the disclosure. Other dipeptide linkers that may be used include those found in ADCs such as Seattle Genetics' Brentuximab Vendotin SGN-35 (Adcetris™), Seattle Genetics SGN-75 (anti-CD-70, Val-Cit-monomethyl auristatin F(MMAF), Seattle Genetics SGN-CD33A (anti-CD-33, Val-Ala-(SGD-1882)), Celldex Therapeutics glembatumumab (CDX-011) (anti-NMB, Val-Cit-monomethyl auristatin E (MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-amidobenzyl ether and release of the drug:

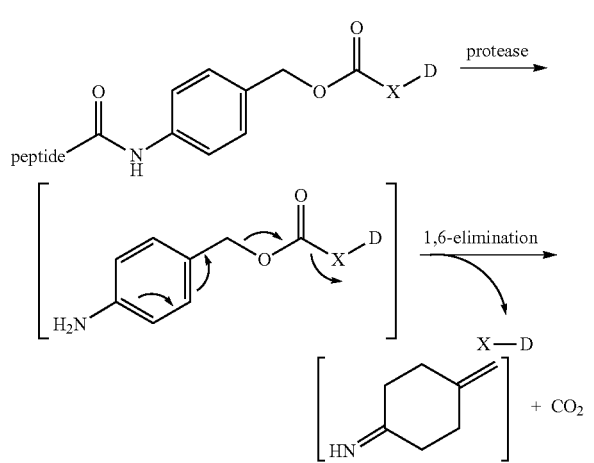

wherein X-D represents the unmodified drug.

Heterocyclic variants of this self-immolative group have also been described. See for example, U.S. Pat. No. 7,989,434, incorporated herein by reference.

In some embodiments, the enzymatically cleavable linker is a β-glucuronic acid-based linker. Facile release of the drug may be realized through cleavage of the β-glucuronide glycosidic bond by the lysosomal enzyme β-glucuronidase. This enzyme is present abundantly within lysosomes and is overexpressed in some tumor types, while the enzyme activity outside cells is low. β-Glucuronic acid-based linkers may be used to circumvent the tendency of an ADC to undergo aggregation due to the hydrophilic nature of β-glucuronides. In some embodiments, β-glucuronic acid-based linkers are preferred as linkers for ADCs linked to hydrophobic drugs. The following scheme depicts the release of the drug from and ADC containing a β-glucuronic acid-based linker:

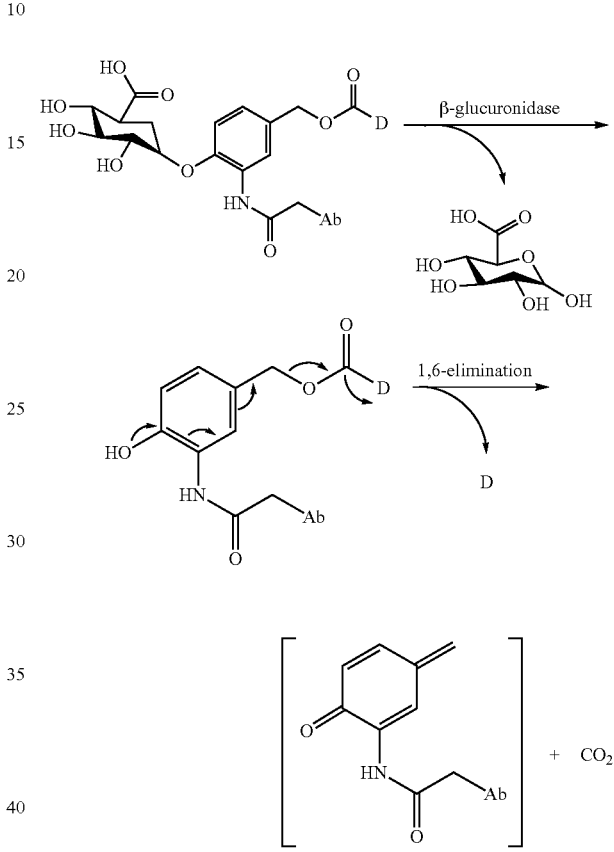

A variety of cleavable β-glucuronic acid-based linkers useful for linking drugs such as auristatins, camptothecin and doxorubicin analogues, CBI minor-groove binders, and psymberin to antibodies have been described (see, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013; Jeffrey et al., 2006, Bioconjug. Chem. 17:831-840; Jeffrey et al., 2007, Bioorg. Med. Chem. Lett. 17:2278-2280; and Jiang et al., 2005, J. Am. Chem. Soc. 127:11254-11255, each of which is incorporated herein by reference). All of these β-glucuronic acid-based linkers may be used in the anti-glyco-MUC1 ADCs of the disclosure.

Additionally, cytotoxic and/or cytostatic agents containing a phenol group can be covalently bonded to a linker through the phenolic oxygen. One such linker, described in WO 2007/089149, relies on a methodology in which a diamino-ethane "SpaceLink" is used in conjunction with traditional "PABO"-based self-immolative groups to deliver phenols. The cleavage of the linker is depicted schematically below, where D represents a cytotoxic and/or cytostatic agent having a phenolic hydroxyl group.

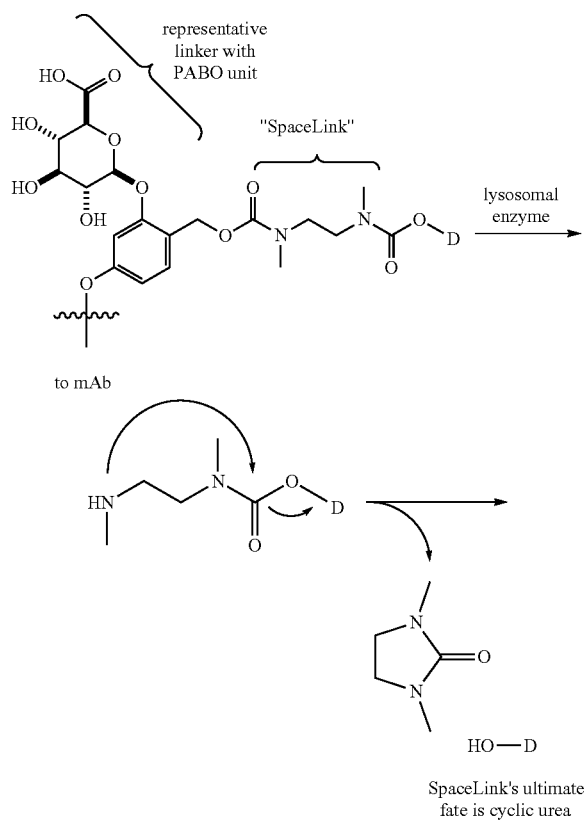

Cleavable linkers may include noncleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazone or a dipeptide.

Other degradable linkages that may be included in linkers include ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the linker comprises an enzymatically cleavable peptide moiety, for example, a linker comprising structural formula (IVa) or (IVb):

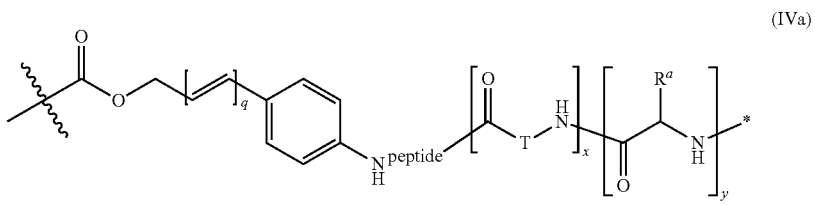

(IVa)

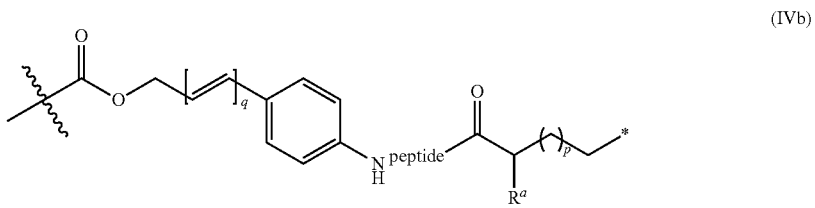

(IVb)

or a salt thereof, wherein: peptide represents a peptide (illustrated C→N and not showing the carboxy and amino "termini") cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; p is an integer ranging from 0 to 5; q is 0 or 1; x is 0 or 1; y is 0 or 1; ∫ represents the point of attachment of the linker to a cytotoxic and/or cytostatic agent; and * represents the point of attachment to the remainder of the linker.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the dipeptide is selected from: Cit-Val; and Ala-Val.

Specific exemplary embodiments of linkers according to structural formula (IVa) that may be included in the anti-glyco-MUC1 ADCs of the disclosure include the linkers illustrated below (as illustrated, the linkers include a group suitable for covalently linking the linker to an antibody):

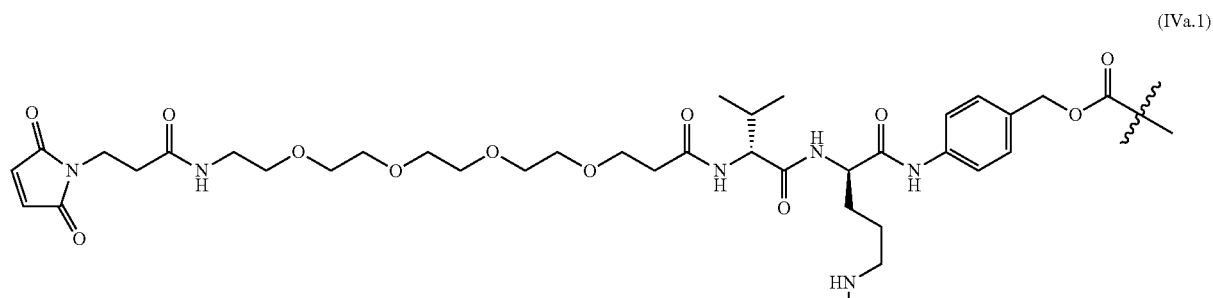

(IVa.1)

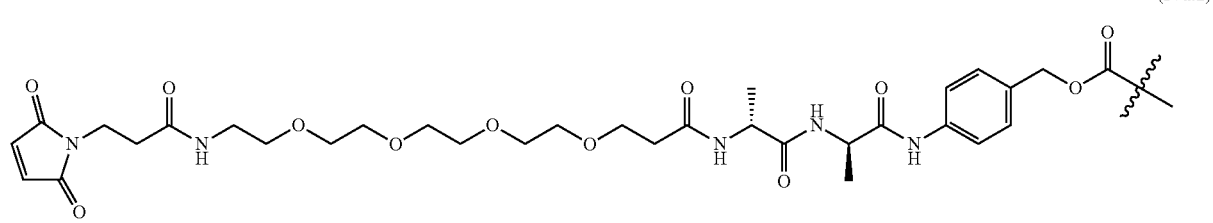

(IVa.2)

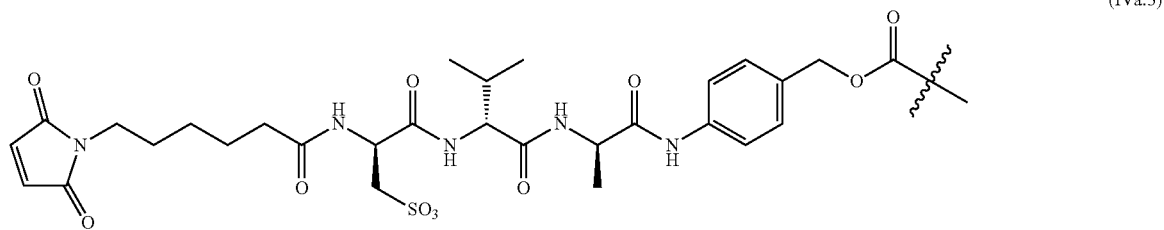

(IVa.3)

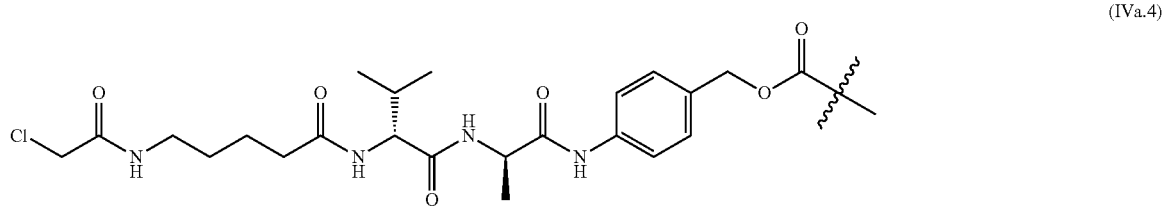

(IVa.4)

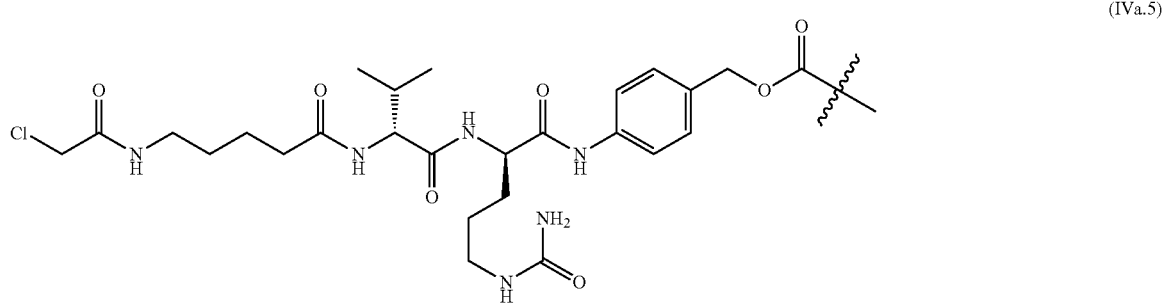

(IVa.5)

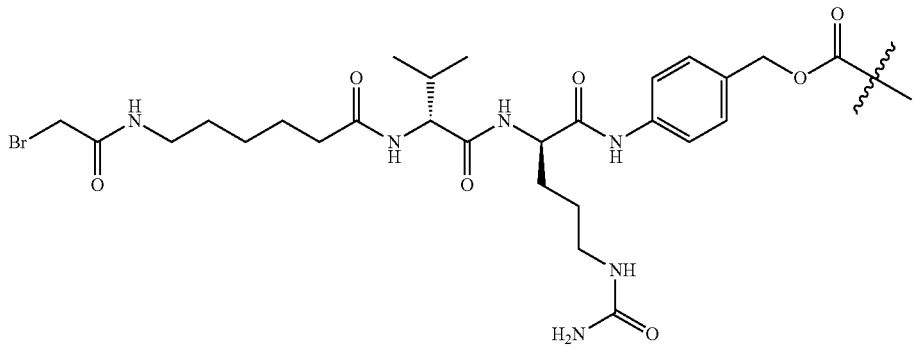
(IVa.6)
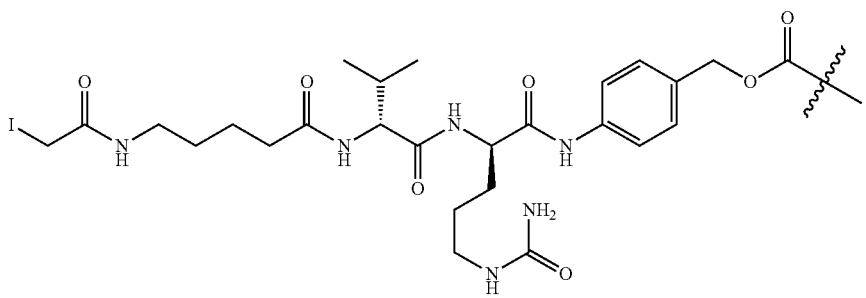
(IVa.7)
Specific exemplary embodiments of linkers according to structural formula (IVb) that may be included in the anti-glyco-MUC1 ADCs of the disclosure include the linkers illustrated below (as illustrated, the linkers include a group suitable for covalently linking the linker to an antibody):
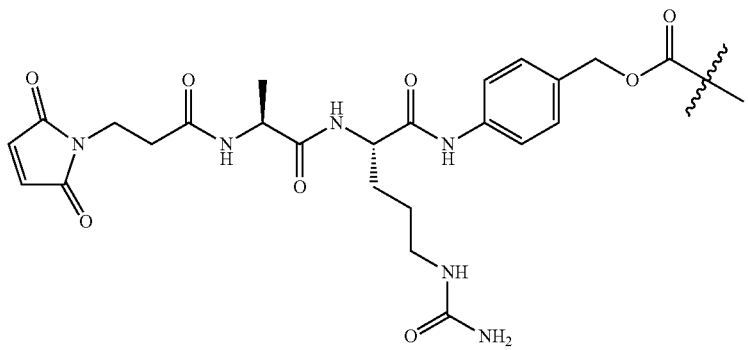
(IVb.1)
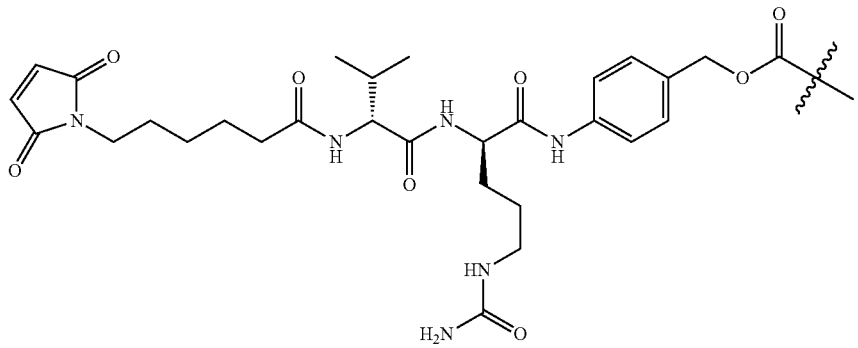
(IVb.2)

-continued
(IVb.3)
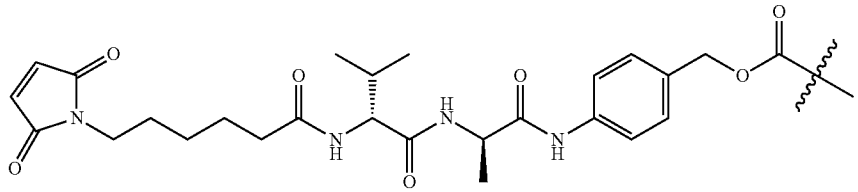
(IVb.4)
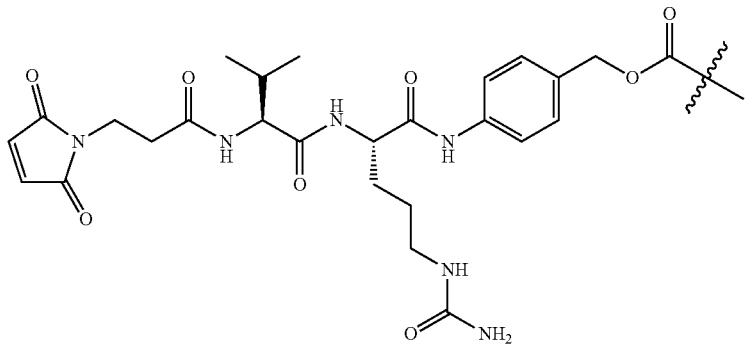
(IVb.5)
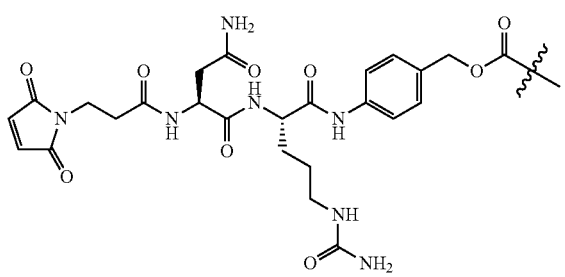
(IVb.6)
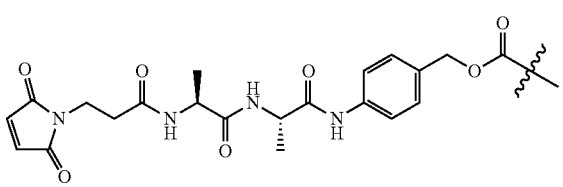
(IVb.7)
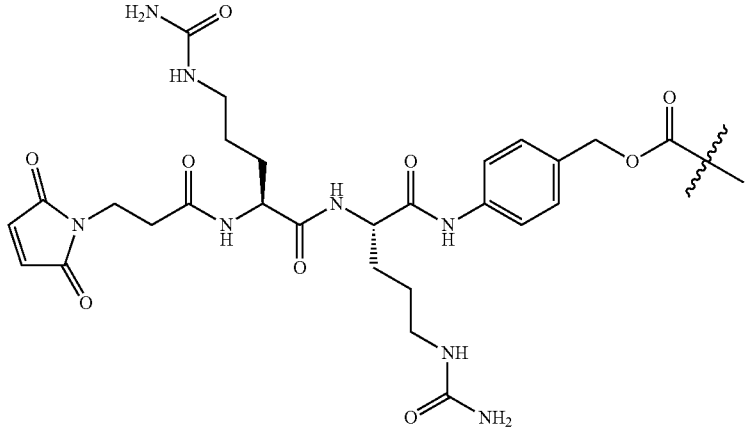
(IVb.8)
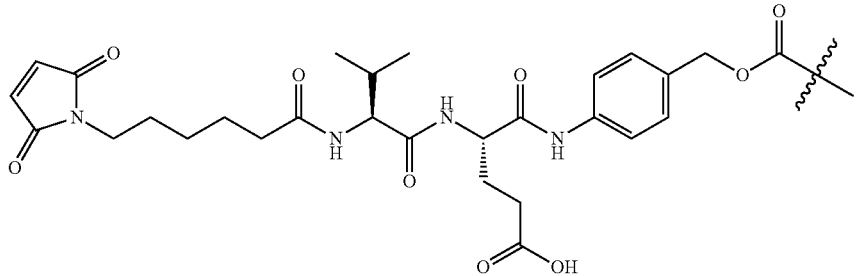

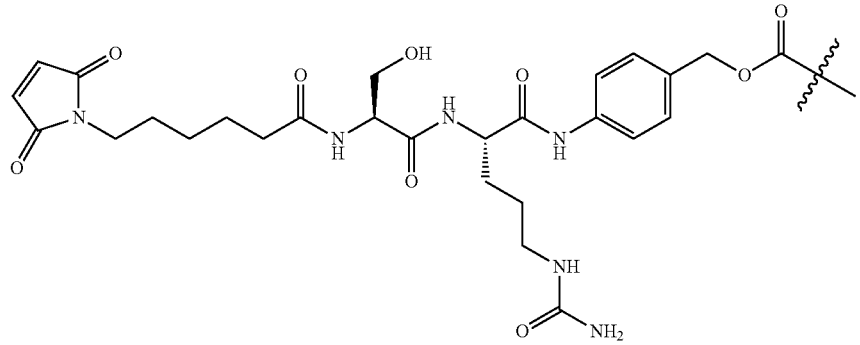
(IVb.9)
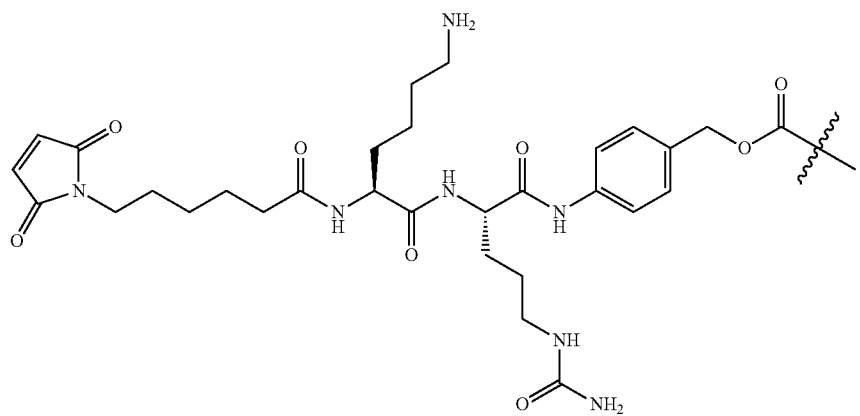
(IVb.10)
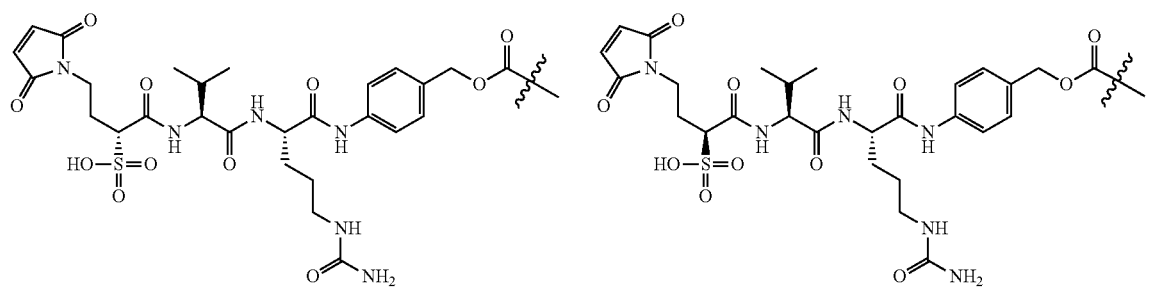
(IVb.11) (IVb.12)
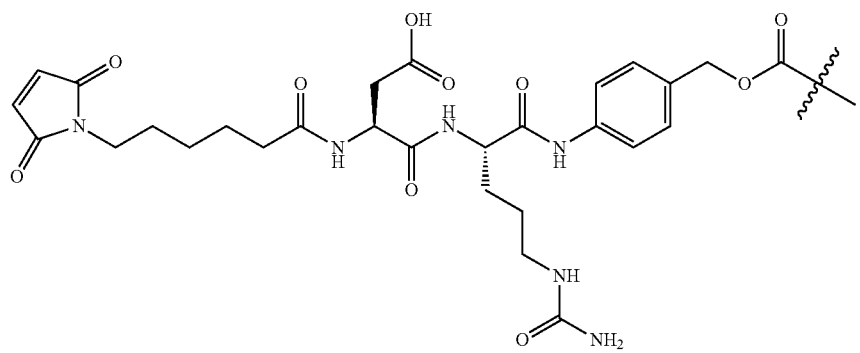
(IVb.13)

(IVb.14)
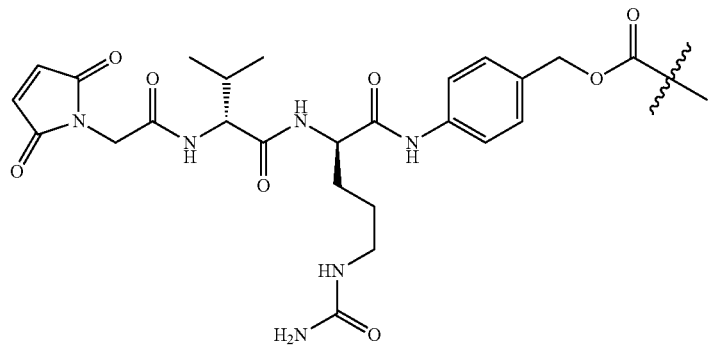
(IVb.15)
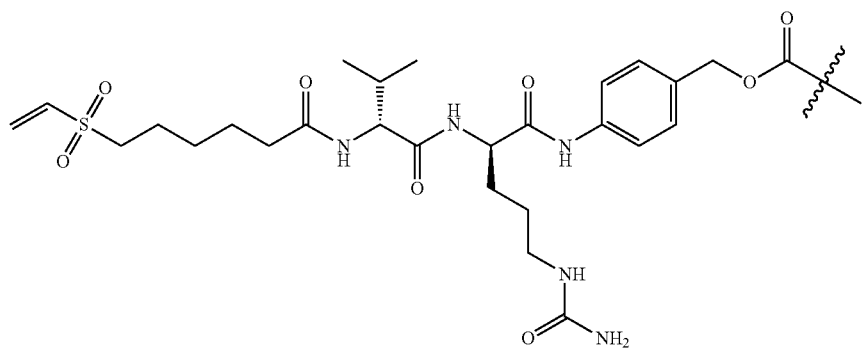
(IVb.16)
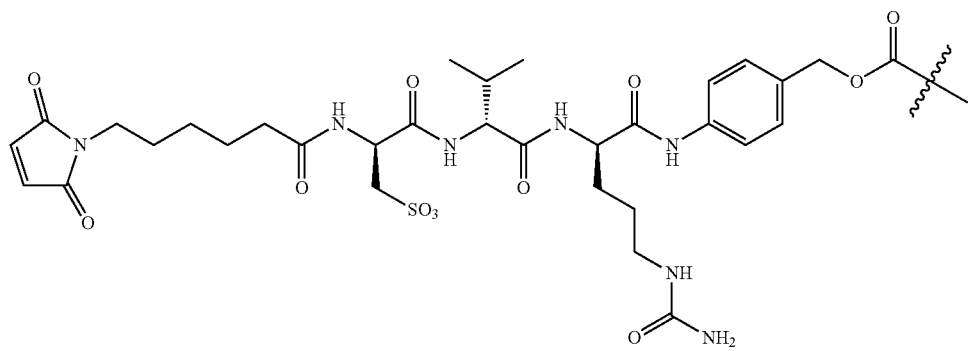
(IVb.17)
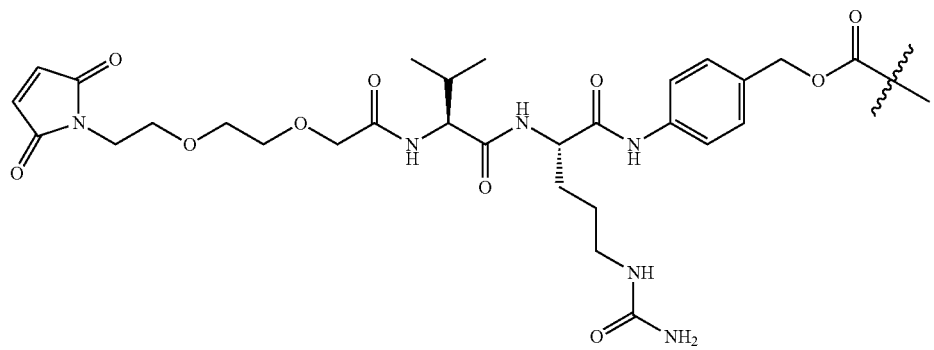

-continued

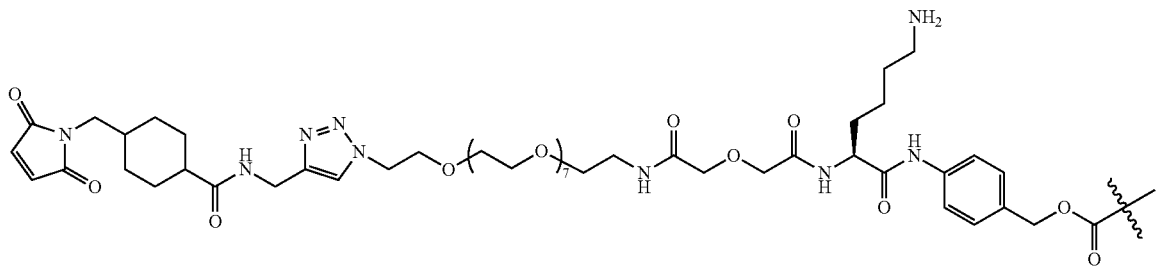

(IVb.18)

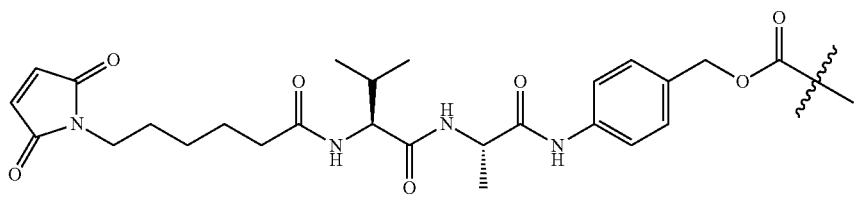

(IVb.19)

In certain embodiments, the linker comprises an enzymatically cleavable peptide moiety, for example, a linker comprising structural formula (IVc) or (IVd):

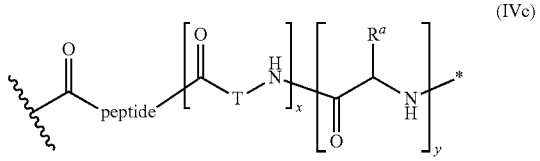

(IVc)

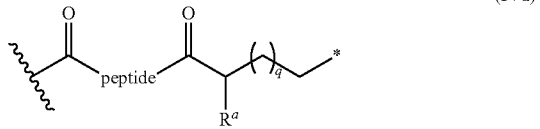

(IVd)

or a salt thereof, wherein: peptide represents a peptide (illustrated C→N and not showing the carboxy and amino "termini") cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; p is an integer ranging from 0 to 5; q is 0 or 1; x is 0 or 1; y is 0 or 1; _x ⌁ represents the point of attachment of the linker to a cytotoxic and/or cytostatic agent; and * represents the point of attachment to the remainder of the linker.

Specific exemplary embodiments of linkers according to structural formula (IVc) that may be included in the anti-glyco-MUC1 ADCs of the disclosure include the linkers illustrated below (as illustrated, the linkers include a group suitable for covalently linking the linker to an antibody):

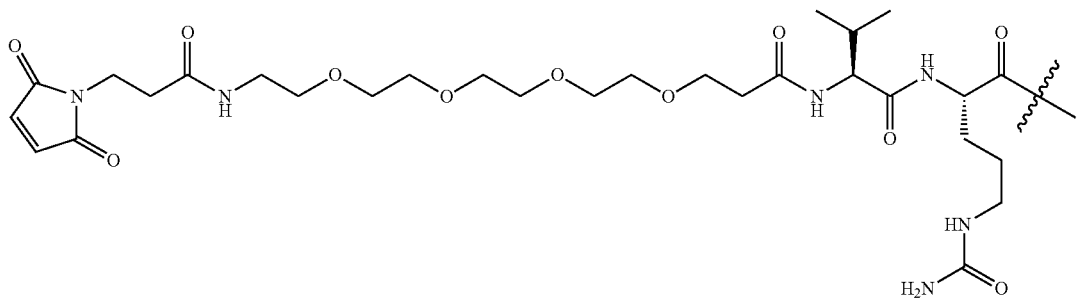

(IVc.1)

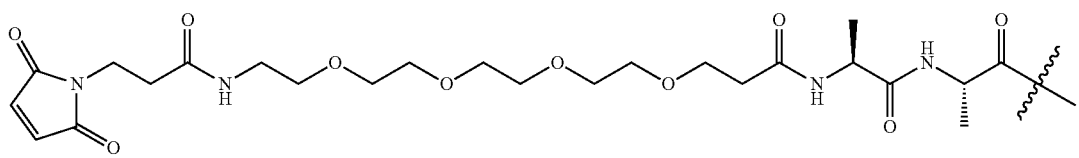

(IVc.2)

-continued
(IVc.3)
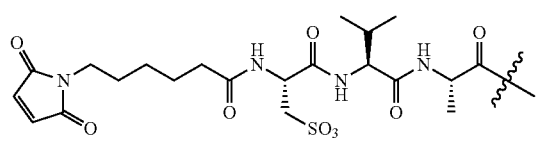
(IVc.4)
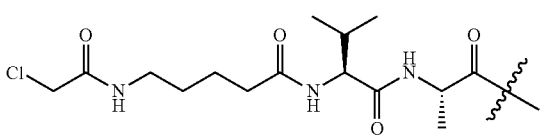
(IVC.5)
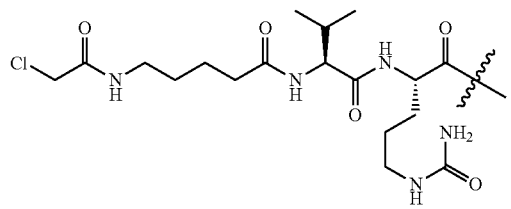
(IVc.6)
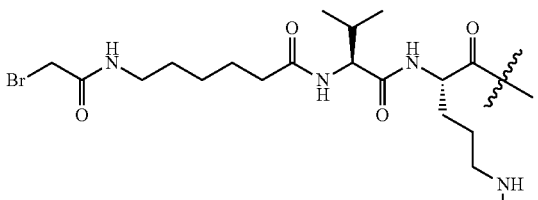
(IVc.7)
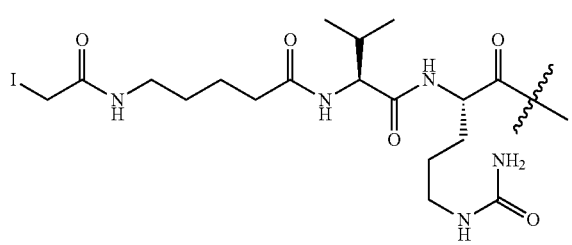
Specific exemplary embodiments of linkers according to structural formula (IVd) that may be included in the anti-glyco-MUC1 ADCs of the disclosure include the linkers illustrated below (as illustrated, the linkers include a group suitable for covalently linking the linker to an antibody):
-continued
(IVd.3)
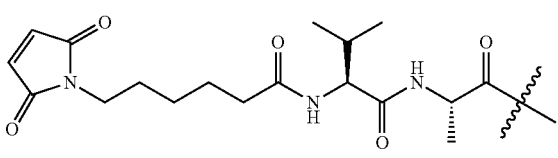
(IVd.1)
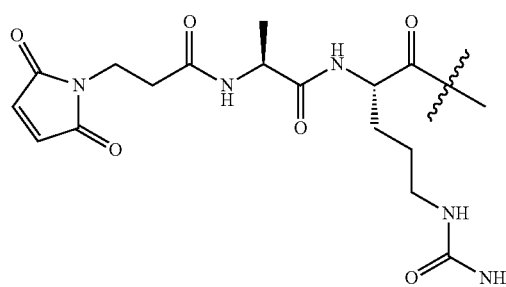
(IVd.4)
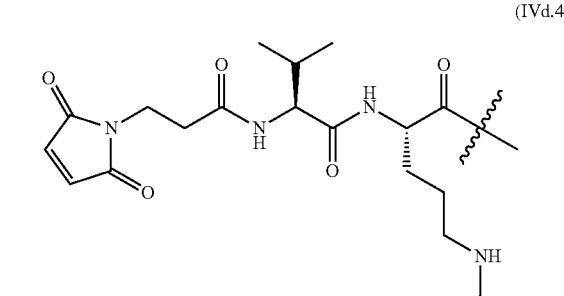
(IVd.2)
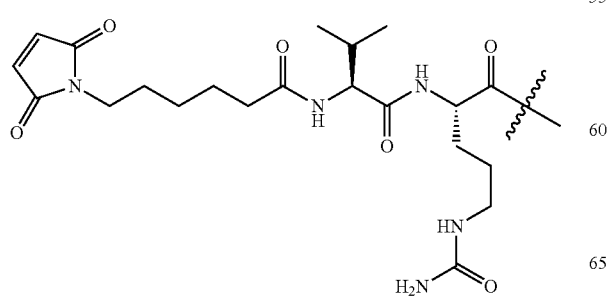
(IVd.5)
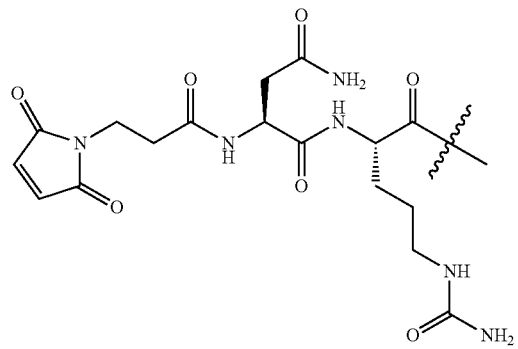

(IVd.6)
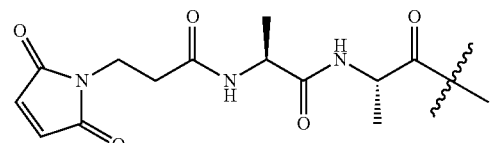
(IVd.7)
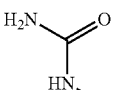
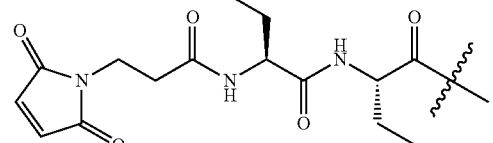
(IVd.8)
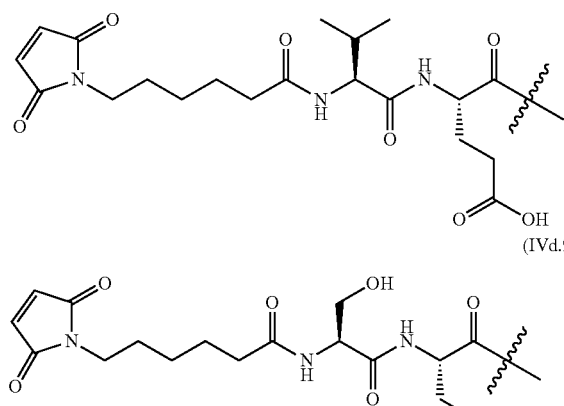
(IVd.9)
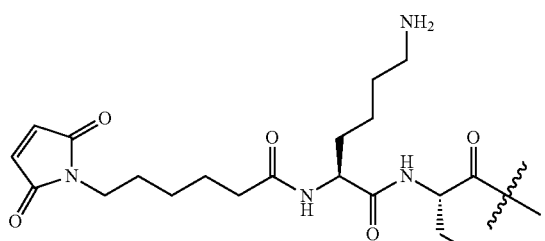
(IVd.10)
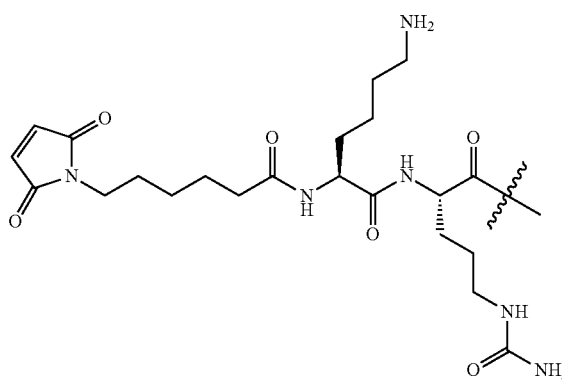
(IVd.11)
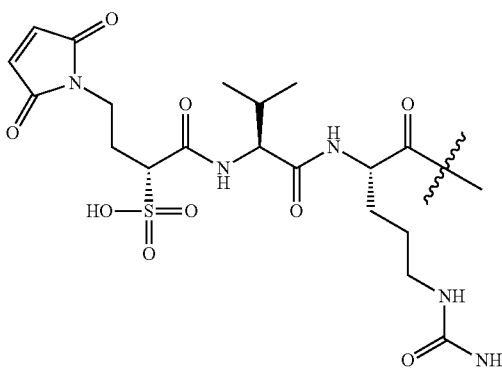
(IVd.12)
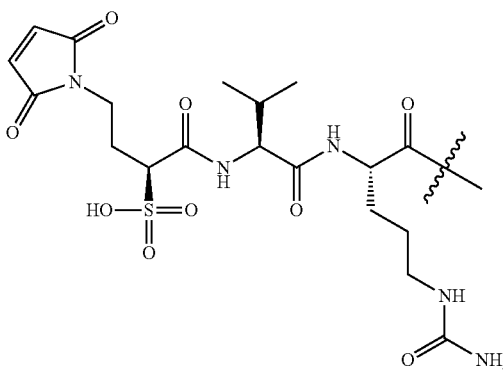
(IVd.13)
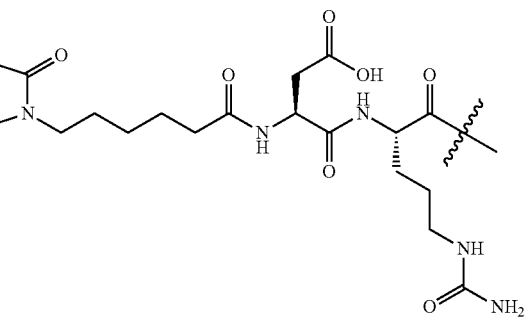
(IVd.14)

-continued (IVd.15)
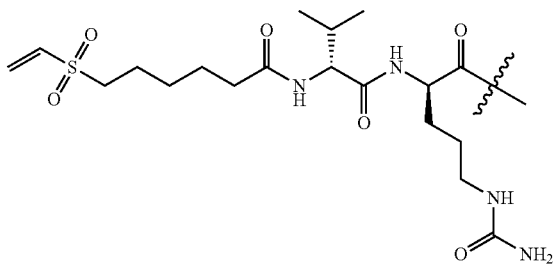

(IVd.16)
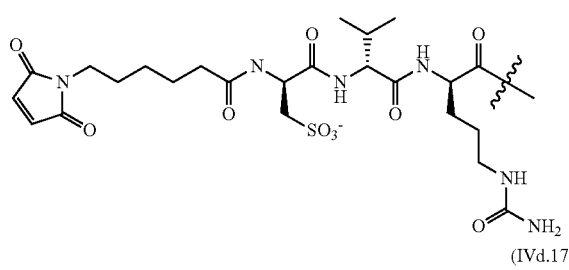

(IVd.17)
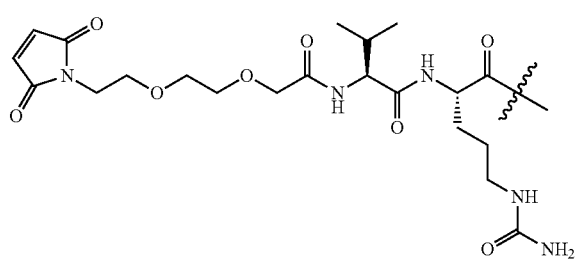

In certain embodiments, the linker comprising structural formula (IVa), (IVb), (IVc), or (IVd) further comprises a carbonate moiety cleavable by exposure to an acidic medium. In particular embodiments, the linker is attached through an oxygen to a cytotoxic and/or cytostatic agent.

6.3.4. Non-Cleavable Linkers

Although cleavable linkers may provide certain advantages, the linkers comprising the anti-glyco-MUC1 ADC of the disclosure need not be cleavable. For noncleavable linkers, the release of drug does not depend on the differential properties between the plasma and some cytoplasmic compartments. The release of the drug is postulated to occur after internalization of the ADC via antigen-mediated endocytosis and delivery to lysosomal compartment, where the antibody is degraded to the level of amino acids through intracellular proteolytic degradation. This process releases a drug derivative, which is formed by the drug, the linker, and the amino acid residue to which the linker was covalently attached. The amino acid drug metabolites from conjugates with noncleavable linkers are more hydrophilic and generally less membrane permeable, which leads to less bystander effects and less nonspecific toxicities compared to conjugates with a cleavable linker. In general, ADCs with non-cleavable linkers have greater stability in circulation than ADCs with cleavable linkers. Non-cleavable linkers may be alkylene chains, or maybe polymeric in natures, such as, for example, based upon polyalkylene glycol polymers, amide polymers, or may include segments of alkylene chains, polyalkylene glocols and/or amide polymers.

A variety of non-cleavable linkers used to link drugs to antibodies have been described. See, Jeffrey et al., 2006, Bioconjug. Chem. 17; 831-840; Jeffrey et al., 2007, Bioorg. Med. Chem. Lett. 17:2278-2280; and Jiang et al., 2005, J. Am. Chem. Soc. 127:11254-11255, each of which is incorporated herein by reference. All of these linkers may be included in the anti-glyco-MUC1 ADCs of the disclosure.

In certain embodiments, the linker is non-cleavable in vivo, for example a linker according to structural formula (VIa), (VIb), (VIc) or (VId) (as illustrated, the linkers include a group suitable for covalently linking the linker to an antibody:

(VIa)
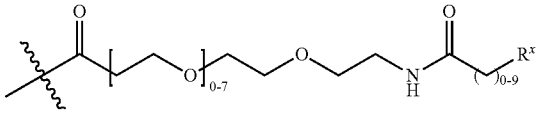

(VIb)
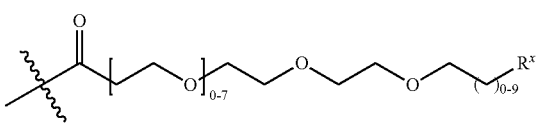

(VIc)
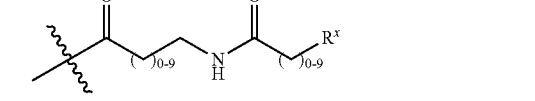

(VId)
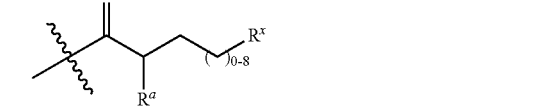

or salts thereof, wherein: $R^a$ is selected from hydrogen, alkyl, sulfonate and methyl sulfonate; $R^x$ is a moiety including a functional group capable of covalently linking the linker to an antibody; and ⁂ represents the point of attachment of the linker to a cytotoxic and/or cytostatic agent.

Specific exemplary embodiments of linkers according to structural formula (VIa)-(VId) that may be included in the anti-glyco-MUC1 ADCs of the disclosure include the linkers illustrated below (as illustrated, the linkers include a group suitable for covalently linking the linker to an antibody, and ⁂ represents the point of attachment to a cytotoxic and/or cytostatic agent):

(VIa)
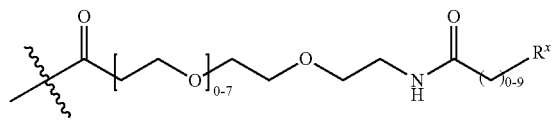

-continued

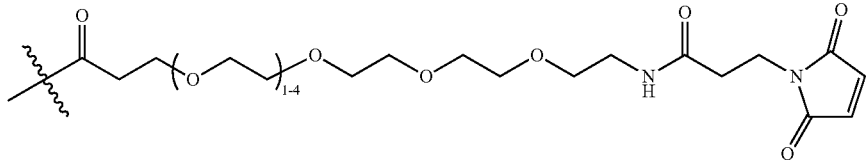
(VIa.1)

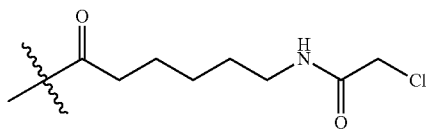
(VIc.1)

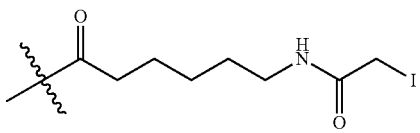
(VIc.2)

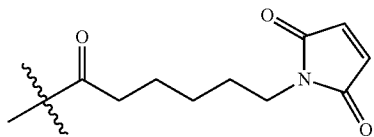
(VId.1)

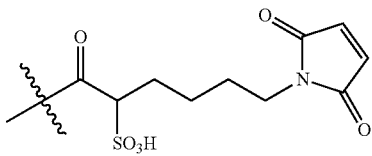
(VId.2)

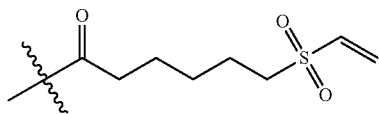
(VId.3)

6.3.5. Groups Used to Attach Linkers to Antibodies

A variety of groups may be used to attach linker-drug synthons to antibodies to yield ADCs. Attachment groups can be electrophilic in nature and include: maleimide groups, activated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure. The specific group used will depend, in part, on the site of attachment to the antibody.

One example of a "self-stabilizing" maleimide group that hydrolyzes spontaneously under antibody conjugation conditions to give an ADC species with improved stability is depicted in the schematic below. See US20130309256 A1; also Lyon et al., Nature Biotech published online, doi: 10.1038/nbt.2968.

Normal system:

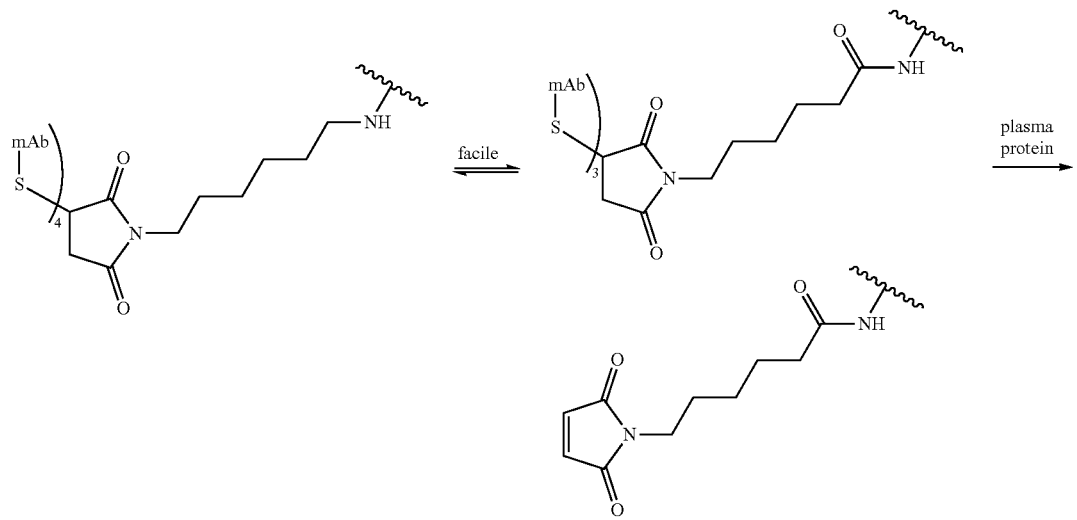

-continued

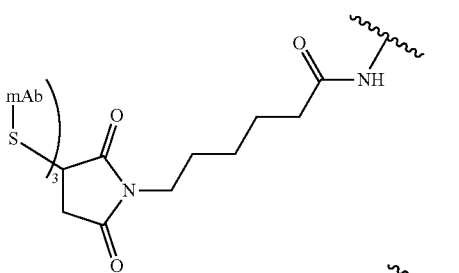

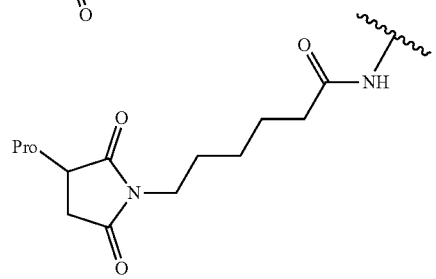

Leads to "DAR loss" over time
SGN MalDPR (maleimido dipropylamino) system:

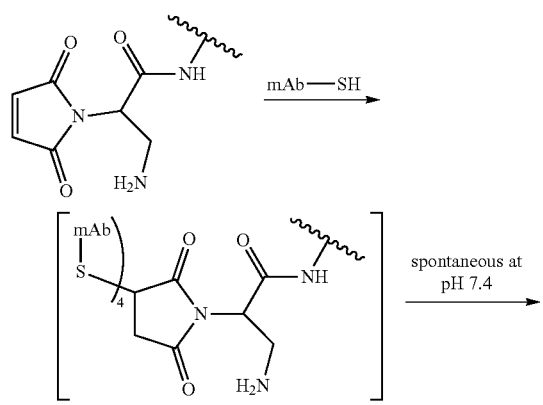

US20130309256A1

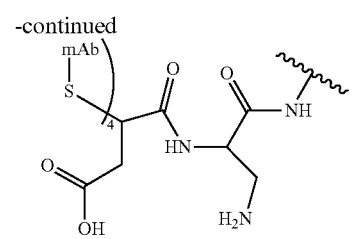

stable in plasma
(retro hetero-Michael
reaction shown above slow)

Polytherics has disclosed a method for bridging a pair of sulfhydryl groups derived from reduction of a native hinge disulfide bond. See, Badescu et al., 2014, Bioconjugate Chem. 25:1124-1136. The reaction is depicted in the schematic below. An advantage of this methodology is the ability to synthesize enriched DAR4 ADCs by full reduction of IgGs (to give 4 pairs of sulfhydryls) followed by reaction with 4 equivalents of the alkylating agent. ADCs containing "bridged disulfides" are also claimed to have increased stability.

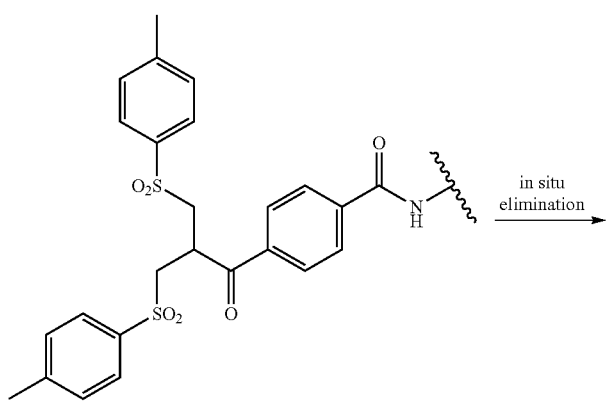

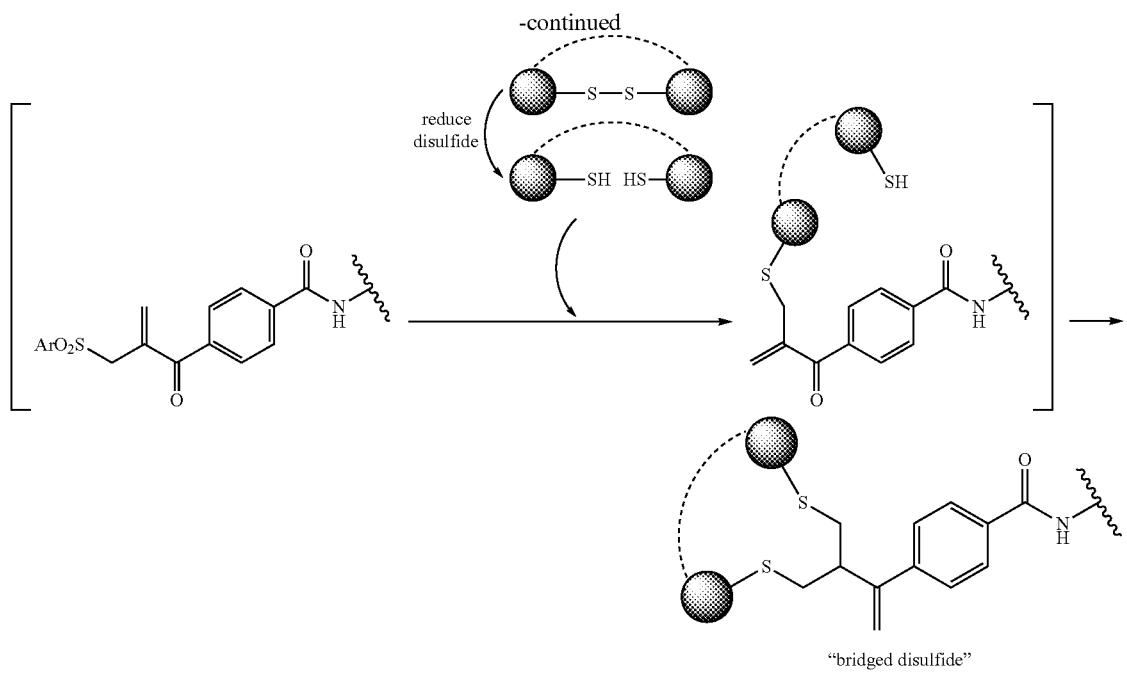

Similarly, as depicted below, a maleimide derivative (1, below) that is capable of bridging a pair of sulfhydryl groups has been developed. See WO2013/085925.

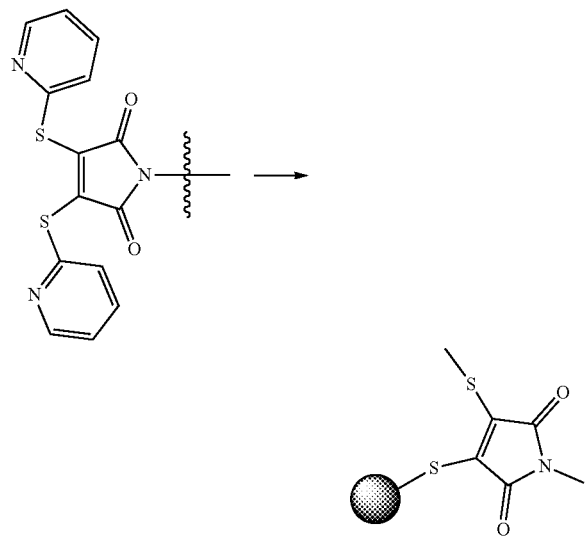

6.3.6. Linker Selection Considerations

As is known by skilled artisans, the linker selected for a particular ADC may be influenced by a variety of factors, including but not limited to, the site of attachment to the antibody (e.g., lys, cys or other amino acid residues), structural constraints of the drug pharmacophore and the lipophilicity of the drug. The specific linker selected for an ADC should seek to balance these different factors for the specific antibody/drug combination. For a review of the factors that are influenced by choice of linkers in ADCs, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013.

For example, ADCs have been observed to effect killing of bystander antigen-negative cells present in the vicinity of the antigen-positive tumor cells. The mechanism of bystander cell killing by ADCs has indicated that metabolic products formed during intracellular processing of the ADCs may play a role. Neutral cytotoxic metabolites generated by metabolism of the ADCs in antigen-positive cells appear to play a role in bystander cell killing while charged metabolites may be prevented from diffusing across the membrane into the medium and therefore cannot affect bystander killing. In certain embodiments, the linker is selected to attenuate the bystander killing effect caused by cellular metabolites of the ADC. In certain embodiments, the linker is selected to increase the bystander killing effect.

The properties of the linker may also impact aggregation of the ADC under conditions of use and/or storage. Typically, ADCs reported in the literature contain no more than 3-4 drug molecules per antibody molecule (see, e.g., Chari, 2008, Acc Chem Res 41:98-107). Attempts to obtain higher drug-to-antibody ratios ("DAR") often failed, particularly if both the drug and the linker were hydrophobic, due to aggregation of the ADC (King et al., 2002, J Med Chem 45:4336-4343; Hollander et al., 2008, Bioconjugate Chem 19:358-361; Burke et al., 2009 Bioconjugate Chem 20:1242-1250). In many instances, DARs higher than 3-4 could be beneficial as a means of increasing potency. In instances where the cytotoxic and/or cytostatic agent is hydrophobic in nature, it may be desirable to select linkers that are relatively hydrophilic as a means of reducing ADC aggregation, especially in instances where DARS greater than 3-4 are desired. Thus, in certain embodiments, the linker incorporates chemical moieties that reduce aggregation of the ADCs during storage and/or use. A linker may incorporate polar or hydrophilic groups such as charged groups or groups that become charged under physiological pH to reduce the aggregation of the ADCs. For example, a linker may incorporate charged groups such as salts or groups that deprotonate, e.g., carboxylates, or protonate, e.g., amines, at physiological pH.

Exemplary polyvalent linkers that have been reported to yield DARs as high as 20 that may be used to link numerous cytotoxic and/or cytostatic agents to an antibody are described in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the content of which are incorporated herein by reference in their entireties.

In particular embodiments, the aggregation of the ADCs during storage or use is less than about 10% as determined by size-exclusion chromatography (SEC). In particular embodiments, the aggregation of the ADCs during storage or use is less than 10%, such as less than about 5%, less than about 4%, less than about 3%, less than about 2%, less than about 1%, less than about 0.5%, less than about 0.1%, or even lower, as determined by size-exclusion chromatography (SEC).

6.3.7. Methods of Making Anti-Glyco-MUC1 ADCs

The anti-glyco-MUC1 ADCs of the disclosure may be synthesized using chemistries that are well-known. The chemistries selected will depend upon, among other things, the identity of the cytotoxic and/or cytostatic agent(s), the linker and the groups used to attach linker to the antibody. Generally, ADCs according to formula (I) may be prepared according to the following scheme:

$$D\text{-}L\text{-}R^x + Ab\text{-}R^y \rightarrow [D\text{-}L\text{-}XY]_n\text{-}Ab \qquad (I)$$

where D, L, Ab, XY and n are as previously defined, and $R^x$ and $R^y$ represent complementary groups capable of forming a covalent linkages with one another, as discussed above.

The identities of groups $R^x$ and $R^y$ will depend upon the chemistry used to link synthon D-L-$R^x$ to the antibody. Generally, the chemistry used should not alter the integrity of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: Monoclonal Antibodies And Cancer Therapy, Reisfeld et al. Eds., Alan R. Liss, Inc., 1985; Hellstrom et al., "Antibodies For Drug Delivery," in: Controlled Drug Delivery, Robinson et al. Eds., Marcel Dekker, Inc., 2nd Ed. 1987; Thorpe, "Antibody Carriers Of Cytotoxic Agents In Cancer Therapy: A Review," in: Monoclonal Antibodies '84: Biological And Clinical Applications, Pinchera et al., Eds., 1985; "Analysis, Results, and Future Prospective of the Therapeutic Use of Radiolabeled Antibody In Cancer Therapy," in: Monoclonal Antibodies For Cancer Detection And Therapy, Baldwin et al., Eds., Academic Press, 1985; Thorpe et al., 1982, Immunol. Rev. 62:119-58; PCT publication WO 89/12624. Any of these chemistries may be used to link the synthons to an antibody.

A number of functional groups $R^x$ and chemistries useful for linking synthons to accessible lysine residues are known, and include by way of example and not limitation NHS-esters and isothiocyanates.

A number of functional groups $R^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups $R^x$ suitable for covalently linking the synthons to these "converted" functional groups are then included in the synthons.

The antibody may also be engineered to include amino acid residues for conjugation. An approach for engineering antibodies to include non-genetically encoded amino acid residues useful for conjugating drugs in the context of ADCs is described by Axup et al., 2012, Proc Natl Acad Sci USA. 109(40):16101-16106, as are chemistries and functional group useful for linking synthons to the non-encoded amino acids.

Typically, the synthons are linked to the side chains of amino acid residues of the antibody, including, for example, the primary amino group of accessible lysine residues or the sulfhydryl group of accessible cysteine residues. Free sulfhydryl groups may be obtained by reducing interchain disulfide bonds.

For linkages where $R^y$ is a sulfhydryl group (for example, when $R^x$ is a maleimide), the antibody is generally first fully or partially reduced to disrupt interchain disulfide bridges between cysteine residues.

Cysteine residues that do not participate in disulfide bridges may engineered into an antibody by mutation of one or more codons. Reducing these unpaired cysteines yields a sulfhydryl group suitable for conjugation. Preferred positions for incorporating engineered cysteines include, by way of example and not limitation, positions S112C, S113C, A114C, S115C, A176C, S180C, S252C, V286C, V292C, S357C, A359C, S398C, S428C (Kabat numbering) on the human $IgG_1$ heavy chain and positions V110C, S114C, S121C, S127C, S168C, V205C (Kabat numbering) on the human Ig kappa light chain (see, e.g., U.S. Pat. Nos. 7,521,541, 7,855,275 and 8,455,622).

As will appreciated by skilled artisans, the number of cytotoxic and/or cytostatic agents linked to an antibody molecule may vary, such that a collection of ADCs may be heterogeneous in nature, where some antibodies contain one linked agent, some two, some three, etc. (and some none). The degree of heterogeneity will depend upon, among other things, the chemistries used for linking the cytotoxic and/or cytostatic agents. For example, where the antibodies are reduced to yield sulfhydryl groups for attachment, heterogeneous mixtures of antibodies having zero, 2, 4, 6 or 8 linked agents per molecule are often produced. Furthermore, by limiting the molar ratio of attachment compound, antibodies having zero, 1, 2, 3, 4, 5, 6, 7 or 8 linked agents per molecule are often produced. Thus, it will be understood that depending upon context, stated DARs may be averages for a collection of antibodies. For example, "DAR4" can refer to an ADC preparation that has not been subjected to purification to isolate specific DAR peaks and can comprise a heterogeneous mixture of ADC molecules having different numbers of cytostatic and/or cytotoxic agents attached per antibody (e.g., 0, 2, 4, 6, 8 agents per antibody), but has an average drug-to-antibody ratio of 4. Similarly, in some embodiments, "DAR2" refers to a heterogeneous ADC preparation in which the average drug-to-antibody ratio is 2.

When enriched preparations are desired, antibodies having defined numbers of linked cytotoxic and/or cytostatic agents may be obtained via purification of heterogeneous mixtures, for example, via column chromatography, e.g., hydrophobic interaction chromatography.

Purity may be assessed by a variety of methods, as is known in the art. As a specific example, an ADC preparation may be analyzed via HPLC or other chromatography and the purity assessed by analyzing areas under the curves of the resultant peaks.

6.4 Chimeric Antigen Receptors

The present disclosure provides chimeric antigen receptors (CARs) comprising the anti-glyco-MUC1 antibodies or antigen-binding fragments described herein.

The CARs of the disclosure typically comprise an extracellular domain operably linked to a transmembrane domain which is in turn operably linked to an intracellular domain for signaling.

The extracellular domains of the CARs of the disclosure comprise the sequence of an anti-glyco-MUC1 antibody or antigen-binding fragment (e.g., as described in Section 6.1 or embodiments 1 to 90).

Exemplary transmembrane domain sequence and intracellular domain sequences are described in Section 6.4.1 and 6.4.2, respectively.

Several fusion proteins described herein (e.g., embodiments 92 and 94-96) are CARs, and the CAR-related disclosures apply to such fusion proteins.

6.4.1. Transmembrane Domain

With respect to the transmembrane domain, the CAR can be designed to comprise a transmembrane domain that is operably linked (e.g., fused) to the extracellular domain of the CAR.

The transmembrane domain may be derived either from a natural or from a synthetic source. Where the source is natural, the domain may be derived from any membrane-bound or transmembrane protein. Transmembrane regions of particular use in this disclosure may be derived from (i.e., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain is synthetic (i.e., non-naturally occurring). Examples of synthetic transmembrane domains are peptides comprising predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the disclosure is the CD8 transmembrane domain. In one embodiment, the CD8 transmembrane domain comprises the amino acid sequence YLHLGALGRDLWGPSPVTGYHPLL (SEQ ID NO:53).

In one embodiment, the transmembrane domain in the CAR of the disclosure is the CD28 transmembrane domain. In one embodiment, the CD28 transmembrane domain comprises the amino acid sequence FWVLVVVGGVLACYSLLVTVAFIIFWV (SEQ ID NO:54).

In some instances, the transmembrane domain of the CAR of the disclosure comprises the CD8a hinge domain. In one embodiment, the CD8a hinge domain comprises the amino acid sequence TTTPAPRPPTPAPTIASQPLSLRPEACRPAAGGAVHTRGLDFAC (SEQ ID NO:55).

6.4.2. Intracellular Domain

The intracellular signaling domain of the CAR of the disclosure is responsible for activation of at least one of the normal effector functions of the immune cell in which the CAR is expressed. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through the TCR alone may be insufficient for full activation of the T cell and a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs of the disclosure include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the disclosure comprises a cytoplasmic signaling sequence from CD3-zeta.

In a preferred embodiment, the cytoplasmic domain of the CAR is designed to include an ITAM containing primary cytoplasmic signaling sequences domain (e.g., that of CD3-zeta) by itself or combined with any other desired cytoplasmic domain(s) useful in the context of the CAR of the disclosure. For example, the cytoplasmic domain of the CAR can include a CD3 zeta chain portion and a costimulatory signaling region.

The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR of the disclosure may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB.

6.5 Nucleic Acids, Recombinant Vectors and Host Cells

The present disclosure encompasses nucleic acid molecules encoding immunoglobulin light and heavy chain genes for anti-glyco-MUC1 antibodies, vectors comprising such nucleic acids, and host cells capable of producing the anti-glyco-MUC1 antibodies of the disclosure. In certain aspects, the nucleic acid molecules encode, and the host cells are capable of expressing, the anti-glyco-MUC1 antibodies and antibody-binding fragments of the disclosure (e.g., as described in Section 6.1 and embodiments 1 to 90) as well as fusion proteins (e.g., as described in embodiments 91-96) and chimeric antigen receptors (e.g., as described in Section 6.4 and embodiments 97-98) containing them. Exemplary vectors of the disclosure are described in embodiments 111-113 and exemplary host cells are described in embodiments 114-117.

An anti-glyco-MUC1 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel, F. M. et al., eds., Greene Publishing Associates, 1989) and in U.S. Pat. No. 4,816,397.

To generate nucleic acids encoding such anti-glyco-MUC1 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-glyco-MUC1 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_H$- or $V_L$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region.

To create a scFv gene, the $V_H$- and $V_L$-encoding DNA fragments can be operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_H$ and $V_L$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-glyco-MUC1 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-glyco-MUC1 antibody-related light or heavy chain sequences, the expression vector can already carry antibody constant region sequences. For example, one approach to converting the anti-glyco-MUC1 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE—dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-glyco-MUC1 antibody of this disclosure.

For expression of a CAR of the disclosure, for example as described in Section 6.4 and in embodiments 97 and 98, it is preferably that the host cell is a T cell, preferably a human T cell. In some embodiments, the host cell exhibits an anti-tumor immunity when the cell is cross-linked with MUC1 on a tumor cell. Detailed methods for producing the T cells of the disclosure are described in Section 6.5.1

Recombinant DNA technology can also be used to remove some or all of the DNA encoding either or both of the light and heavy chains that is not necessary for binding to glyco-MUC1. The molecules expressed from such truncated DNA molecules are also encompassed by the antibodies of the disclosure.

For recombinant expression of an anti-glyco-MUC1 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-glyco-MUC1 antibody, further alterations or mutations can be introduced into the coding sequence, for example to generate nucleic acids encoding antibodies with different CDR sequences, antibodies with reduced affinity to the Fc receptor, or antibodies of different subclasses.

The anti-glyco-MUC1 antibodies of the disclosure can also be produced by chemical synthesis (e.g., by the methods described in Solid Phase Peptide Synthesis, 2nd ed., 1984 The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-glyco-MUC1 antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-glyco-MUC1 antibodies of the present disclosure and/or binding fragments can be fused to heterologous polypeptide sequences described herein or otherwise known in the art to facilitate purification.

Once isolated, the anti-glyco-MUC1 antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

6.5.1. Recombinant Production of CARs in T Cells

In some embodiments, nucleic acids encoding the anti-glyco-MUC1 CARs of the disclosure are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transponsons.

One advantage of RNA transfection methods of the disclosure is that RNA transfection is essentially transient and a vector-free: an RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly (A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

6.5.1.1 Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. Preferably, subjects are human.

T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art, may be used. In certain embodiments of the present disclosure, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the disclosure, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturers instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28'$, $CD4^+$, $CD8^+$, $CD45RA^+$ and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or, lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11 b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present disclosure.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation or T cell ablative therapy using either chemotherapy agents such as, fludarabine, external-beam radiation therapy (XRT), cyclophosphamide.

In a further embodiment of the present disclosure, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

6.5.1.2 Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the disclosure are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain embodiments of the disclosure, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type.

In further embodiments of the present disclosure, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present disclosure, the mixture may be cultured for several hours (about 3 hours) to about 14 days or any hourly integer value in between. In another embodiment, the mixture may be cultured for 21 days. In one embodiment of the disclosure the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of Tc cells. Accordingly, depending on the purpose of treatment, infusing a subject with a T cell population comprising predominately of $T_H$ cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

6.6 Compositions

The anti-glyco-MUC1 antibodies and/or anti-glyco-MUC1 ADCs of the disclosure may be in the form of compositions comprising the anti-glyco-MUC1 antibody and/or ADC and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and/or ADC and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an anti-glyco-MUC1 antibody and/or anti-glyco-MUC1 ADC of the disclosure per dose. The quantity of antibody and/or ADC included in a unit dose will depend on the disease being treated, as well as other factors as are well known in the art. Such unit dosages may be in the form of a lyophilized dry powder containing an amount of antibody and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of antibody and/or ADC suitable for a single administration.

The pharmaceutical compositions may also be supplied in bulk from containing quantities of ADC suitable for multiple administrations.

Pharmaceutical compositions may be prepared for storage as lyophilized formulations or aqueous solutions by mixing an antibody and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of ADC.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.7 Methods of Use

The anti-glyco-MUC1 antibody or binding fragments described herein can be used in various diagnostic assays. For example, the antibodies and binding fragments can be employed in immunoassays, such as competitive binding assays, direct and indirect sandwich assays, and immunoprecipitation assays, including immunohistochemistry, enzyme-linked immunosorbent assay (ELISA), fluorescence-activated cell sorting (FACS), and Western blots.

The anti-glyco-MUC1 antibody or binding fragments described herein also are useful for radiographic in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies.

The anti-glyco-MUC1 antibody or binding fragments, ADCs and CARs described herein are useful for treatment of glyco-MUC1 expressing cancers, particularly epithelial cancers such as breast cancer, ovarian cancer, pancreatic cancer, and lung cancer.

When using the CARs of the disclosure for therapy, the therapeutic methods of the disclosure comprising administering to a subject with a glyco-MUC1-expressing tumor an effective amount of a genetically modified cell engineered to express a CAR of the disclosure, for example as described in Section 6.4 or in embodiment 97 or embodiment 98. Methods of modifying cells, particularly T cells, to express a CAR, are described in Section 6.5.1.

7. EXAMPLES

7.1 Example 1: Identification Of Anti-Glyco-Muc1 Antibodies 7.1.1. Overview

Chemoenzymatic synthesis of multiple-repeat MUC1 glycopeptides with different O-glycan density and Tn (GalNAcα1-P-Ser/Thr) glycoforms was developed using recombinant glycosyltransferases. Different polypeptide GalNAc-transferase isoforms were used to direct sites of O-glycan occupancy (Bennett et al., 1998). The optimal vaccine design was found to be Tn glycoforms with high O-glycan density, and glycopeptides conjugated to KLH were found to overcome tolerance. In wild-type Balb/c mice, the glycopeptides with complete O-glycan occupancy elicited the strongest antibody response reacting with MUC1 expressed in breast cancer cell lines, thus representing the most effective vaccine design. The elicited humoral immune response showed remarkable specificity for cancer cells.

7.1.2. Materials and Methods 7.1.2.1 Chemoenzymatic Synthesis of Multimeric Tn MUC1 Glycopeptides MUC1 60-mer (VTSAPDTRPAPGSTAPPAHG)n=3 (SEQ ID NO:47) peptide was synthesized, as originally reported by Fontenot et al., 1993. Control peptides used were derived from tandem repeats (TRs) of MUC2 (PTTT-PISTTTMVTPTPTPTC) (SEQ ID NO:51) and MUC4 (CPLPVTDTSSASTGHATPLPV) (SEQ ID NO:52). Peptides were glycosylated in vitro using purified recombinant human glycosyltransferases polypeptides GalNAc-T2, GalNAc-T4, and GalNAc-T1 (Bennett et al., 1998; Schwientek et al., 2002) as described in U.S. Pat. No. 6,465,220. GalNAc glycosylation of the peptides was performed in a reaction mixture (1 mg peptide/mL) containing 25 mM cacodylate buffer (pH 7.4), 10 mM MnCl2, 0.25% Triton X-100, and 2 mM UDP-GalNAc. Glycosylation of 1 mg 60-mer peptide with two GalNAc per TR (MUC160Tn6) was obtained using GalNAc-T1. Incorporation of three GalNAc per TR (MUC160Tn9) was obtained using GalNAc-T2. Substitution of all five putative O-glycosylation sites in the MUC1 TR (MUC160Tn15) was performed using MUC160Tn9 as substrate in a reaction with GalNAc-T4. Glycosylation was monitored using nano-scale reversed-phase columns (Poros R3, PerSeptive Biosystems, Framingham, MA) and MALDI-TOF mass spectrometry. The glycopeptides were purified by high-performance liquid chromatography (HPLC) on a Zorbax 300SB-C3 column (9.4 mm×25 cm) (Agilent Technologies, Palo Alto, CA) in an 1100 Hewlett Packard system (Avondale, PA) using 0.1% trifluoroacetic acid (TFA) and a gradient of 0-80% acetonitrile. Quantification and estimation of yields of glycosylation reactions were performed by comparison of HPLC peaks by UV 210 absorbance using 10 µg weighed peptide as standard. GalNAc glycosylation of peptides generally yielded 80-90% recovery. Purified glycopeptides were characterized by MALDI-TOF mass spectrometry on a Voyager DE or Voyager DE Pro MALDI-TOF mass spectrometer (PerSeptive Biosystems) equipped with delayed extraction. The MALDI matrix was 2,5-dihydroxybenzoic acid 10 g/L (Aldrich, Milwaukee, WI) dissolved in 2:1 mixture of 0.1% TFA in 30% aqueous acetonitrile. Samples dissolved in 0.1% TFA to a concentration of ~1 µmol/uL were prepared for analysis by placing 1 µL of sample solution on a probe tip followed by 1 uL of matrix. All mass spectra were obtained in the linear mode. Data processing was carried out using GRAMS/386 software (Galactic Industries, Salem, NH).

7.1.2.2 Immunization Protocol

Glycopeptides were coupled to KLH (Pierce, Rockford, IL) using glutaraldehyde. Efficiency of conjugation was assessed by analyzing the reaction by size exclusion chromatography on a PD-10 column using anti-MUC1 ELISA of fractions. Essentially all reactivity was found with the excluded fraction and insignificant reactivity in the included fractions expected to contain peptides. Further evaluation included comparative titration analysis of the KLH conjugate with the corresponding glycopeptide in ELISA. Both analyses indicated that the conjugation was near complete, which should result in a KLH to glycopeptide ratio of 1:300. Female Balb/c wild-type mice were injected subcutaneously with 10 or 15 μg of (glyco)peptide in a total volume of 200 uL (1:1 mix with Freunds adjuvant, Sigma). Mice received four immunizations 14 days apart, and blood samples were obtained by tail or eye bleeding 1 week following the third and fourth immunization.

7.1.2.3 Generation of Mouse MAb anti-Tn-MUC1

A MAb was produced, from a wild-type Balb/c mouse immunized with the fully GalNAc-glycosylated 60-mer MUC1 glycopeptide coupled to KLH. Screening was based on glycopeptide ELISA followed by immunocytology with breast cancer cell lines (MCF7 and T47D) and immunohistology with cancer tissues. Selection was based on reactivity pattern similar to total sera of the same mouse.

7.1.2.4 ELISA

ELISA were performed using 96-well MaxiSorp plates (Nunc, Denmark). Plates were coated overnight at 4° C. with 1 μg/mL of glycopeptides in bicarbonate-carbonate buffer (pH 9.6), blocked with 5% bovine serum albumin (BSA) in phosphate-buffered saline (PBS), followed by incubation with sera (diluted in PBS) or MAbs for 2 h at room temperature. Bound antibodies were detected with peroxidase-conjugated rabbit anti-mouse immunoglobulins (Dako-Cytomation, Glostrup, Denmark) or isotype-specific antibodies peroxidase-conjugated goat anti-mouse IgM, IgG1, IgG2a, IgG2b, or IgG3 (Southern Biotechnology Associates, Birmingham, AL). Plates were developed with O-phenylenediamine tablets (DakoCytomation) and read at 492 nm. Control antibodies included anti-MUC1 antibodies HMFG2 and SM3 (Burchell et al., 1987) and anticarbohydrate antibodies 5F4 (Tn) and 3F1 (STn) (Mandel et al., 1991). Control sera included mice immunized with MUC4 mucin peptide linked to KLH.

7.1.3. Results

Glycopeptide specific mAbs were produced to GalNAc-MUC1 using GalNAc-MUC1 60-mer glycopeptide conjugated to KLH as immunogen. Using an ELISA assay, the generated mAb GO2 (5F7) reacted specifically with the MUC1 tandem repeat (VTSAPDTRPAPGSTAPPAHG)$_3$ (SEQ ID NO:47) that has been glycosylated in vitro using purified recombinant human glycosyltransferases GalNAc-T1, GalNAc-T2, and GalNAc-T4, with no reaction with the corresponding MUC1 peptide without GalNAc-residues or irrelevant glycopeptides with the same type of Tn glycoform. Results of the ELISA assay are shown in FIG. 1.

7.2 Example 2: Characterization of Anti-Glyco-Muc1 Antibodies

7.2.1. Overview

Monoclonal antibody GO2 (5F7) was characterized for the specificity of its binding to the Tn glycoforms of MUC1 associated with cancer cells.

7.2.2. Materials and Methods

7.2.2.1 Immunocytochemistry

Cell lines were fixed for 10 min in ice-cold acetone or in methanol:acetone. Fixed cells were incubated overnight at 5° C. with mouse sera (1:200/1:400/1:800) or MAbs, followed by incubation for 45 min at room temperature with fluorescein isothiocyanate (FITC)-conjugated rabbit anti-mouse immunoglobulins (DakoCytomation). Slides were mounted in glycerol containing p-phenylenediamine and examined in a Zeiss fluorescence microscope (Fluores-Science, Hallbergmoos, Germany).

7.2.2.2 Immunohistochemistry

Formalin fixed, paraffin wax embedded tissues of breast carcinoma were obtained. All cases were conventionally classified by histological type. The avidin-biotin peroxidase complex method was used for immunostaining. Paraffin sections were dewaxed, rehydrated, and treated with 0.5% $H_2O_2$ in methanol for 30 min. Sections were rinsed in TBS and incubated for 20 min with rabbit non-immune serum. Sections were rinsed and incubated overnight at 5° C. with primary antibody. Sections were rinsed and incubated with biotin-labeled rabbit anti-mouse serum (DakoCytomation) diluted 1:200 in TBS for 30 min, rinsed with TBS, and incubated for 1 h with avidin-biotin peroxidase complex (DakoCyto-mation). Sections were rinsed with TBS and developed with 0.05% 3,3'-diaminobenzidine tetrahydrochloride freshly prepared in 0.05 M TBS containing 0.1% $H_2O_2$. Sections were stained with hematoxylin, dehydrated, and mounted.

7.2.3. Results

Immunohistochemistry of colorectal carcinoma, pancreatic carcinoma, and invasive breast adenocarcimas were performed with GO2. Staining of colorectal cancer tissue (FIG. 2) demonstrated strong labeling of intracellular and surface structures on a large proportion of the cancer cells. In contrast no or significantly lower reactivity was seen to healthy columnar epithelial cells. The labeling in healthy cells was restricted to intracellular structures, which is expected due to the presence of large amounts of biosynthetic intermediates (GalNAc-modified glycoproteins) in cells with high secretory capacity such as colonic cumnar epithelia. A similar pattern was observed with pancreatic (FIG. 3) and breast cancer tissue (FIG. 4) with strong reactivity with cancer cells and none or limited reactivity with intracellular structures in surrounding healthy epithelia or connective tissue cells.

7.3 Example 3: Sequence Analysis of Anti-Glyco-Muc1 Antibodies mRNA from the hybridoma producing monoclonal antibody GO2 (5F7) was prepared, reverse transcribed and sequenced.

The nucleotide sequences encoding the heavy and light chain variable regions with their signal sequences are set forth in SEQ ID NO:11 and SEQ ID NO:12, respectively. The heavy and light chain variable regions encoded by SEQ ID NO:11 and SEQ ID NO:12 are set forth in SEQ ID NO:1 and SEQ ID NO:2, respectively. The predicted mature variable region sequences (following truncation of the signal peptide) are set forth in SEQ ID NO:3 and SEQ ID NO:4, respectively, and are encoded by SEQ ID NO:13 and SEQ ID NO:14, respectively. The predicted heavy chain CDR sequences (IMGT definition) are set forth in SEQ ID NOs:

5-7, respectively, and the predicted light chain CDR sequences (IMGT definition) are set forth in SEQ ID NOs: 8-10, respectively.

7.4 Example 4: Drug Delivery to Cancer Cells with Anti-Glyco-Muc1 Antibodies

7.4.1. Overview

Monoclonal antibody GO2 (5F7) was tested for its ability to deliver a cytotoxic agent to target cells.

7.4.2. Materials and Methods

OVCar human ovarian carcinoma cells were added to a 24-well cell culture plate at 1,000 cells/well. Monoclonal antibody GO2 and a secondary antibody conjugated to the antitubulin agent monomethyl auristatin F (MMAF) (anti-mFc-NC-MMAF) (Moradec catalog no. AM-101-AF) were added to the plate to give the following concentrations (in pg/ml) of GO2 and ADC:

TABLE 2

| Row | Column 1 | Column 2 | Column 3 | Column 4 | Column 5 | Column 6 |
|---|---|---|---|---|---|---|
| A | GO2: 5<br>ADC: 2.0 | GO2: 1<br>ADC: 2.0 | GO2: 0.2<br>ADC: 2.0 | GO2: 0.04<br>ADC: 2.0 | GO2: 0.008<br>ADC: 2.0 | GO2: 0<br>ADC: 2.0 |
| B | GO2: 5<br>ADC: 0.6 | GO2: 1<br>ADC: 0.6 | GO2: 0.2<br>ADC: 0.6 | GO2: 0.04<br>ADC: 0.6 | GO2: 0.008<br>ADC: 0.6 | GO2: 0<br>ADC: 0.6 |
| C | GO2: 5<br>ADC: 0.2 | GO2: 1<br>ADC: 0.2 | GO2: 0.2<br>ADC: 0.2 | GO2: 0.04<br>ADC: 0.2 | GO2: 0.008<br>ADC: 0.2 | GO2: 0<br>ADC: 0.2 |
| D | GO2: 5<br>ADC: 0 | GO2: 1<br>ADC: 0 | GO2: 0.2<br>ADC: 0 | GO2: 0.04<br>ADC: 0 | GO2: 0.008<br>ADC: 0 | GO2: 0<br>ADC: 0 |

The plate was incubated at 37° C. for 48 hours. After the 48 hour incubation, AlamarBlue® (Invitrogen) was added to each well, and fluorescence at 600 nm measured.

7.4.3. Results

Results are shown in FIG. 5. The results show that the cellular toxicity is dependent on primary antibody (GO2) concentration and presence of the antibody, and secondary ADC conjugated antibody concentration and presence. In other words, GO2 induces cellular toxicity of this cancer cell line when coupled with a secondary antibody that carries a cytotoxic agent MMAF.

7.5 Example 5: Circulating Tumor Cell Quantification with Anti-Muc1 Antibodies

7.5.1. Overview

Monoclonal antibody GO2 (5F7) was tested for its ability to be used to quantify circulating tumor cells.

7.5.2. Materials and Methods

GO2 was conjugated to a magnetic separation bead and allowed to interact with samples of different concentrations of tumor cells. Cells and beads were pulled out of solution with a magnet and washed several times to remove unbound material. GO2 that was conjugated to horseradish peroxidase was then applied to the magnetic separation beads containing bound cancer cells, incubated, and then unbound conjugated GO2 was washed away. A colorimetric reaction was performed using TNB as a substrate. The reaction was terminated with sulfuric acid and then OD 450 readings were taken on the samples.

7.5.3. Results

Results are shown in FIG. 6. The results of the assay demonstrated GO2 binding of tumor cells.

7.6 Example 6: Immunohistochemical Staining of Tumor Tissue Using Anti-Glyco-Muc1 Antibodies

7.6.1. Materials and Methods

Sections from six formalin fixed, paraffin embedded (FFPE) tissue micro arrays (TMAs) were cut at 2.5 μm thickness. TMAs from breast cancer (BC), colorectal cancer (CRC), ovarian cancer (OVC), non-small cell lung cancer (NSCLC) and prostate cancer (PrC) tumors were used in the study. 25-47 tumor tissue cores per TMA were available for evaluation. Core size was 1 mm, 2 mm or 3 mm, depending on the TMA. Each tissue core represented one patient.

Staining was performed on a Discovery XT autostainer (Ventana Medical Systems). Following antigen retrieval with cell condition 1 (CC1) solution (Ventana Medical Systems), the GO2 was applied at a concentration of 1 μg/mL in Dako green medium antibody diluent and incubated for 60 min at 37° C. Binding of GO2 to tumor cells was detected using the Optiview DAB IHC detection kit (Ventana Medical Systems) visualized in DAB (brown precipitate).

7.6.2. Results

Representative images of MUC1 positive TMA tumor cores are shown in FIG. 7. In BC and OVC TMAs, the majority of spots (>90%) showed moderate or strong binding of GO2 to tumor cells. 70% and 51% of NSCLC and CRC cases showed moderate and strong binding of the antibody to tumor cells, respectively. In prostate cancer, the antigen appeared to be less expressed. Only 28% of the spots in the TMA 1 revealed a moderate or strong staining intensity when applying GO-2. Staining patterns were always cytoplasmic and in many cases membrane-bound. An apical membrane staining pattern was observed in few cores.

7.7 Example 7: Production and Purification of an Anti-MUC1 Antibody in T-Cell Bispecific (TCB) Format

7.7.1. Materials and Methods

7.7.1.1 Expression Vector Production

The GO2 antibody was converted into TCB format, including knob-into-holes and P329G/L234A/L235A ("PGLALA") mutations in the Fc region and charged residues in the MUC1 CH1 (147E/213E; "EE") and CL (123R/124K; "RK") regions (see SEQ ID NOs: 43-46). The TCB antibody is illustrated in FIG. 8. Briefly, the variable heavy and variable light chains of GO2 mAb were synthesized (Geneart, Regensburg, Germany) and inserted into suitable expression vectors in which they are fused to the appropriate human constant heavy or human constant light chains. The expression cassettes in these vectors consist of the CMV promoter, Intron A with 5' UTR and a BGH polyadenylation site. In addition, the plasmids contain the oriP region from the Epstein Barr virus for the stable maintenance in HEK293 cells harboring the EBV nuclear antigen (EBNA).

7.7.1.2 Transient Transfection and Production

The antibodies were transiently produced in HEK293 EBNA cells using a PEI mediated transfection procedure as follows. HEK293 EBNA cells are cultivated in suspension serum free in Excell culture medium, containing 6 mM L-Glutamine. For the production of antibodies in a 500 ml shake flask, 300 million HEK293 EBNA cells are seeded 24 hours before transfection (for alternative scales all amounts were adjusted accordingly). For transfection, cells are centrifuged for 10 min at 210×g and the supernatant is replaced by pre-warmed 20 ml CD CHO medium. Expression vectors are mixed in 20 ml CD CHO medium to a final amount of 200 µg DNA. After addition of 540 µl PEI, solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% $CO_2$ atmosphere. After incubation, 160 ml Ex-Cell® medium (Sigma-Aldrich), containing 6 mM glutamine, 1.25 mM valproic acid and 12.5% Pepsoy, is added and cells are cultivated for 24 hours. One day after transfection, 12% Feed 7 (48 mL)+3 g/L glucose is added. After 7 days, cultivation supernatant is collected for purification by centrifugation for 45 min at 3000×g. The solution is sterile filtered (0.22 µm filter) and sodium azide in a final concentration of 0.01% w/v is added. The solution is then stored at 4° C.

7.7.1.3 Antibody Purification

Secreted proteins were purified by affinity chromatography using Protein A, followed by size exclusion chromatography. For affinity chromatography, the supernatant was loaded on a Protein A MabSelect SuRe column (GE Healthcare) equilibrated with 20 mM sodium phosphate, 20 mM sodium citrate pH 7.5. Unbound protein was removed by washing with equilibration buffer. The bound protein was eluted using either a step (standard IgG) or a gradient (bispecific antibody) elution created with 20 mM sodium citrate, 100 mM sodium chloride, 100 mM glycine, pH 3.0. The pH of collected fractions was adjusted by adding 1/10 (v/v) of 0.5 M sodium phosphate pH8.0. The protein was concentrated and filtered prior to loading on a HiLoad Superdex 200 column (GE Healthcare) equilibrated with 20 mM histidine, 140 mM sodium chloride, pH 6.0.

The aggregate content of eluted fractions was analyzed by analytical size exclusion chromatography. Therefore, 30 µl of each fraction was applied to a TSK G3000 SWXL column (TOSOH, 7.8 mm×30 cm) equilibrated with 200 mM Arginine, 25 mM $K_2PO_4$, 125 mM Sodium chloride, 0.02% $NaN_3$, pH 6.7. Fractions containing less than 2% oligomers were pooled and concentrated to final concentration of 1-1.5 mg/ml using centrifugal concentrators (Millipore, Amicon® ULTRA—15, 30 k MWCO). Purified proteins were stored at −80° C.

7.7.2. Results

Production yield and quality of GO2 TCB antibodies are shown in Table 5.

TABLE 5

| Molecule | Yield [mg/L] | Monomer [%] SEC | HMW [%] | LMW [%] | Purity [%] CE-SDS |
|---|---|---|---|---|---|
| GO2 TCB | 0.51 | 94.16 | 0.00 | 5.84 | 85.61 |

7.8 Example 8: Jurkat-NFAT Reporter Assay to Monitor Target Expression Ex Vivo in Undigested Patient-Derived Tumor Samples

7.8.1. Overview

A Jurkat NFAT reporter assay was used to monitor target expression (glyco-MUC1) ex vivo in undigested primary human tumor samples using a GO2 TCB.

7.8.2. Materials and Methods

7.8.2.1 Materials

GO2 TCB (see Example 7)
DP47 TCB (non-targeted, negative control)
Matrigel (Item no. 734-1101, Corning/VWR, Switzerland)
Corning® Costar® Ultra-Low attachment multiwell plates (Item no. CLS7007-24EA, Sigma)
Cell culture microplate, 96 well (Item no. 655098, Greiner Bio-one, Switzerland)
RPMI1640 Medium (Item no. 42401-018, FisherScientific, Schweiz)
Jurkat Medium: RPM11640 Medium with 2 g/l D-Glucose, 2 g/l $NaHCO_3$, 10% FCS, 25 mM HEPES, 2 mM L-Glutamine, 1×NEAA, 1×Sodium-Pyruvate, 200 µg/ml Hygromycine B
Jurkat NFAT luciferase reporter cells (Promega)
Tumor samples received from Indivumed GmbH, Germany. Samples were shipped over night in transport medium. About 24 h after surgery the samples were cut in small pieces.

7.8.2.2 Methods 96-well cell culture microplates were prepared by adding 17 µl of cold matrigel. The plate was incubated for 2 min at 37° C. before tumor pieces were added (triplicates). 33 µl of cold matrigel was added per well and the plate was incubated again for 2 min at 37° C. 100 µl (50 nM or 5 nM) of TCB antibody dilution (diluted in Jurkat medium without Hygromycine but with 2× Penicillin/Streptomycine) was added per well. Jurkat-NFAT reporter cells were harvested and viability was assessed using ViCell. Cells were centrifuged at 350×g for 7 min before they were resuspended in Jurkat medium without Hygromycine. 50 µl of the cell suspension was added per well (50,000 cells/well). The plate was incubated for 4 to 5 h at 37° C. in a humidified incubator before it was taken out for luminescence read out. 50 µl of ONE-Glo solution was added to each well and incubated for 10 min at room temperature in the dark. Luminescence was detected using WALLAC Victor3 ELISA reader (PerkinElmer2030), with a 5 sec/well detection time.

7.8.3. Results

Results from tumor samples from three patients are shown in FIGS. 9-11. The results shown in FIG. 9 are from tumor samples obtained from a patient having a malignant neoplasm of bronchus and lung: middle lobe, bronchus or lung, squamous cell carcinoma. The results shown in FIG. 10 are from tumor samples obtained from a patient having a malignant neoplasm of bronchus and lung: lower lobe, bronchus or lung, non-keratinizing squamous cell carcinoma. The results shown in FIG. 11 are from tumor samples obtained from a patient having a malignant neoplasm of bronchus and lung: upper lobe, bronchus or lung, adenocarcinoma with acinar type. Each bar in FIGS. 9-11 represents the mean of triplicates. Standard error is indicated by error bars. The dotted line indicates luminescence for Jurkat NFAT cells incubated with tumor samples without any TCB. Two-tailed, unpaired t-test was used for statistical analysis. P-values below 0.05 were considered as significant and were indicated with stars (*$P \leq 0.05$; $P \leq 0.001$; *$P \leq 0.001$). In each of FIGS. 9-11, tumor samples incubated with GO2 TCB displayed significantly more luminescence than samples incubated with DP47 negative control TCB.

7.9 Example 9: In Vitro Characterization of GO2 TCB

7.9.1. Overview

GO2 TCB (Example 7) recognizing the tumor-specific aberrantly glycosylated MUC1 was functionally characterized on tumor cells expressing MUC1.

7.9.2. Materials and Methods

7.9.2.1 Cell Lines and PBMCs

T3M4 pfzv and MCF7 cs engineered tumor cell lines were cultured in DMEM with 10% FCS and 2 mM Glutamine. MCF10A is a human non-tumorigenic mammary epithelial cell line (ATCC® CRL-10317). HBEpiC are human bronchial epithelial cells (Sciencell #3210). PBMCs were isolated by gradient centrifugation using whole blood from healthy volunteers.

7.9.2.2 Target Binding by Flow Cytometry

Target cells as indicated were harvested with Cell Dissociation Buffer, washed with PBS and resuspended in FACS buffer. The antibody staining was performed in a 96-well round bottom plate. 200,000 cells were seeded per well. The plate was centrifuged for 4 min at 400 g and the supernatant was removed. The test antibodies were diluted in FACS buffer and 30 µl of the antibody solution was added to the cells for 30 min at 4° C. To remove unbound antibody the cells were washed twice with FACS buffer before addition of the diluted secondary antibody (PE-conjugated AffiniPure F(ab')2 Fragment goat anti-human IgG Fcγ Fragment Specific, Jackson ImmunoResearch #109-116-170). After 30 min incubation at 4° C. unbound secondary antibody was washed away. Before measurement the cells were resuspended in 200 µl FACS buffer and analyzed by flow cytometry using BD Fortessa. Assays were performed in triplicates.

7.9.2.3 T Cell Mediated Tumor Cell Killing and T Cell Activation

Target cells were harvested with Trypsin/EDTA, counted and viability was checked. The cells were resuspended in their respective medium with a final concentration of 300,000 cells per ml. Then 100 µl of the target cell suspension was transferred into each well of a 96-flat bottom plate. The plate was incubated overnight at 37° C. in the incubator to allow adherence of the cells to the plate. On the next day PBMCs were isolated from whole blood. The blood was diluted 2:1 with PBS and overlayed on 15 ml Histopaque-1077 (#10771, Sigma-Aldrich) in Leucosep tubes and centrifuged for 30 min at 450 g without brake. After centrifugation, the band containing the cells was collected with a 10 ml pipette and transferred into 50 ml tubes. The tubes were filled up with PBS until 50 ml and centrifuged (400 g, 10 min, room temperature). The supernatant was removed and the pellet resuspended in PBS. After centrifugation (300 g, 10 min, room temperature), supernatants were discarded, 2 tubes were pooled and the washing step was repeated (this time centrifugation 350 g, 10 min, room temperature). Afterwards, the cells were resuspended and the pellets pooled in 50 ml PBS for cell counting. After counting cells were centrifuged (350 g, 10 min, room temperature) and resuspended at 6 million cells per ml in RPMI with 2% FCS and 2 nM Glutamine. Medium was removed from plated target cells and the test antibodies diluted in RPMI with 2% FCS and 2 nM Glutamine were added. 300,000 cells of the effector cell solution were transferred to each well resulting in a E:T ratio of 10:1. To determine the maximal release target cells were lysed with Triton X-100. LDH release was determined after 24 h and 48 h using Cytotoxicity Detection Kit (1644793, Roche Applied Science). Activation marker upregulation on T cells after tumor cell killing was measured by flow cytometry. Briefly, PBMCs were harvested, transferred into a 96-well round bottom plate and stained with CD4 APC (300514, BioLegend), CD8 FITC (344704, BioLegend), CD25 BV421 (302630, BioLegend), CD69 PE (310906, BioLegend) antibodies diluted in FACS buffer. After 30 min incubation at 4° C. the cells were washed twice with FACS buffer. Before measuring the fluorescence using BD Fortessa II the cells were resuspended in 200 µl FACS buffer. Assays were performed in triplicates.

7.9.2.4 Cytokine/Chemokine Release by Cytometric Bead Array

Cytokine/chemokine secretion in the supernatant was measured by flow cytometry, using the cytometric bead array (CBA), according to the manufacturer's guidelines. Supernatants from T cell mediated killing assays were collected and stored at −20° C. Supernatants were subsequently thawed and tested according to manufacturer's instructions. The following CBA kits (BD Biosciences) were used: CBA human interferon gamma (IFNγ) Flex Set (E7), CBA human Granzyme B Flex Set (D7), CBA human IL6 Flex Set (A7), CBA human IL8 Flex Set (A9), CBA human IL10 Flex Set (B7) and CBA human tumor necrosis factor (TNF) Flex Set (D9). Samples were measured using the BD FACS Canto II and analyses were performed using the Diva Software (BD Biosciences). Assays were performed in triplicates.

7.9.3. Results

Binding of GO2 TCB to the breast cancer cell line MCF7 and the pancreatic cancer cell line T3M4, both engineered to express the aberrantly glycosylated MUC1, was confirmed (FIG. 12). Subsequently, activity of GO2 TCB was tested on both tumor cell lines, MCF7 and T3M4, using freshly insolated PBMCs (FIG. 13 and FIG. 14). Tumor cell killing of both cell lines was detected after 24 h and even stronger after 48 h. This was accompanied by strong activation of CD4 T cells and CD8 T cells determined by upregulation of the two activation markers CD25 and CD69 and the release of IL6, IL8, IL10, IFNγ, TNFα and Granzyme B into the supernatant. As negative control the respective untargeted TCB was included.

To prove that GO2 TCB does not bind to normally glycosylated MUC1 on epithelial cells, binding to MCF10A, which is a human non-tumorigenic mammary epithelial cell line, and to HBEpiC, which are primary human bronchial epithelial cells, was tested. As a positive control the HMFG1 TCB, which does not discriminate between MUC1 expressed on normal and on tumor cells, was included. HFMG1 TCB was found to bind to both tested cells, confirming the expression of MUC1, but GO2 TCB was not able to bind to these cells (FIG. 15). In addition, GO2 TCB was tested to see if it would induce killing or T cell activation in the presence of normal epithelial cells expressing MUC1. This was tested on MCF10A cells and there was no killing or T cell activation detectable with GO2 TCB, whereas HMFG1 TCB induced killing as well as T cell activation (FIG. 16).

7.10 Example 10: Functional Characterization of GO2 and GO2 TCB Antibodies by Surface Plasmon Resonance 7.10.1. Overview GO2 and GO2 TCB (Example 7) were characterized by surface plasmon resonance.

7.10.2. Materials and Methods 7.10.2.1 Binding of GO2 and GO2 TCB to Immobilized Glycopeptides Binding of the GO2 antibody and GO2 TCB to human and cynomolgus glycopeptides (Table 6) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

TABLE 6

| Glycopeptide | Sequence | Concentration in PBS |
|---|---|---|
| Human peptide | PDTSAAPGSTAPPAHVVTSAP (SEQ ID NO: 48) | 0.9 mg/ml |
| Cynomolgus peptide | PDTSAAPGSTGPPAHVVTSAP (SEQ ID NO: 49) | 1.8 mg/ml |

The biotinylated glycopeptides were dissolved in PBS and the final concentration was between 0.9 and 1.8 mg/ml (Table 6). Biotinylated glycopeptides were directly coupled to a flow cell of a streptavidin (SA) sensor chip. Immobilization levels up to 880 resonance units (RU) were used. The GO2 antibody or the GO2 TCB were injected with a flow of 30 μL/minute through the flow cells, over 240 seconds and at a concentration of 1000 nM (FIG. 17). The dissociation was monitored for 500 sec. Bulk refractive index differences were corrected for by subtracting the response obtained in a reference flow cell, where no protein was immobilized.

7.10.2.2 Avidity of GO2 and GO2 TCB to Immobilized Glycopeptides

The avidity of GO2 and GO2 TCB was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Biotinylated glycopeptides (Table 6) were directly coupled to a flow cell of a streptavidin (SA) sensor chip. Immobilization levels up to 200 resonance units (RU) were used.

The GO2 antibody or the GO2 TCB were injected with a flow of 30 μL/minute through the flow cells over 120 seconds and at a concentration range from 3.9 to 1000 nM (1:2 dilution). The dissociation was monitored for 400 sec. Bulk refractive index differences were corrected for by subtracting the response obtained in a reference flow cell, where no protein was immobilized. The KDs were derived, despite the bivalency of the interaction, by fitting the curve to a 1:1 Langmuir binding using the Biaeval software (GE Healthcare). The "apparent" KD can therefore be used for comparison purposes only.

7.10.3. Results

As can be seen in the sensorgrams of FIG. 18, GO2 antibody (FIG. 18A) and GO2 TCB (FIG. 18B) bind both human and cynomolgous glycopeptides. GO2 antibody and GO2 TCB bind with higher avidity to cynomolgus than to human glycopeptide.

Figure 19A:
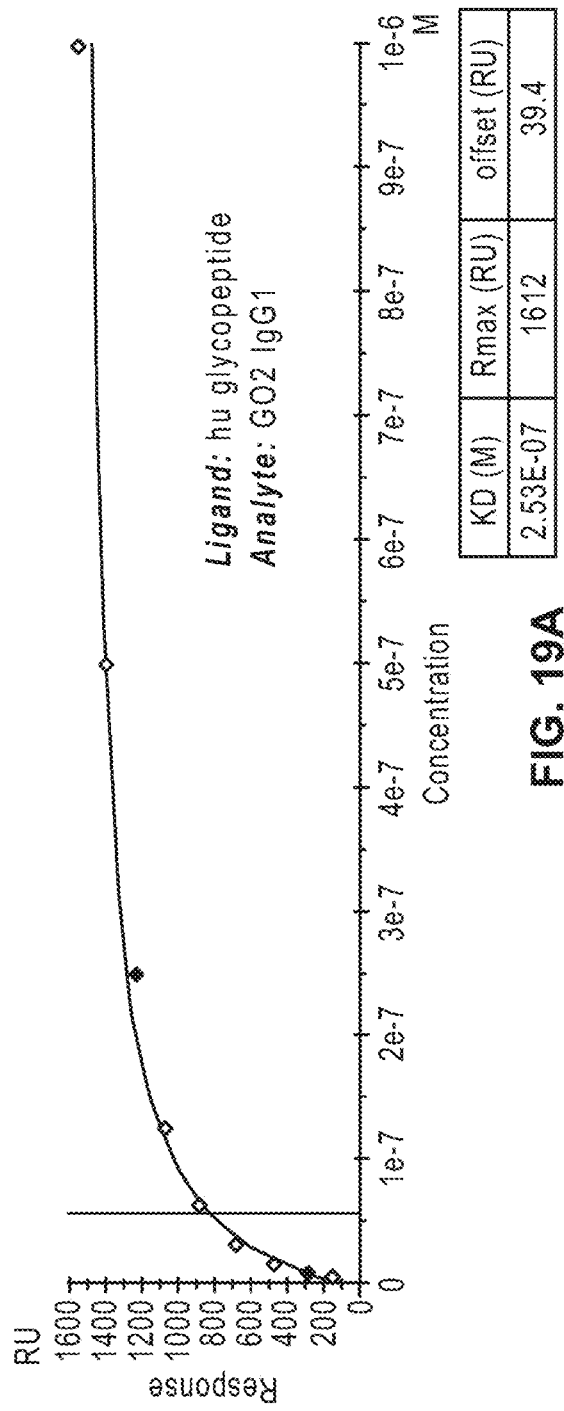
Figure 19B:
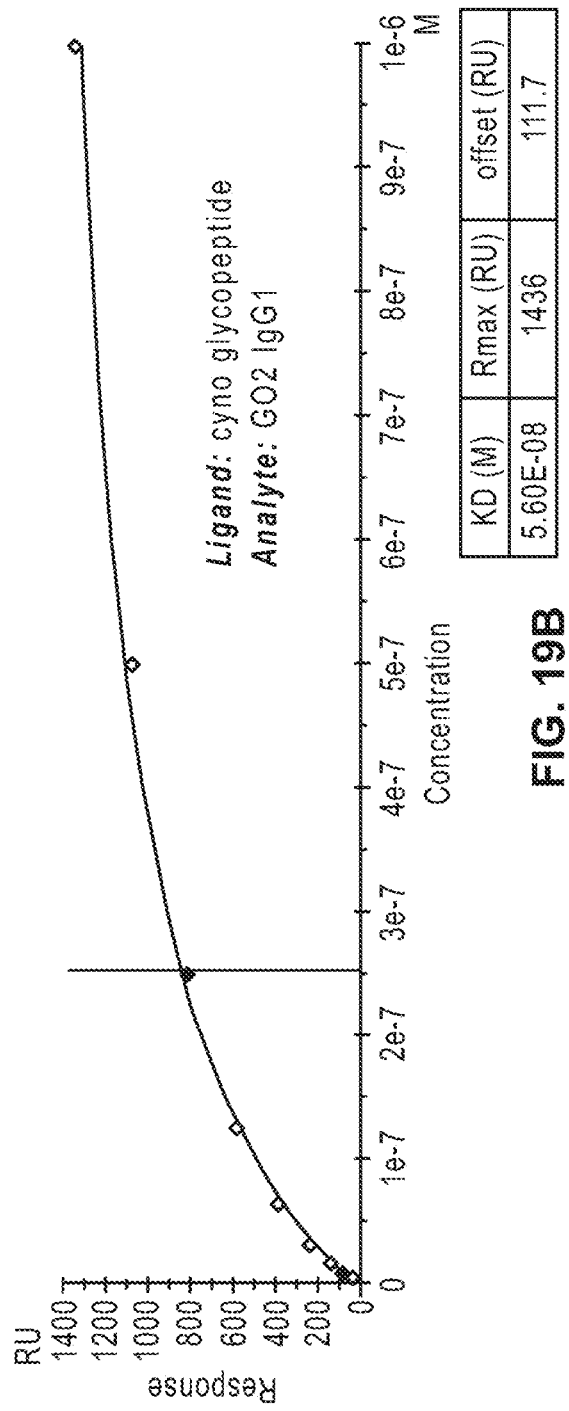
Figure 19C:
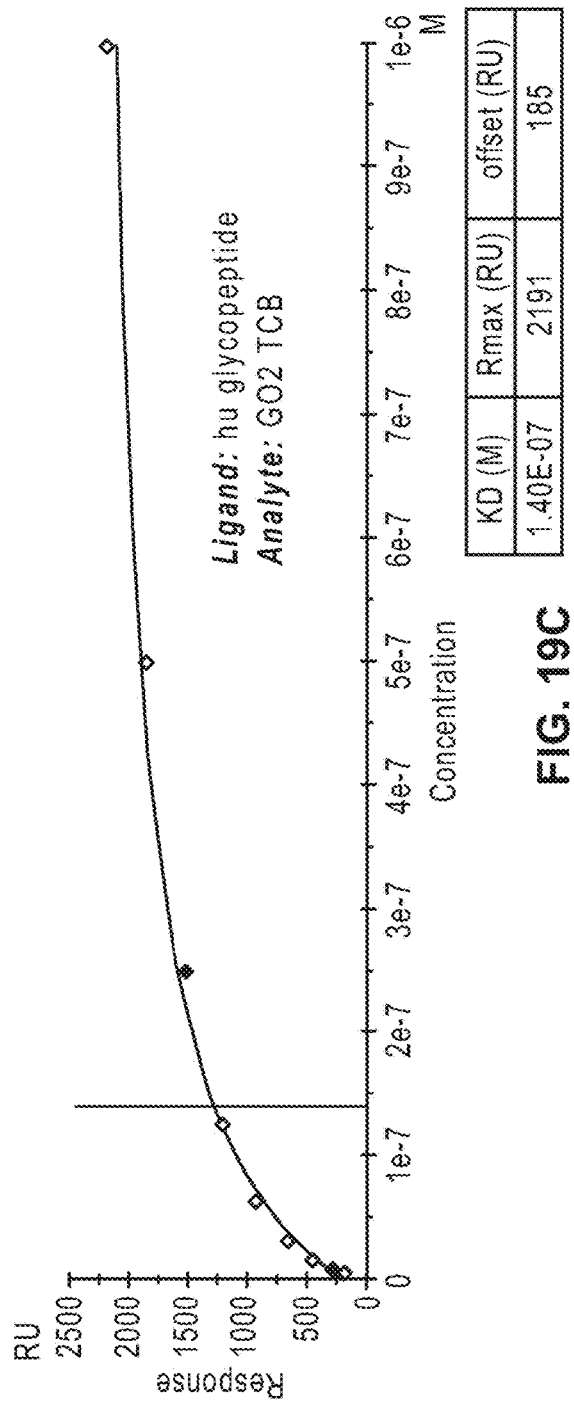
Figure 19D:
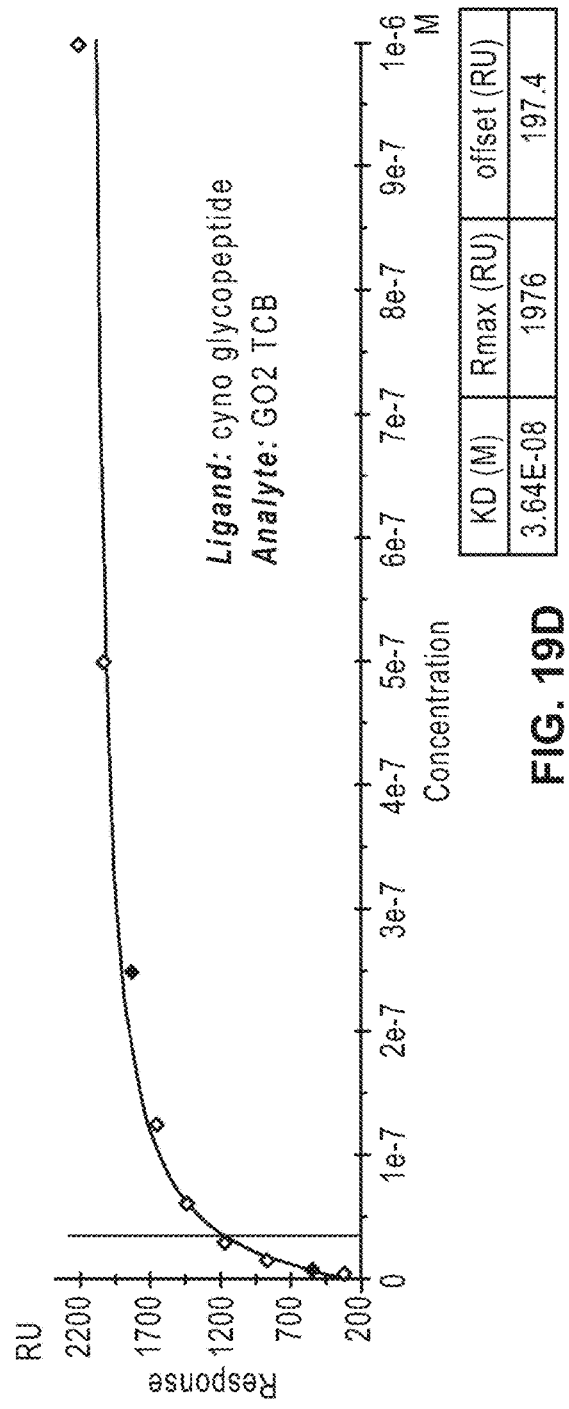

As can be seen in FIG. 19, binding of a bivalent GO2 binder (IgG, TCB) to human glycopeptide is in the three-digit nanomolar (FIGS. 19A and 19C), whereas binding to cynomolgus glycopeptide is in the two-digit nanomolar (FIGS. 19B and 19D).

7.11 Example 11: Exploratory Single Dose Pharmacokinetic and Tolerability Study of GO2 TCB in Cynomolgus Monkeys 7.11.1. Overview The objectives of this study are to determine the pharmacokinetics and tolerability of the GO2 TCB described in Example 7, when given by a single intravenous injection to cynomolgus monkeys.

7.11.2. Materials and Methods 7.11.2.1 Preparation of GO2 TCB

Thawing of the frozen stock solution of GO2 TCB (2.12 mg/mL) and formulation buffer (20 mM Histidine, 140 mM NaCl, 0.01% Tween 20; pH 6.0) is done overnight in a fridge set to maintain 4° C. Test item dosing formulations are prepared under sterile conditions at appropriate concentrations to meet dose level requirements by dilution with formulation buffer.

The dosing formulation is prepared within 2 hours before injection and stored at room temperature until use. Polypropylene containers are used for preparation and storage of dosing formulation to prevent adsorption. Dosing formulations should are not filtered, nor stirred or shaken. Any mixing is done either by gentle pipetting or gentle swinging of the container.

7.11.2.2 Animals

Cynomolgus monkeys (*Macaca fascicularis*) 2-4 years of age and weighing less than 4 kg are used in the study. The animals are allowed to acclimate to the test facility primate toxicology accommodation for at least 6 weeks before the commencement of dosing.

During the week before the commencement of dosing, the animals are approved for entry into the experiment on the basis of a satisfactory veterinary examination (performed shortly after arrival), clinical observation records, body weight profile and clinical pathology investigations.

Animals selected for the study are randomly allocated to cages based on supplied group compatibility information and then allotted individual study numbers. The animals are allocated a cage in groups of up to 5.

7.11.2.3 Husbandry

Animals are socially housed where possible, in groups of up to 5 by sex in two story gang pens measuring 1.61×1.66× 2.5 m on the lower story and 1.61×1.66×2.03 m on the upper. Bedding material is wood shavings. There are no known contaminants in the bedding that would interfere with the objectives of the study.

The targeted conditions for animal room environment are be as follows:

Temperature: 18-24° C.
Humidity: 40-70%
Ventilation: a minimum of 10 air changes per hour
Light Cycle: 12 hours light and 12 hours dark (except when interrupted by study procedures/activities).

There is automatic control of temperature and humidity which is continuously monitored and recorded. There is automatic control of light cycle.

Special Diets Services (SDS) MP(E) Short SQC Diet is provided as a daily ration throughout the study. Approximately 200 gram ration of feed per animal is provided once daily. There are no known contaminants in the feed that would interfere with the objectives of the study. The animals have access to water ad libitum from the public supply. There are no known contaminants in the water that would interfere with the objectives of the study.

The animal's home environment is enriched to promote social interaction, play and exploration. The animals have perches and materials such as plastic toys, balls, climbing frames and stainless steel mirrors. These are exchanged frequently to reduce familiarity. Prior to exchange, all toys and climbing frames are thoroughly cleaned to avoid cross-contamination. The animals are also offered a range of other treats such as forage mix, vegetables, nuts, biscuits and fruits normally on a daily basis.

Veterinary care is available throughout the course of the study and animals are examined by the veterinary staff as warranted by clinical signs or other changes.

7.11.2.4 Experimental Design

One male and one female animal are administered GO2 TCB

TABLE 7

| Group No. | Dose Level (µg/kg) | Dose Volume (mL/kg) | Dose Concentration (µg/kg) |
|---|---|---|---|
| 1 (1 male and 1 female) | 100 | 1 | 100 |
| 2 (1 male and 1 female) | 300 | 1 | 300 |

GO2 TCB is administered to the appropriate animals by a single intravenous slow bolus injection (1-2 min) in the saphenous vein or tail vein at least 8 days apart. is staggered so that only one male and one female receive a new dose level on any single day. Based on the observations from the previous dose level (including clinical pathology data), the doses are increased or decreased for the next dose group. Naïve animals are used for each dose level. The doses are given using a syringe with attached Vygon infusion needle.

Animals are necropsied ca 72 hours after dosing (after the last scheduled sample has been taken). For all animals which have to be terminated prior to the scheduled date due to severe clinical symptoms, complete panel of clinical pathology (additional sampling prior to termination, if feasible) and histopathology are analyzed.

The intravenous injection route of administration has been selected for this study as this route is a possible route of clinical application. The low dose and the high dose levels were chosen to cover a clinically relevant dose range and to minimize the potential harm to the animals. The low dose was selected based on the experience in the cynomolgus monkey with similar T-cell bispecific antibodies of similar potency and the high-dose represents a 3-fold increment thereof.

7.11.3. Results

GO2 TCB is tolerated at the tested doses.

8. SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

1. An anti-glyco-MUC1 antibody or antigen binding fragment that:
    a. preferentially binds to a glyco-MUC1 epitope that is overexpressed on cancer cells as compared to normal cells; and
    b. competes with an antibody or antigen binding fragment comprising a heavy chain variable (VH) sequence of SEQ ID NO:3 and a light chain variable (VL) sequence of SEQ ID NO:4 for binding to the breast cancer cell line MCF7 or T47D.
2. An anti-Glyco-MUC1 antibody or antigen binding fragment that
    a. binds to the MUC1 tandem repeat (VTSAPDTR-PAPGSTAPPAHG)$_3$ (SEQ ID NO:47) that has been glycosylated in vitro using purified recombinant human glycosyltransferases GalNAc-T1, GalNAc-T2, and GalNAc-T4, and (referred to hereinafter as the "first epitope"); and
    b. competes with an antibody or antigen binding fragment comprising a heavy chain variable (VH) sequence of SEQ ID NO:3 and a light chain variable (VL) sequence of SEQ ID NO:4 for binding to the breast cancer cell line MCF7 or T47D.
3. The anti-glyco-MUC1 antibody or antigen-binding fragment of embodiment 1 or embodiment 2 comprising a complementarity determining region (CDR) H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31.
4. The anti-glyco-MUC1 antibody or antigen-binding fragment of embodiment 3, wherein CDR-H1 comprises the amino acid sequence of SEQ ID NO:5.
5. The anti-glyco-MUC1 antibody or antigen-binding fragment of embodiment 3, wherein CDR-H1 comprises the amino acid sequence of SEQ ID NO:23.
6. The anti-glyco-MUC1 antibody or antigen-binding fragment of embodiment 3, wherein CDR-H1 comprises the amino acid sequence of SEQ ID NO:28.
7. The anti-glyco-MUC1 antibody or antigen-binding fragment of embodiment 3, wherein CDR-H1 comprises the amino acid sequence of SEQ ID NO:32.
8. The anti-glyco-MUC1 antibody or antigen-binding fragment of any one of embodiments 3 to 7, wherein CDR-H2 comprises the amino acid sequence of SEQ ID NO:6.
9. The anti-glyco-MUC1 antibody or antigen-binding fragment of any one of embodiments 3 to 7, wherein CDR-H2 comprises the amino acid sequence of SEQ ID NO:24.
10. The anti-glyco-MUC1 antibody or antigen-binding fragment of any one of embodiments 3 to 9, wherein CDR-H3 comprises the amino acid sequence of SEQ ID NO:7.
11. The anti-glyco-MUC1 antibody or antigen-binding fragment of any one of embodiments 3 to 10, wherein CDR-L1 comprises the amino acid sequence of SEQ ID NO:30.

12. The anti-glyco-MUC1 antibody or antigen-binding fragment of any one of embodiments 3 to 10, wherein CDR-L1 comprises the amino acid sequence of SEQ ID NO:26.

13. The anti-glyco-MUC1 antibody or antigen-binding fragment of any one of embodiments 3 to 12, wherein CDR-L2 comprises the amino acid sequence of SEQ ID NO:27.

14. The anti-glyco-MUC1 antibody or antigen-binding fragment of any one of embodiments 3 to 13, wherein CDR-L3 comprises the amino acid sequence of SEQ ID NO:10.

15. The anti-glyco-MUC1 antibody or antigen-binding fragment of embodiment 1 or embodiment 2 in which the VH comprises complementarity determining regions (CDRs) of SEQ ID NOS:5-7 and the VL comprises CDRs of SEQ ID NOS:8-10.

16. The anti-glyco-MUC1 antibody or antigen-binding fragment of embodiment 1 or embodiment 2 in which the VH comprises complementarity determining regions (CDRs) of SEQ ID NOS:23-25 and the VL comprises CDRs of SEQ ID NOS:26, 27, and 10.

17. The anti-glyco-MUC1 antibody or antigen-binding fragment of embodiment 1 or embodiment 2 in which the VH comprises complementarity determining regions (CDRs) of SEQ ID NOS:28, 29, and 25 and the VL comprises CDRs of SEQ ID NOS:30, 9, and 31.

18. The anti-glyco-MUC1 antibody or antigen-binding fragment of any one of embodiments 1 to 17 which is a chimeric or humanized antibody.

19. The anti-glyco-MUC1 antibody or antigen-binding fragment of any one of embodiments 1 to 18 in which the VH comprises an amino acid sequence having at least 95% sequence identity to SEQ ID NO:3 and the VL comprises an amino acid sequence having at least 95% sequence identity to SEQ ID NO:4.

20. The anti-glyco-MUC1 antibody or antigen-binding fragment of any one of embodiments 1 to 18 in which the VH comprises an amino acid sequence having at least 97% sequence identity to SEQ ID NO:3 and the VL comprises an amino acid sequence having at least 97% sequence identity to SEQ ID NO:4.

21. The anti-glyco-MUC1 antibody or antigen-binding fragment of any one of embodiments 1 to 18 in which the VH comprises an amino acid sequence having at least 99% sequence identity to SEQ ID NO:3 and the VL comprises an amino acid sequence having at least 99% sequence identity to SEQ ID NO:4.

22. The anti-glyco-MUC1 antibody or antigen-binding fragment of embodiment 1 or embodiment 2 in which the VH comprises the amino acid sequence of SEQ ID NO:3 and the VL comprises the amino acid sequence of SEQ ID NO:4.

23. The anti-glyco-MUC1 antibody or antigen-binding fragment of any of embodiments 1 to 22 which is multivalent.

24. The anti-glyco-MUC1 antibody or antigen-binding fragment of any of embodiments 1 to 22 which is in the form of a single-chain variable fragment (scFv).

25. The anti-glyco-MUC1 antibody or antigen-binding fragment of embodiment 24 wherein the scFv comprises the heavy chain variable fragment N-terminal to the light chain variable fragment.

26. The anti-glyco-MUC1 antibody or antigen-binding fragment of embodiment 24 wherein the scFv heavy chain variable fragment and light chain variable fragment are covalently bound to a linker sequence of 4-15 amino acids.

27. The anti-glyco-MUC1 antibody or antigen-binding fragment of any of embodiments 1 to 22 which is in the form of a multispecific antibody.

28. The anti-glyco-MUC1 antibody or antigen-binding fragment of embodiment 27 wherein the multispecific antibody is a bispecific antibody that binds to a second epitope that is different from the first epitope.

29. The anti-glyco-MUC1 antibody or antigen-binding fragment of embodiment 28, wherein the bispecific antibody is a CrossMab, a Fab-arm exchange antibody, a bispecific T-cell engager (BITE), or a dual-affinity retargeting molecule (DART).

30. The anti-glyco-MUC1 antibody or antigen-binding fragment of embodiment 29, wherein the bispecific antibody is a CrossMab.

31. The anti-glyco-MUC1 antibody or antigen-binding fragment of embodiment 30, wherein the bispecific antibody is a CrossMabFAB.

32. The anti-glyco-MUC1 antibody or antigen-binding fragment of embodiment 30, wherein the bispecific antibody is a CrossMab$^{VH-VL}$.

33. The anti-glyco-MUC1 antibody or antigen-binding fragment of embodiment 30, wherein the bispecific antibody is a CrossMab$^{CH1-CL}$.

34. The anti-glyco-MUC1 antibody or antigen-binding fragment of embodiment 29, wherein the bispecific antibody is a Fab-arm exchange antibody.

35. The anti-glyco-MUC1 antibody or antigen-binding fragment of embodiment 29, wherein the bispecific antibody is a dual-affinity retargeting molecule (DART).

36. The anti-glyco-MUC1 antibody or antigen-binding fragment of embodiment 29, wherein the bispecific antibody is a bispecific T-cell engager (BITE).

37. The anti-glyco-MUC1 antibody or antigen-binding fragment of any one of embodiments 28 to 35, wherein the second epitope is a MUC1 epitope.

38. The anti-glyco-MUC1 antibody of antigen-binding fragment of any one of embodiments 28 to 35, wherein the second epitope is a MUC1 epitope that is overexpressed on cancer cells as compared to normal cells.

39. The anti-glyco-MUC1 antibody or antigen-binding fragment of any one of embodiments 28 to 36, wherein the second epitope is a T-cell epitope.

40. The anti-glyco-MUC1 antibody or antigen-binding fragment of embodiment 39, wherein the T-cell epitope comprises a CD3 epitope, a CD8 epitope, a CD 16 epitope, a CD25 epitope, a CD28 epitope, or an NKG2D epitope.

41. The anti-glyco-MUC1 antibody or antigen-binding fragment of embodiment 40, wherein the T-cell epitope comprises a CD3 epitope, which is optionally an epitope present in human CD3.

42. The anti-glyco-MUC1 antibody or antigen-binding fragment of embodiment 41, wherein the CD3 epitope comprises a CD3 gamma epitope, a CD3 delta epitope, a CD3 epsilon epitope, or a CD3 zeta epitope.

43. The anti-glyco-MUC1 antibody or antigen-binding fragment of any one of embodiments 1 to 42 which is conjugated to a detectable moiety.

44. The anti-glyco-MUC1 antibody or antigen binding fragment of embodiment 43 in which the detectable marker is an enzyme, a radioisotope, or a fluorescent label.

45. A bispecific antibody comprising a first antigen binding domain that binds to CD3 (optionally human CD3) and a second antigen binding domain that binds to glyco-MUC1, wherein the bispecific antibody competes with an antibody or antigen binding fragment comprising a heavy chain variable (VH) sequence of SEQ ID NO:3 and a light chain variable (VL) sequence of SEQ ID NO:4 for binding to the breast cancer cell line MCF7 or T47D, and wherein the first antigen binding domain comprises a heavy chain variable region comprising the heavy chain CDR-H1 of SEQ ID NO:34, the CDR-H2 of SEQ ID NO:35, and the CDR-H3 of SEQ ID NO:36; and a light chain variable region comprising the light chain CDR-L1 of SEQ ID NO:37, the CDR-L2 of SEQ ID NO:38 and the CDR-L3 of SEQ ID NO:39.

46. The bispecific antibody of embodiment 45, wherein the second antigen binding domain comprises (i) a heavy chain variable region comprising the CDR-H1 of SEQ ID NO: 5, the CDR-H2 of SEQ ID NO: 6, and the CDR-H3 of SEQ ID NO: 7; and a light chain variable region comprising the light chain CDR-L1 of SEQ ID NO: 8, the CDR-L2 of SEQ ID NO: 9 and the CDR-L3 of SEQ ID NO:10.

47. The bispecific antibody of embodiment 45 or embodiment 46, wherein the first antigen binding domain comprises a heavy chain variable region sequence that is at least about 95%, 96%, 97%, 98%, 99% or 100% identical to the amino acid sequence of SEQ ID NO:40 and a light chain variable region sequence that is at least about 95%, 96%, 97%, 98%, 99% or 100% identical to the amino acid sequence of SEQ ID NO:41.

48. The bispecific antibody of embodiment 47, the first antigen binding domain comprises the heavy chain variable region sequence of SEQ ID NO:40 and the light chain variable region sequence of SEQ ID NO:41.

49. The bispecific antibody of any one of embodiments 45 to 48, wherein the second antigen binding domain comprises a heavy chain variable region sequence that is at least about 95%, 96%, 97%, 98%, 99% or 100% identical to the amino acid sequence of SEQ ID NO:3 and a light chain variable region sequence that is at least about 95%, 96%, 97%, 98%, 99% or 100% identical to the amino acid sequence of SEQ ID NO:4.

50. The bispecific antibody of embodiment 49, wherein the second antigen binding domain comprises the heavy chain variable region sequence of SEQ ID NO:3 and the light chain variable region sequence of SEQ ID NO:4.

51. The bispecific antibody of any one of embodiments 45 to 50, wherein the first and/or the second antigen binding domain is a Fab molecule.

52. The bispecific antibody of embodiment 51, wherein the first antigen binding domain is a crossover Fab molecule, wherein either the variable or the constant regions of the Fab light chain and the Fab heavy chain are exchanged.

53. The bispecific antibody of embodiment 52, wherein the first and the second antigen binding domain of the bispecific antibody are both Fab molecules, and in one of the antigen binding domains (particularly the first antigen binding domain) the variable domains VL and VH of the Fab light chain and the Fab heavy chain are replaced by each other, wherein
   a. in the constant domain CL of the first antigen binding domain the amino acid at position 124 is substituted by a positively charged amino acid (numbering according to Kabat), and wherein in the constant domain CH1 of the first antigen binding domain the amino acid at position 147 or the amino acid at position 213 is substituted by a negatively charged amino acid (numbering according to Kabat EU index); or
   b. in the constant domain CL of the second antigen binding domain the amino acid at position 124 is substituted by a positively charged amino acid (numbering according to Kabat), and wherein in the constant domain CH1 of the second antigen binding domain the amino acid at position 147 or the amino acid at position 213 is substituted by a negatively charged amino acid (numbering according to Kabat EU index),
   wherein the constant domains CL and CH1 of the antigen binding domain having the VH/VL exchange are not replaced by each other.

54. The bispecific antibody of embodiment 53, wherein
   a. in the constant domain CL of the first antigen binding domain the amino acid at position 124 is substituted independently by lysine (K), arginine (R) or histidine (H) (numbering according to Kabat), and in the constant domain CH1 of the first antigen binding domain the amino acid at position 147 or the amino acid at position 213 is substituted independently by glutamic acid (E), or aspartic acid (D) (numbering according to Kabat EU index); or
   b. in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index).

55. The bispecific antibody of embodiment 54, wherein in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 or the amino acid at position 213 is substituted independently by glutamic acid (E), or aspartic acid (D) (numbering according to Kabat EU index).

56. The bispecific antibody of embodiment 55, wherein in the constant domain CL of the second antigen binding domain the amino acid at position 124 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index).

57. The bispecific antibody of embodiment 55, in the constant domain CL of the second antigen binding domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding domain the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).
58. The bispecific antibody of embodiment 57, wherein in the constant domain CL of the second antigen binding domain the amino acid at position 124 is substituted by lysine (K) (numbering according to Kabat) and the amino acid at position 123 is substituted by lysine (K) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).
59. The bispecific antibody of embodiment 57, wherein in the constant domain CL of the second antigen binding domain the amino acid at position 124 is substituted by lysine (K) (numbering according to Kabat) and the amino acid at position 123 is substituted by arginine (R) (numbering according to Kabat), and in the constant domain CH1 of the second antigen binding domain the amino acid at position 147 is substituted by glutamic acid (E) (numbering according to Kabat EU index) and the amino acid at position 213 is substituted by glutamic acid (E) (numbering according to Kabat EU index).
60. The bispecific antibody of any one of embodiments 53 to 59, wherein the constant domain CL of the second antigen binding domain is of kappa isotype.
61. The bispecific antibody of any one of embodiments 45 to 60, wherein the first and the second antigen binding domain are fused to each other, optionally via a peptide linker.
62. The bispecific antibody of embodiment 61, wherein the first and the second antigen binding domain are each a Fab molecule and either (i) the second antigen binding domain is fused at the C-terminus of the Fab heavy chain to the N-terminus of the Fab heavy chain of the first antigen binding domain, or (ii) the first antigen binding domain is fused at the C-terminus of the Fab heavy chain to the N-terminus of the Fab heavy chain of the second antigen binding domain.
63. The bispecific antibody of any one of embodiments 45 to 62, wherein the bispecific antibody provides monovalent binding to CD3.
64. The bispecific antibody of embodiment 63, which comprises two antigen binding domains that specifically bind to glyco-MUC1.
65. The bispecific antibody of embodiment 64, wherein the two antigen binding domains that specifically bind to glyco-MUC1 comprise the same amino acid sequences.
66. The bispecific antibody of any one of embodiments 45 to 65, wherein the bispecific antibody further comprises an Fc domain composed of a first and a second subunit.
67. The bispecific antibody of embodiment 66, wherein the Fc domain is an IgG Fc domain.
68. The bispecific antibody of embodiment 67, wherein the Fc domain is an IgG$_1$ Fc domain.
69. The bispecific antibody of embodiment 67, wherein the Fc domain is an IgG$_4$ Fc domain.
70. The bispecific antibody of embodiment 69, wherein the IgG4 Fc domain comprises an amino acid substitution at position S228 (Kabat EU index numbering), preferably the amino acid substitution S228P.
71. The bispecific antibody of embodiment 66, wherein the Fc domain is a human Fc domain.
72. The bispecific antibody of embodiment 71, wherein the Fc domain is a human IgG$_1$ Fc domain, which optionally comprises SEQ ID NO:42.
73. The bispecific antibody of any one of embodiments 66 to 72, wherein the first, the second and, where present, the third antigen binding domain are each a Fab molecule, and (a) either (i) the second antigen binding domain is fused at the C-terminus of the Fab heavy chain to the N-terminus of the Fab heavy chain of the first antigen binding domain and the first antigen binding domain is fused at the C-terminus of the Fab heavy chain to the N-terminus of the first subunit of the Fc domain, or (ii) the first antigen binding domain is fused at the C-terminus of the Fab heavy chain to the N-terminus of the Fab heavy chain of the second antigen binding domain and the second antigen binding domain is fused at the C-terminus of the Fab heavy chain to the N-terminus of the first subunit of the Fc domain; and (b) the third antigen binding domain, where present, is fused at the C-terminus of the Fab heavy chain to the N-terminus of the second subunit of the Fc domain.
74. The bispecific antibody of any one of embodiments 66 to 73, wherein the Fc domain comprises a modification promoting the association of the first and the second subunit of the Fc domain.
75. The bispecific antibody of any one of embodiments 66 to 74, wherein the Fc domain comprises one or more amino acid substitutions that reduces binding to an Fc receptor and/or effector function.
76. The bispecific antibody of embodiment 45, comprising
   a. a first antigen binding domain that specifically binds to CD3, wherein the first antigen binding domain is a crossover Fab molecule wherein either the variable or the constant regions, preferably the variable regions, of the Fab light chain and the Fab heavy chain are exchanged;
   b. a second and a third antigen binding domain that specifically bind to glyco-MUC1, comprising a heavy chain variable region comprising the heavy chain CDR-H1 of SEQ ID NO: 5, the CDR-H2 of SEQ ID NO: 6, and the CDR-H3 of SEQ ID NO: 7; and a light chain variable region comprising the light chain CDR-L1 of SEQ ID NO: 8, the CDR-L2 of SEQ ID NO: 9 and the CDR-L3 of SEQ ID NO:10, wherein the second and third antigen binding domain are each a Fab molecule;
   c. an Fc domain composed of a first and a second subunit capable of stable association,
   wherein the second antigen binding domain is fused at the C-terminus of the Fab heavy chain to the N-terminus of the Fab heavy chain of the first antigen binding domain, and the first antigen binding domain is fused at the C-terminus of the Fab heavy chain to the N-terminus of the first subunit of the Fc domain, and wherein the third antigen binding domain is fused at the C-terminus of the Fab heavy chain to the N-terminus of the second subunit of the Fc domain.
77. The bispecific antibody of embodiment 77, wherein the first antigen binding domain comprises a heavy chain variable region comprising the heavy chain CDR-H1 of SEQ ID NO:34, the CDR-H2 of SEQ ID NO:35, and the CDR-H3 of SEQ ID NO:36; and a light chain variable region comprising the light chain CDR-L1 of SEQ ID NO:37, the CDR-L2 of SEQ ID NO:38 and the CDR-L3 of SEQ ID NO:39.

78. The bispecific antibody of embodiment 77, wherein the first antigen binding domain comprises a heavy chain variable region sequence that is at least about 95%, 96%, 97%, 98%, 99% or 100% identical to the amino acid sequence of SEQ ID NO:40 and a light chain variable region sequence that is at least about 95%, 96%, 97%, 98%, 99% or 100% identical to the amino acid sequence of SEQ ID NO:41.
79. The bispecific antibody of embodiment 78, wherein the first antigen binding domain comprises the heavy chain variable region sequence of SEQ ID NO:40 and the light chain variable region sequence of SEQ ID NO:41.
80. The bispecific antibody of any one of embodiments 76 to 79, wherein the second and third antigen binding domain comprise a heavy chain variable region sequence that is at least about 95%, 96%, 97%, 98%, 99% or 100% identical to the amino acid sequence of SEQ ID NO:3 and a light chain variable region sequence that is at least about 95%, 96%, 97%, 98%, 99% or 100% identical to the amino acid sequence of SEQ ID NO:4.
81. The bispecific antibody of embodiment 80, wherein the second and third antigen binding domains comprise the heavy chain variable region of SEQ ID NO:3 and the light chain variable region of SEQ ID NO:4.
82. The bispecific antibody of any one of embodiments 76 to 81, wherein the Fc domain incorporates, singly or in combination, all of the features described in Sections 6.1 and 6.2 in relation to Fc domains.
83. The bispecific antibody of any one of embodiments 76 to 82, wherein the antigen binding domains and the Fc region are fused to each other by peptide linkers.
84. The bispecific antibody of embodiment 83, wherein the peptide linkers comprise the peptide linkers as in SEQ ID NO:45 and/or SEQ ID NO:46.
85. The bispecific antibody of any one of embodiments 76 to 84, wherein in the constant domain CL of the second and the third Fab molecule, the amino acid at position 124 is substituted by lysine (K) (numbering according to Kabat) and the amino acid at position 123 is substituted by lysine (K) or arginine (R), preferably by arginine (R) (numbering according to Kabat), and in the constant domain CH1 of the second and the third Fab molecule under (ii) the amino acid at position 147 is substituted by glutamic acid (E) (numbering according to Kabat EU index) and the amino acid at position 213 is substituted by glutamic acid (E) (numbering according to Kabat EU index).
86. The bispecific antibody of any one of embodiments 76 to 85, which comprises a polypeptide comprising a sequence that is at least 80%, 85%, 90%, 95%, 96%, 97%, 98%, or 99% identical to the sequence of SEQ ID NO:43, a polypeptide comprising a sequence that is at least 80%, 85%, 90%, 95%, 96%, 97%, 98%, or 99% identical to the sequence of SEQ ID NO:44, a polypeptide comprising a sequence that is at least 80%, 85%, 90%, 95%, 96%, 97%, 98%, or 99% identical to the sequence of SEQ ID NO:45, and a polypeptide comprising a sequence that is at least 80%, 85%, 90%, 95%, 96%, 97%, 98%, or 99% identical to the sequence of SEQ ID NO:46.
87. The bispecific antibody of embodiment 86, wherein the bispecific antibody comprises a polypeptide comprising the sequence of SEQ ID NO:43, a polypeptide comprising the sequence of SEQ ID NO:44, a polypeptide comprising the sequence of SEQ ID NO:45, and a polypeptide comprising the sequence of SEQ ID NO:46.
88. The bispecific antibody of embodiment 87, which comprises two polypeptides comprising the sequence of SEQ ID NO:43.
89. The bispecific antibody of any one of embodiments 45 to 88 which is conjugated to a detectable moiety.
90. The bispecific antibody of embodiment 89 in which the detectable marker is an enzyme, a radioisotope, or a fluorescent label.
91. A fusion protein comprising the amino acid sequence of the anti-glyco-MUC1 antibody or antigen-binding fragment of any of embodiments 1 to 44 or the bispecific antibody of any one of embodiments 45 to 90 operably linked to at least a second amino acid sequence.
92. The fusion protein of embodiment 91, wherein the second amino acid sequence is that of 4-1BB, CD3-zeta, or a fragment thereof.
93. The fusion protein of embodiment 91, wherein the second amino acid sequence is that of a fusion peptide.
94. The fusion protein of embodiment 93, wherein the fusion peptide is a CD28-CD3-zeta or 4-IBB (CD137)-CD3-zeta fusion peptide.
95. The fusion protein of embodiment 91, wherein the second amino acid sequence is that of a modulator of T cell activation or a fragment thereof.
96. The fusion protein of embodiment 95, wherein the modulator of T cell activation is IL-15 or IL-15Ra.
97. A chimeric antigen receptor (CAR) comprising the scFv of any one of embodiments 24 to 26.
98. The CAR of embodiment 97, comprising in amino- to carboxy-terminal order: a human CD8 leader peptide, the scFv, a human CD8 hinge domain, a human CD8 transmembrane domain, and a CD3-zeta signaling domain.
99. An antibody-drug conjugate comprising the anti-glyco-MUC1 antibody or antigen-binding fragment of any of embodiments 1 to 44 or the bispecific antibody of any one of embodiments 45 to 90 or the fusion protein of any one of embodiments 91 to 96 conjugated to a cytotoxic agent.
100. The antibody-drug conjugate of embodiment 99, wherein the cytotoxic agent is an auristatin, a DNA minor groove binding agent, an alkylating agent, an enediyne, a lexitropsin, a duocarmycin, a taxane, a dolastatin, a maytansinoid, or a vinca alkaloid.
101. The antibody-drug conjugate of embodiment 100, wherein the anti-glyco-MUC1 antibody or antigen-binding fragment or bispecific antibody is conjugated to the cytotoxic agent via a linker.
102. The antibody-drug conjugate of embodiment 101, wherein the linker is cleavable under intracellular conditions.
103. The antibody-drug conjugate of embodiment 102, wherein the cleavable linker is cleavable by an intracellular protease.
104. The antibody-drug conjugate of embodiment 103, wherein the linker comprises a dipeptide.
105. The antibody-drug conjugate of embodiment 104, wherein the dipeptide is val-cit or phe-lys.
106. The antibody-drug conjugate of embodiment 102, wherein the cleavable linker is hydrolyzable at a pH of less than 5.5.
107. The antibody-drug conjugate of embodiment 106, wherein the hydrolyzable linker is a hydrazone linker.

108. The antibody-drug conjugate of embodiment 102, wherein the cleavable linker is a disulfide linker.

109. A nucleic acid comprising a coding region for an anti-glyco-MUC1 antibody or antigen-binding fragment of any of embodiments 1 to 44 or the bispecific antibody of any one of embodiments 45 to 90, the fusion protein of any one of embodiments 91 to 96, or the CAR of embodiment 97 or embodiment 98.

110. The nucleic acid of embodiment 109 in which the coding region is codon-optimized for expression in a human cell.

111. A vector comprising the nucleic acid of embodiment 109 or embodiment 110.

112. The vector of embodiment 111 which is a viral vector.

113. The vector of embodiment 112 wherein the viral vector is a lentiviral vector.

114. A host cell engineered to express the nucleic acid of embodiment 109 or embodiment 110.

115. The host cell of embodiment 114, which is a human T-cell engineered to express the CAR of embodiment 97 or embodiment 98.

116. A host cell comprising the vector of any one of embodiments 111 to 113.

117. The host cell of embodiment 116 which is a T-cell and wherein the vector encodes the CAR of embodiment 97 or embodiment 98.

118. A pharmaceutical composition comprising (a) the anti-glyco-MUC1 antibody or antigen binding fragment of any of embodiments 1 to 44, the bispecific antibody of any one of embodiments 45 to 90, the fusion protein of any one of embodiments 91 to 96, the CAR of embodiment 97 or embodiment 98, the antibody-drug conjugate of any one of embodiments 99 to 108, the nucleic acid of embodiment 109 or embodiment 110, the vector of any one of embodiments 111 to 113, or the host cell of embodiment any one of embodiments 114 to 117, and (b) a physiologically suitable buffer, adjuvant or diluent.

119. A method treating cancer comprising administering to a subject in need thereof an effective amount of the anti-glyco-MUC1 antibody or antigen binding fragment of any of embodiments 1 to 44, the bispecific antibody of any one of embodiments 45 to 90, the fusion protein of any one of embodiments 91 to 96, the CAR of embodiment 97 or embodiment 98, the antibody-drug conjugate of any one of embodiments 99 to 108, the nucleic acid of embodiment 109 or embodiment 110, the vector of any one of embodiments 111 to 113, the host cell of embodiment any one of embodiments 114 to 117, or the pharmaceutical composition of embodiment 118.

120. The method of embodiment 119, wherein the subject is suffering from breast cancer, non-small cell lung cancer, prostate cancer, pancreatic cancer, esophageal cancer, or colorectal cancer.

121. A method of detecting cancer in a biological sample, comprising contacting a sample with an anti-glyco-MUC1 antibody or antigen-binding fragment according to any one of embodiments 1 to 44 and detecting binding of the anti-glyco-MUC1 antibody or antigen-binding fragment.

122. The method of embodiment 121, further comprising quantitating the binding of the anti-glyco-MUC1 antibody or antigen-binding fragment.

123. The method of embodiment 121 or embodiment 122, wherein the binding is compared to a normal tissue control as a negative/baseline control and/or to a cancerous tissue control as a positive control.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

9. REFERENCES

1. Bennett, E. P., Hassan, H., Mandel, U., Mirgorodskaya, E., Roepstorff, P., Burchell, J., Taylor-Papadimitriou, J., Hollingsworth, M. A., Merkx, G., van Kessel, A. G., and others. (1998) Cloning of a human UDP-N-acetyl-alpha-D-galactosamine:polypeptide N-acetylgalactosaminyltransferase that complements other GalNAc-transferases in complete O-glycosylation of the MUC1 tandem repeat. J. Biol. Chem., 273, 30472-30481.
2. Fontenot, J. D., Finn, O. J., Dales, N., Andrews, P. C., and Montelaro, R. C. (1993) Synthesis of large multideterminant peptide immunogens using a poly-proline beta-turn helix motif. Pept. Res., 6, 330-336.
3. Mandel, U., Petersen, O. W., Sorensen, H., Vedtofte, P., Hakomori, S. I., Clausen, H., and Dabelsteen, E. (1991) Simple mucin-type carbohy-drates in oral stratified squamous and salivary-gland epithelia. J. Invest. Dermatol., 97, 713-721.
4. Miles, D. W., Linehan, J., Smith, P., and Filipe, I. (1995) Expression of sialyl-Tn in gastric cancer: correlation with known prognostic factors. Br. J. Cancer., 71, 1074-1076.
5. Schwientek, T., Bennett, E. P., Flores, C., Thacker, J., Hollmann, M., Reis, C. A., Behrens, J., Mandel, U., Keck, B., Schafer, M. A., and others. (2002) Functional conservation of subfamilies of putative UDP-N-acetylgalactosamine:polypeptide N-acetylgalactosaminyltransferases in Drosophila, Caenorhabditis elegans, and mammals. One subfamily composed of I(2)35Aa is essential in Drosophila. J. Biol. Chem., 277, 22623-22638.
6. Soares, R., Marinho, A., and Schmitt, F. (1996) Expression of Sialyl-Tn in breast cancer. Correlation with prognostic parameters. Pathol. Res. Pract., 192, 1181-1186.
7. Springer, G. F. (1984) T and Tn, general carcinoma auto-antigens. Science, 224, 1198-1206.
8. Werther, J. L., Tatematsu, M., Klein, R., Kurihara, M., Kumagai, K., Llorens, P., Guidugli, N. J., Bodian, C., Pertsemlidis, D., Yamachika, T., and others. (1996) Sialosyl-Tn antigen as a marker of gastric cancer progression: an international study. Int. J. Cancer., 69, 193-199.
9. Taylor-Papadimitriou, J., Burchell, J., Miles, D. W., and Dalziel, M. (1999) MUC1 and cancer. Biochim. Biophys. Acta, 1455, 301-313.

What is claimed is:

1. A method of treating cancer comprising administering to a subject in need thereof an effective amount of an anti-glyco-MUC1 antibody or antigen binding fragment that:
   a. comprises a complementarity determining region (CDR) H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31; and
   b. binds to the MUC1 tandem repeat (VTSAPDTRPAPG-STAPPAHG)$_3$ (SEQ ID NO:47) that has been glycosylated in vitro using purified recombinant human glycosyltransferases GalNAc-T1, GalNAc-T2, and GalNAc-T4 (referred to hereinafter as the "first epitope").

2. A method of treating cancer comprising administering to a subject in need thereof an effective amount of an anti-glyco-MUC1 antibody or antigen binding fragment that:
   a. comprises a complementarity determining region (CDR) H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31; and
   b. preferentially binds to a glyco-MUC1 epitope that is overexpressed on cancer cells as compared to normal cells.

3. The method of claim 1, wherein the anti-glyco-MUC1 antibody or antigen-binding fragment comprises a heavy chain variable (VH) sequence comprising complementarity determining regions (CDRs) of SEQ ID NOS:5-7 and a light chain variable (VL) sequence comprising CDRs of SEQ ID NOS:8-10.

4. The method of claim 1, wherein the anti-glyco-MUC1 antibody or antigen-binding fragment comprises a heavy chain variable (VH) sequence comprising complementarity determining regions (CDRs) of SEQ ID NOS:23-25 and a light chain variable (VL) sequence comprising CDRs of SEQ ID NOS:26, 27, and 10.

5. The method of claim 1, wherein the anti-glyco-MUC1 antibody or antigen-binding fragment comprises a heavy chain variable (VH) sequence comprising complementarity determining regions (CDRs) of SEQ ID NOS:28, 29, and 25 and a light chain variable (VL) sequence comprising CDRs of SEQ ID NOS:30, 9, and 31.

6. The method of claim 1, wherein the anti-glyco-MUC1 antibody or antigen-binding fragment is a chimeric antibody.

7. The method of claim 1, wherein the anti-glyco-MUC1 antibody or antigen-binding fragment is a humanized antibody.

8. The method of claim 1, wherein the anti-glyco-MUC1 antibody or antigen-binding fragment comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

9. The method of claim 2, wherein the anti-glyco-MUC1 antibody or antigen-binding fragment comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

10. The method of claim 7, wherein the anti-glyco-MUC1 antibody or antigen-binding fragment comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

11. The method of claim 1, wherein the anti-glyco-MUC1 antibody or antigen-binding fragment comprises a heavy chain variable (VH) sequence comprising the amino acid sequence of SEQ ID NO:3 and a light chain variable (VL) sequence comprising the amino acid sequence of SEQ ID NO:4.

12. The method of claim 1, wherein the anti-glyco-MUC1 antibody or antigen-binding fragment is multivalent.

13. The method of claim 1, wherein the anti-glyco-MUC1 antibody or antigen-binding fragment is in the form of a single-chain variable fragment (scFv).

14. The method of claim 1, wherein the anti-glyco-MUC1 antibody or antigen-binding fragment is in the form of a multispecific antibody.

15. The method of claim 14, wherein the multispecific antibody is a bispecific antibody that binds to a second epitope that is different from the first epitope.

16. The method of claim 15, wherein the bispecific antibody comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

17. The method of claim 15, wherein the second epitope is a T-cell epitope.

18. The method of claim 17, wherein the T-cell epitope comprises a CD3 epitope, a CD8 epitope, a CD16 epitope, a CD25 epitope, a CD28 epitope, or an NKG2D epitope.

19. The method of claim 18, wherein the T-cell epitope comprises a CD3 epitope.

20. The method of claim 19, wherein the bispecific antibody comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

21. The method of claim 19, wherein the CD3 epitope comprises a CD3 gamma epitope, a CD3 delta epitope, a CD3 epsilon epitope, or a CD3 zeta epitope.

22. The method of claim 19, wherein the bispecific antibody comprises an IgG Fc domain composed of two subunits.

23. The method of claim 22, wherein the bispecific antibody comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

24. The method of claim 19, wherein the bispecific antibody comprises a CD3 binding domain comprising a heavy chain variable (VH) sequence comprising complementarity determining regions (CDRs) of SEQ ID NOS:34-36 and a light chain variable (VL) sequence comprising CDRs of SEQ ID NOS:37-39.

25. The method of claim 24, wherein the bispecific antibody comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

26. The method of claim 19, wherein the bispecific antibody is a bispecific IgG comprising a Fab-arm having a domain crossover between heavy and light chains.

27. The method of claim 26, wherein the bispecific antibody comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

28. The method of claim 19, wherein the MUC1 tandem repeat and CD3 binding portions of the bispecific antibody are in the form of Fabs, wherein the CD3 binding portion is a crossover Fab whose light and heavy chain variable or constant regions are exchanged.

29. The method of claim 28, wherein the bispecific antibody comprises a heavy chain variable (VH) sequence comprising an amino acid sequence having at least 95% sequence identity to SEQ ID NO:3 and a light chain variable (VL) sequence comprising an amino acid sequence having at least 95% sequence identity to SEQ ID NO:4.

30. The method of claim 1, wherein the subject is suffering from breast cancer, non-small cell lung cancer, prostate cancer, pancreatic cancer, esophageal cancer, or colorectal cancer.

31. A method detecting cancer in a biological sample, comprising contacting a sample with an anti-glyco-MUC1 antibody or antigen-binding fragment and detecting binding of the anti-glyco-MUC1 antibody or antigen-binding fragment, wherein the anti-glyco-MUC1 antibody or antigen-binding fragment:
   a. comprises a complementarity determining region (CDR) H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31; and
   b. binds to the MUC1 tandem repeat (VTSAPDTRPAPG-STAPPAHG)$_3$ (SEQ ID NO:47) that has been glycosylated in vitro using purified recombinant human glycosyltransferases GalNAc-T1, GalNAc-T2, and GalNAc-T4.

32. A method detecting cancer in a biological sample, comprising contacting a sample with an anti-glyco-MUC1 antibody or antigen-binding fragment and detecting binding of the anti-glyco-MUC1 antibody or antigen-binding fragment, wherein the anti-glyco-MUC1 antibody or antigen-binding fragment:
   a. comprises a complementarity determining region (CDR) H1 comprising the amino acid sequence of SEQ ID NO:33, a CDR-H2 comprising the amino acid sequence of SEQ ID NO:29, a CDR-H3 comprising the amino acid sequence of SEQ ID NO:25, a CDR-L1 comprising the amino acid sequence of SEQ ID NO: 8, a CDR-L2 comprising the amino acid sequence of SEQ ID NO:9, and a CDR-L3 comprising the amino acid sequence of SEQ ID NO:31; and b. preferentially binds to a glyco-MUC1 epitope that is overexpressed on cancer cells as compared to normal cells.

\* \* \* \* \*

SEQUENCE LISTING

<160> NUMBER OF SEQ ID NOS: 57

<210> SEQ ID NO 1
<211> LENGTH: 136
<212> TYPE: PRT
<213> ORGANISM: Mus musculus

<400> SEQUENCE: 1

```
Met Gly Trp Ser Gly Ile Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Arg Pro Glu Gln Gly Leu
    50                  55                  60

Glu Trp Ile Gly Tyr Phe Ser Pro Gly Asn Asp Asp Ile His Tyr Asn
65                  70                  75                  80

Glu Lys Phe Glu Gly Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Lys Arg Ser Tyr Asp Lys Asp Phe Asp Cys Trp Gly Gln
        115                 120                 125

Gly Thr Thr Leu Thr Val Ser Ser
    130                 135
```

<210> SEQ ID NO 2
<211> LENGTH: 140
<212> TYPE: PRT
<213> ORGANISM: Mus musculus

<400> SEQUENCE: 2

```
Met Val Leu Ile Leu Leu Leu Trp Val Ser Gly Thr Cys Gly Asp
1               5                   10                  15

Ile Val Met Ser Gln Ser Pro Ser Ser Leu Gly Val Ser Val Gly Glu
            20                  25                  30

Lys Val Thr Met Ser Cys Lys Ser Ser Gln Ser Leu Leu Tyr Ser Thr
        35                  40                  45

Asn Gln Lys Asn Tyr Gln Ser Leu Leu Tyr Ser Thr Asn Gln Lys Asn
    50                  55                  60

Tyr Leu Ala Trp Tyr Gln Gln Lys Pro Gly Gln Ser Pro Lys Leu Leu
65                  70                  75                  80

Ile Tyr Trp Val Ser Asn Arg Lys Ser Gly Val Pro Asp Arg Phe Thr
                85                  90                  95

Gly Ser Gly Ser Gly Thr Asp Phe Thr Leu Thr Ile Ser Ser Val Lys
            100                 105                 110

Ala Glu Asp Leu Ala Val Tyr Tyr Cys Gln Gln Tyr Tyr Arg Tyr Pro
        115                 120                 125

Leu Thr Phe Gly Ala Gly Thr Lys Leu Glu Leu Lys
    130                 135                 140
```

<210> SEQ ID NO 3
<211> LENGTH: 117
<212> TYPE: PRT
<213> ORGANISM: Mus musculus

<400> SEQUENCE: 3

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Arg Pro Glu Gln Gly Leu Glu Trp Ile
            35                  40                  45

Gly Tyr Phe Ser Pro Gly Asn Asp Asp Ile His Tyr Asn Glu Lys Phe
        50                  55                  60

Glu Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Asp Lys Asp Phe Asp Cys Trp Gly Gln Gly Thr Thr
                100                 105                 110

Leu Thr Val Ser Ser
        115

<210> SEQ ID NO 4
<211> LENGTH: 125
<212> TYPE: PRT
<213> ORGANISM: Mus musculus

<400> SEQUENCE: 4

Asp Ile Val Met Ser Gln Ser Pro Ser Ser Leu Gly Val Ser Val Gly
1               5                   10                  15

Glu Lys Val Thr Met Ser Cys Lys Ser Ser Gln Ser Leu Leu Tyr Ser
                20                  25                  30

Thr Asn Gln Lys Asn Tyr Gln Ser Leu Leu Tyr Ser Thr Asn Gln Lys
            35                  40                  45

Asn Tyr Leu Ala Trp Tyr Gln Gln Lys Pro Gly Gln Ser Pro Lys Leu
        50                  55                  60

Leu Ile Tyr Trp Val Ser Asn Arg Lys Ser Gly Val Pro Asp Arg Phe
65                  70                  75                  80

Thr Gly Ser Gly Ser Gly Thr Asp Phe Thr Leu Thr Ile Ser Ser Val
                85                  90                  95

Lys Ala Glu Asp Leu Ala Val Tyr Tyr Cys Gln Gln Tyr Tyr Arg Tyr
                100                 105                 110

Pro Leu Thr Phe Gly Ala Gly Thr Lys Leu Glu Leu Lys
            115                 120                 125

<210> SEQ ID NO 5
<211> LENGTH: 8
<212> TYPE: PRT
<213> ORGANISM: Mus musculus

<400> SEQUENCE: 5

Gly Tyr Thr Phe Thr Asp His Ala
1               5

<210> SEQ ID NO 6
<211> LENGTH: 8
<212> TYPE: PRT
<213> ORGANISM: Mus musculus

<400> SEQUENCE: 6

Phe Ser Pro Gly Asn Asp Asp Ile
1               5
```

<210> SEQ ID NO 7
<211> LENGTH: 10
<212> TYPE: PRT
<213> ORGANISM: Mus musculus

<400> SEQUENCE: 7

Lys Arg Ser Tyr Asp Lys Asp Phe Asp Cys
1               5                   10

<210> SEQ ID NO 8
<211> LENGTH: 12
<212> TYPE: PRT
<213> ORGANISM: Mus musculus

<400> SEQUENCE: 8

Gln Ser Leu Leu Tyr Ser Thr Asn Gln Lys Asn Tyr
1               5                   10

<210> SEQ ID NO 9
<211> LENGTH: 3
<212> TYPE: PRT
<213> ORGANISM: Mus musculus

<400> SEQUENCE: 9

Trp Val Ser
1

<210> SEQ ID NO 10
<211> LENGTH: 9
<212> TYPE: PRT
<213> ORGANISM: Mus musculus

<400> SEQUENCE: 10

Gln Gln Tyr Tyr Arg Tyr Pro Leu Thr
1               5

<210> SEQ ID NO 11
<211> LENGTH: 408
<212> TYPE: DNA
<213> ORGANISM: Mus musculus

<400> SEQUENCE: 11
atgggatgga gcgggatctt tctcttcttc ctgtcagtaa ctacaggtgt ccactcccag      60
gttcagctgc agcagtctga cgcggagttg gtgaaacctg ggcttcagt gaagatatcc     120 tgcaaggctt ctggctacac tttcactgac catgctattc actgggtgaa gcagaggcct    180
gaacagggcc tggaatggat tggatatttt tctcccggaa atgatgacat tcactacaat    240
gagaagttcg agggcaaggc cacactgact gcagacaaat cctccagcac tgcctacatg    300
cagctcaaca gcctgacatc tgaagattct gcagtgtatt tctgtaaaag atcttacgac    360
aaggactttg actgctgggg ccaaggcacc actctcacag tctcctca                 408

<210> SEQ ID NO 12
<211> LENGTH: 384
<212> TYPE: DNA
<213> ORGANISM: Mus musculus

<400> SEQUENCE: 12
atggttctta tcttactgct gctatgggta tctggtacct gtggggacat tgtgatgtca     60
cagtctccat cctccctagg tgtgtcagtt ggagagaagg ttactatgag ctgcaagtcc    120
agtcagagcc ttttatacag taccaatcaa aagaactacc tggcctggta ccagcagaaa    180

```
ccagggcagt ctcctaagtt gctgatttac tgggtatcta ataggaaatc tggggtccct    240
gatcgcttca caggcagtgg atctgggaca gatttcactc tcaccatcag tagtgtgaag    300
gctgaagacc tggcagttta ttactgtcag caatattata ggtatccgct cacgttcggt    360
gctgggacca agctggagct gaaa                                           384

<210> SEQ ID NO 13
<211> LENGTH: 351
<212> TYPE: DNA
<213> ORGANISM: Mus musculus

<400> SEQUENCE: 13
caggttcagc tgcagcagtc tgacgcggag ttggtgaaac ctggggcttc agtgaagata    60
tcctgcaagg cttctggcta cactttcact gaccatgcta ttcactgggt gaagcagagg    120
cctgaacagg gcctggaatg gattggatat tttctcccg gaaatgatga cattcactac    180
aatgagaagt tcgagggcaa ggccacactg actgcagaca atcctccag cactgcctac    240 atgcagctca acagcctgac atctgaagat tctgcagtgt atttctgtaa aagatcttac    300
gacaaggact ttgactgctg gggccaaggc accactctca cagtctcctc a            351

<210> SEQ ID NO 14
<211> LENGTH: 339
<212> TYPE: DNA
<213> ORGANISM: Mus musculus

<400> SEQUENCE: 14
gacattgtga tgtcacagtc tccatcctcc ctaggtgtgt cagttggaga gaaggttact    60
atgagctgca gtccagtca gagccttta tacagtacca tcaaaagaa ctacctggcc      120 tggtaccagc agaaaccagg gcagtctcct aagttgctga tttactgggt atctaatagg    180
aaatctgggg tccctgatcg cttcacaggc agtggatctg gacagattt cactctcacc     240 atcagtagtg tgaaggctga agacctggca gtttattact gtcagcaata ttataggtat    300
ccgctcacgt tcggtgctgg gaccaagctg gagctgaaa                          339

<210> SEQ ID NO 15
<211> LENGTH: 25
<212> TYPE: PRT
<213> ORGANISM: Mus musculus

<400> SEQUENCE: 15

Gln Val Gln Leu Gln Gln Ser Asp Ala Glu Leu Val Lys Pro Gly Ala
1               5                   10                  15

Ser Val Lys Ile Ser Cys Lys Ala Ser
            20                  25

<210> SEQ ID NO 16
<211> LENGTH: 17
<212> TYPE: PRT
<213> ORGANISM: Mus musculus

<400> SEQUENCE: 16

Ile His Trp Val Lys Gln Arg Pro Glu Gln Gly Leu Glu Trp Ile Gly
1               5                   10                  15

Tyr

<210> SEQ ID NO 17
<211> LENGTH: 38
```

<212> TYPE: PRT
<213> ORGANISM: Mus musculus

<400> SEQUENCE: 17

His Tyr Asn Glu Lys Phe Glu Gly Lys Ala Thr Leu Thr Ala Asp Lys
1               5                   10                  15

Ser Ser Ser Thr Ala Tyr Met Gln Leu Asn Ser Leu Thr Ser Glu Asp
            20                  25                  30

Ser Ala Val Tyr Phe Cys
        35

<210> SEQ ID NO 18
<211> LENGTH: 11
<212> TYPE: PRT
<213> ORGANISM: Mus musculus

<400> SEQUENCE: 18

Trp Gly Gln Gly Thr Thr Leu Thr Val Ser Ser
1               5                   10

<210> SEQ ID NO 19
<211> LENGTH: 26
<212> TYPE: PRT
<213> ORGANISM: Mus musculus

<400> SEQUENCE: 19

Asp Ile Val Met Ser Gln Ser Pro Ser Ser Leu Gly Val Ser Val Gly
1               5                   10                  15

Glu Lys Val Thr Met Ser Cys Lys Ser Ser
            20                  25

<210> SEQ ID NO 20
<211> LENGTH: 17
<212> TYPE: PRT
<213> ORGANISM: Mus musculus

<400> SEQUENCE: 20

Leu Ala Trp Tyr Gln Gln Lys Pro Gly Gln Ser Pro Lys Leu Leu Ile
1               5                   10                  15

Tyr

<210> SEQ ID NO 21
<211> LENGTH: 36
<212> TYPE: PRT
<213> ORGANISM: Mus musculus

<400> SEQUENCE: 21

Asn Arg Lys Ser Gly Val Pro Asp Arg Phe Thr Gly Ser Gly Ser Gly
1               5                   10                  15

Thr Asp Phe Thr Leu Thr Ile Ser Ser Val Lys Ala Glu Asp Leu Ala
            20                  25                  30

Val Tyr Tyr Cys
        35

<210> SEQ ID NO 22
<211> LENGTH: 10
<212> TYPE: PRT
<213> ORGANISM: Mus musculus

<400> SEQUENCE: 22

Phe Gly Ala Gly Thr Lys Leu Glu Leu Lys
1               5                   10

<210> SEQ ID NO 23
<211> LENGTH: 5
<212> TYPE: PRT
<213> ORGANISM: Mus musculus

<400> SEQUENCE: 23

Asp His Ala Ile His
1               5

<210> SEQ ID NO 24
<211> LENGTH: 17
<212> TYPE: PRT
<213> ORGANISM: Mus musculus

<400> SEQUENCE: 24

Tyr Phe Ser Pro Gly Asn Asp Asp Ile His Tyr Asn Glu Lys Phe Glu
1               5                   10                  15

Gly

<210> SEQ ID NO 25
<211> LENGTH: 8
<212> TYPE: PRT
<213> ORGANISM: Mus musculus

<400> SEQUENCE: 25

Ser Tyr Asp Lys Asp Phe Asp Cys
1               5

<210> SEQ ID NO 26
<211> LENGTH: 17
<212> TYPE: PRT
<213> ORGANISM: Mus musculus

<400> SEQUENCE: 26

Lys Ser Ser Gln Ser Leu Leu Tyr Ser Thr Asn Gln Lys Asn Tyr Leu
1               5                   10                  15

Ala

<210> SEQ ID NO 27
<211> LENGTH: 7
<212> TYPE: PRT
<213> ORGANISM: Mus musculus

<400> SEQUENCE: 27

Trp Val Ser Asn Arg Lys Ser
1               5

<210> SEQ ID NO 28
<211> LENGTH: 7
<212> TYPE: PRT
<213> ORGANISM: Mus musculus

<400> SEQUENCE: 28

Gly Tyr Thr Phe Thr Asp His
1               5

<210> SEQ ID NO 29
<211> LENGTH: 6
<212> TYPE: PRT
<213> ORGANISM: Mus musculus

<400> SEQUENCE: 29

Ser Pro Gly Asn Asp Asp
1               5

<210> SEQ ID NO 30
<211> LENGTH: 13
<212> TYPE: PRT
<213> ORGANISM: Mus musculus

<400> SEQUENCE: 30

Ser Gln Ser Leu Leu Tyr Ser Thr Asn Gln Lys Asn Tyr
1               5                   10

<210> SEQ ID NO 31
<211> LENGTH: 7
<212> TYPE: PRT
<213> ORGANISM: Mus musculus

<400> SEQUENCE: 31

Tyr Tyr Arg Tyr Pro Leu Thr
1               5

<210> SEQ ID NO 32
<211> LENGTH: 10
<212> TYPE: PRT
<213> ORGANISM: Mus musculus

<400> SEQUENCE: 32

Gly Tyr Thr Phe Thr Asp His Ala Ile His
1               5                   10

<210> SEQ ID NO 33
<211> LENGTH: 2
<212> TYPE: PRT
<213> ORGANISM: Mus musculus

<400> SEQUENCE: 33

Asp His
1

<210> SEQ ID NO 34
<211> LENGTH: 5
<212> TYPE: PRT
<213> ORGANISM: Artificial Sequence
<220> FEATURE:
<223> OTHER INFORMATION: synthetic CD3 CDR-H1 peptide

<400> SEQUENCE: 34

Thr Tyr Ala Met Asn
1               5

<210> SEQ ID NO 35
<211> LENGTH: 19
<212> TYPE: PRT
<213> ORGANISM: Artificial Sequence
<220> FEATURE:
<223> OTHER INFORMATION: synthetic CD3 CDR-H2 peptide

<400> SEQUENCE: 35

Arg Ile Arg Ser Lys Tyr Asn Asn Tyr Ala Thr Tyr Tyr Ala Asp Ser
1               5                   10                  15

Val Lys Gly

<210> SEQ ID NO 36
<211> LENGTH: 14
<212> TYPE: PRT

```
<213> ORGANISM: Artificial Sequence
<220> FEATURE:
<223> OTHER INFORMATION: synthetic CD3 CDR-H3 peptide

<400> SEQUENCE: 36

His Gly Asn Phe Gly Asn Ser Tyr Val Ser Trp Phe Ala Tyr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic CD3 CDR-L1 peptide

<400> SEQUENCE: 37

Gly Ser Ser Thr Gly Ala Val Thr Thr Ser Asn Tyr Ala Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: synthetic CD3 CDR-L2  peptide

<400> SEQUENCE: 38

Gly Thr Asn Lys Arg Ala Pro
1               5

<210> SEQ ID NO 39
<211> LENGTH: 9
<212> TYPE: PRT
<213> ORGANISM: Artificial Sequence
<220> FEATURE:
<223> OTHER INFORMATION: synthetic CD3 CDR-L2 peptide

<400> SEQUENCE: 39

Ala Leu Trp Tyr Ser Asn Leu Trp Val
1               5

<210> SEQ ID NO 40
<211> LENGTH: 125
<212> TYPE: PRT
<213> ORGANISM: Artificial Sequence
<220> FEATURE:
<223> OTHER INFORMATION: synthetic CD3 VH

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110
```

Ala Tyr Trp Gly Gln Gly Thr Leu Val Thr Val Ser Ser
            115                 120                 125

<210> SEQ ID NO 41
<211> LENGTH: 109
<212> TYPE: PRT
<213> ORGANISM: Artificial Sequence
<220> FEATURE:
<223> OTHER INFORMATION: synthetic CD3 VL

<400> SEQUENCE: 41

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 42
<211> LENGTH: 225
<212> TYPE: PRT
<213> ORGANISM: Artificial Sequence
<220> FEATURE:
<223> OTHER INFORMATION: synthetic hIgG1 Fc region

<400> SEQUENCE: 42

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro
225

<210> SEQ ID NO 43
<211> LENGTH: 232
<212> TYPE: PRT
<213> ORGANISM: Artificial Sequence
<220> FEATURE:
<223> OTHER INFORMATION: synthetic MUC1 VL-CL(RK)

<400> SEQUENCE: 43

Asp Ile Val Met Ser Gln Ser Pro Ser Ser Leu Gly Val Ser Val Gly
1               5                   10                  15

Glu Lys Val Thr Met Ser Cys Lys Ser Ser Gln Ser Leu Leu Tyr Ser
            20                  25                  30

Thr Asn Gln Lys Asn Tyr Gln Ser Leu Leu Tyr Ser Thr Asn Gln Lys
        35                  40                  45

Asn Tyr Leu Ala Trp Tyr Gln Gln Lys Pro Gly Gln Ser Pro Lys Leu
    50                  55                  60

Leu Ile Tyr Trp Val Ser Asn Arg Lys Ser Gly Val Pro Asp Arg Phe
65                  70                  75                  80

Thr Gly Ser Gly Ser Gly Thr Asp Phe Thr Leu Thr Ile Ser Ser Val
                85                  90                  95

Lys Ala Glu Asp Leu Ala Val Tyr Tyr Cys Gln Gln Tyr Tyr Arg Tyr
            100                 105                 110

Pro Leu Thr Phe Gly Ala Gly Thr Lys Leu Glu Leu Lys Arg Thr Val
        115                 120                 125

Ala Ala Pro Ser Val Phe Ile Phe Pro Pro Ser Asp Arg Lys Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 44
<211> LENGTH: 232
<212> TYPE: PRT
<213> ORGANISM: Artificial Sequence
<220> FEATURE:
<223> OTHER INFORMATION: synthetic CD3 VH-CL

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr

```
                    20                  25                  30
Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
         50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
             115                 120                 125

Ala Ala Pro Ser Val Phe Ile Phe Pro Pro Ser Asp Glu Gln Leu Lys
         130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
         195                 200                 205

Val Tyr Ala Cys Glu Val Thr His Gln Gly Leu Ser Ser Pro Val Thr
     210                 215                 220

Lys Ser Phe Asn Arg Gly Glu Cys
225                 230

<210> SEQ ID NO 45
<211> LENGTH: 447
<212> TYPE: PRT
<213> ORGANISM: Artificial Sequence
<220> FEATURE:
<223> OTHER INFORMATION: MUC1 VH-CH1(EE)-Fc (hole, P329G LALA)

<400> SEQUENCE: 45

Gln Val Gln Leu Gln Gln Ser Asp Ala Glu Leu Val Lys Pro Gly Ala
 1               5                  10                  15

Ser Val Lys Ile Ser Cys Lys Ala Ser Gly Tyr Thr Phe Thr Asp His
             20                  25                  30

Ala Ile His Trp Val Lys Gln Arg Pro Glu Gln Gly Leu Glu Trp Ile
         35                  40                  45

Gly Tyr Phe Ser Pro Gly Asn Asp Asp Ile His Tyr Asn Glu Lys Phe
     50                  55                  60

Glu Gly Lys Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                 85                  90                  95

Lys Arg Ser Tyr Asp Lys Asp Phe Asp Cys Trp Gly Gln Gly Thr Thr
            100                 105                 110

Leu Thr Val Ser Ser Ala Ser Thr Lys Gly Pro Ser Val Phe Pro Leu
             115                 120                 125

Ala Pro Ser Ser Lys Ser Thr Ser Gly Gly Thr Ala Ala Leu Gly Cys
         130                 135                 140

Leu Val Glu Asp Tyr Phe Pro Glu Pro Val Thr Val Ser Trp Asn Ser
```

Gly Ala Leu Thr Ser Gly Val His Thr Phe Pro Ala Val Leu Gln Ser
145                 150                 155                 160

Ser Gly Leu Tyr Ser Leu Ser Ser Val Val Thr Val Pro Ser Ser Ser
            165                 170                 175

Leu Gly Thr Gln Thr Tyr Ile Cys Asn Val Asn His Lys Pro Ser Asn
        180                 185                 190

Thr Lys Val Asp Glu Lys Val Glu Pro Lys Ser Cys Asp Lys Thr His
    195                 200                 205

Thr Cys Pro Pro Cys Pro Ala Pro Glu Ala Ala Gly Gly Pro Ser Val
210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
            245                 250                 255

Val Lys Phe Asn Trp Tyr Val Asp Gly Val Glu Val His Asn Ala Lys
        260                 265                 270

Thr Lys Pro Arg Glu Glu Gln Tyr Asn Ser Thr Tyr Arg Val Val Ser
    275                 280                 285

Val Leu Thr Val Leu His Gln Asp Trp Leu Asn Gly Lys Glu Tyr Lys
290                 295                 300

Cys Lys Val Ser Asn Lys Ala Leu Gly Ala Pro Ile Glu Lys Thr Ile
305                 310                 315                 320

Ser Lys Ala Lys Gly Gln Pro Arg Glu Pro Gln Val Cys Thr Leu Pro
            325                 330                 335

Pro Ser Arg Asp Glu Leu Thr Lys Asn Gln Val Ser Leu Ser Cys Ala
        340                 345                 350

Val Lys Gly Phe Tyr Pro Ser Asp Ile Ala Val Glu Trp Glu Ser Asn
    355                 360                 365

Gly Gln Pro Glu Asn Asn Tyr Lys Thr Thr Pro Pro Val Leu Asp Ser
370                 375                 380

Asp Gly Ser Phe Phe Leu Val Ser Lys Leu Thr Val Asp Lys Ser Arg
385                 390                 395                 400

Trp Gln Gln Gly Asn Val Phe Ser Cys Ser Val Met His Glu Ala Leu
            405                 410                 415

His Asn His Tyr Thr Gln Lys Ser Leu Ser Leu Ser Pro Gly Lys
        420                 425                 430

<210> SEQ ID NO 46
<211> LENGTH: 672
<212> TYPE: PRT
<213> ORGANISM: Artificial Sequence
<220> FEATURE:
<223> OTHER INFORMATION: synthetic MUC1 VH-CH1(EE)-CD3 VL-CH1-Fc (knob, P329G LALA)

<400> SEQUENCE: 46

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Arg Pro Glu Gln Gly Leu Glu Trp Ile
        35                  40                  45

Gly Tyr Phe Ser Pro Gly Asn Asp Asp Ile His Tyr Asn Glu Lys Phe
    50                  55                  60

```
Glu Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Asp Lys Asp Phe Asp Cys Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Gly Gly Gly
    210                 215                 220

Gly Ser Gly Gly Gly Gly Ser Gln Ala Val Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Glu Lys
            260                 265                 270

Pro Gly Gln Ala Phe Arg Gly Leu Ile Gly Gly Thr Asn Lys Arg Ala
        275                 280                 285

Pro Gly Thr Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320

Cys Ala Leu Trp Tyr Ser Asn Leu Trp Val Phe Gly Gly Gly Thr Lys
                325                 330                 335

Leu Thr Val Leu Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
```

```
                        485                 490                 495

Glu Val Lys Phe Asn Trp Tyr Val Asp Gly Val Glu Val His Asn Ala
                    500                 505                 510

Lys Thr Lys Pro Arg Glu Glu Gln Tyr Asn Ser Thr Tyr Arg Val Val
                515                 520                 525

Ser Val Leu Thr Val Leu His Gln Asp Trp Leu Asn Gly Lys Glu Tyr
            530                 535                 540

Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
            595                 600                 605

Asn Gly Gln Pro Glu Asn Asn Tyr Lys Thr Thr Pro Pro Val Leu Asp
        610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670

<210> SEQ ID NO 47
<211> LENGTH: 60
<212> TYPE: PRT
<213> ORGANISM: Homo sapiens

<400> SEQUENCE: 47

Val Thr Ser Ala Pro Asp Thr Arg Pro Ala Pro Gly Ser Thr Ala Pro
1               5                   10                  15

Pro Ala His Gly Val Thr Ser Ala Pro Asp Thr Arg Pro Ala Pro Gly
            20                  25                  30

Ser Thr Ala Pro Pro Ala His Gly Val Thr Ser Ala Pro Asp Thr Arg
        35                  40                  45

Pro Ala Pro Gly Ser Thr Ala Pro Pro Ala His Gly
    50                  55                  60

<210> SEQ ID NO 48
<211> LENGTH: 21
<212> TYPE: PRT
<213> ORGANISM: Homo sapiens

<400> SEQUENCE: 48

Pro Asp Thr Ser Ala Ala Pro Gly Ser Thr Ala Pro Ala His Val
1               5                   10                  15

Val Thr Ser Ala Pro
            20

<210> SEQ ID NO 49
<211> LENGTH: 21
<212> TYPE: PRT
<213> ORGANISM: Macaca fascicularis

<400> SEQUENCE: 49

Pro Asp Thr Ser Ala Ala Pro Gly Ser Thr Gly Pro Pro Ala His Val
1               5                   10                  15
```

```
Val Thr Ser Ala Pro
            20

<210> SEQ ID NO 50
<211> LENGTH: 20
<212> TYPE: PRT
<213> ORGANISM: Homo sapiens

<400> SEQUENCE: 50

Val Thr Ser Ala Pro Asp Thr Arg Pro Ala Pro Gly Ser Thr Ala Pro
1               5                   10                  15

Pro Ala His Gly
            20

<210> SEQ ID NO 51
<211> LENGTH: 20
<212> TYPE: PRT
<213> ORGANISM: Homo sapiens

<400> SEQUENCE: 51

Pro Thr Thr Thr Pro Ile Ser Thr Thr Met Val Thr Pro Thr Pro
1               5                   10                  15

Thr Pro Thr Cys
            20

<210> SEQ ID NO 52
<211> LENGTH: 21
<212> TYPE: PRT
<213> ORGANISM: Homo sapiens

<400> SEQUENCE: 52

Cys Pro Leu Pro Val Thr Asp Thr Ser Ser Ala Ser Thr Gly His Ala
1               5                   10                  15

Thr Pro Leu Pro Val
            20

<210> SEQ ID NO 53
<211> LENGTH: 24
<212> TYPE: PRT
<213> ORGANISM: homo sapiens

<400> SEQUENCE: 53

Tyr Leu His Leu Gly Ala Leu Gly Arg Asp Leu Trp Gly Pro Ser Pro
1               5                   10                  15

Val Thr Gly Tyr His Pro Leu Leu
            20

<210> SEQ ID NO 54
<211> LENGTH: 27
<212> TYPE: PRT
<213> ORGANISM: homo sapiens

<400> SEQUENCE: 54

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 55
<211> LENGTH: 44
<212> TYPE: PRT
<213> ORGANISM: homo sapiens
```

```
<400> SEQUENCE: 55

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20              25                  30

Gly Ala Val His Thr Arg Gly Leu Asp Phe Ala Cys
            35              40

<210> SEQ ID NO 56
<211> LENGTH: 4
<212> TYPE: PRT
<213> ORGANISM: Artificial Sequence
<220> FEATURE:
<223> OTHER INFORMATION: linker

<400> SEQUENCE: 56

Gly Phe Leu Gly
1

<210> SEQ ID NO 57
<211> LENGTH: 4
<212> TYPE: PRT
<213> ORGANISM: Artificial Sequence
<220> FEATURE:
<223> OTHER INFORMATION: linker

<400> SEQUENCE: 57

Ala Leu Ala Leu
1
```